(12) United States Patent
Yu et al.

(10) Patent No.: US 8,283,414 B2
(45) Date of Patent: Oct. 9, 2012

(54) COMPOSITIONS COMPRISING MODIFIED COLLAGEN AND USES THEREFOR

(75) Inventors: Michael Yu, Timonium, MD (US); Jennifer H. Elisseeff, Baltimore, MD (US); Hyeseung Janice Lee, Washington, DC (US); Xiao Mo, Lutherville, MD (US); Allen Yi-Lan Wang, Vienna, VA (US)

(73) Assignee: The Johns Hopkins University, Baltimore, MD (US)

( * ) Notice: Subject to any disclaimer, the term of this patent is extended or adjusted under 35 U.S.C. 154(b) by 932 days.

(21) Appl. No.: 11/791,425

(22) PCT Filed: Nov. 23, 2005

(86) PCT No.: PCT/US2005/042813
§ 371 (c)(1), (2), (4) Date: Jun. 25, 2008

(87) PCT Pub. No.: WO2007/044026
PCT Pub. Date: Apr. 19, 2007

(65) Prior Publication Data
US 2008/0287342 A1    Nov. 20, 2008

Related U.S. Application Data

(60) Provisional application No. 60/630,271, filed on Nov. 23, 2004, provisional application No. 60/722,079, filed on Sep. 29, 2005.

(51) Int. Cl.
*A61K 38/39*    (2006.01)
*A61K 47/48*    (2006.01)
*C08L 89/00*    (2006.01)
*C07K 1/00*    (2006.01)
*C07K 1/02*    (2006.01)
*C07K 1/13*    (2006.01)

(52) U.S. Cl. .................. 525/54.1; 530/356; 514/17.2

(58) Field of Classification Search .................. None
See application file for complete search history.

(56) References Cited

U.S. PATENT DOCUMENTS 5,328,955 A * 7/1994 Rhee et al. .................. 525/54.1

OTHER PUBLICATIONS

Venugopal, M.G., et al. 1994 Biochemistry 33(25): 7948-7956.*
Wallace, D.G., et al. 2003 Advanced Drug Delivery Reviews 55: 1631-1649.*
Plant, A.L., et al. Architecture and Application of Biomaterials and Biomolecular Materials 1: 2003 MRS Fall Meeting—Extended Summary, 2004 Edition, Table of Contents: 5 pages total.*
Reyes, C.D., et al. "Engineering integrin-specific surfaces with a triple-helical collagen-mimetic peptide." J Biomed Mater Res A. Jun. 15, 2003;65(4):511-23.
Yu, S.M., et al. "Exploitation of Collagen Mimetic Peptide as a Collagen Adhesive Biopolymer for Novel Biomaterials Development" Materials Research Society Symp. Proc. 2004, vol. EXS-1, pp. 295-299.
International Search Report and the Written Opinion of the International Searching Authority for International Application No. PCT/US05/42813 mailed Jul. 9, 2008.

* cited by examiner

*Primary Examiner* — Marsha Tsay
(74) *Attorney, Agent, or Firm* — Edwards Wildman Palmer LLP; Peter F. Corless; Melissa Hunter-Ensor, Esq.

(57) ABSTRACT

The invention provides modified collagen and related therapeutic and diagnostic methods.

6 Claims, 28 Drawing Sheets

CD thermal melting curves of collagen mimetic peptide derivatives 1~3. The values of Tm (°C) are determined from the temperature at the midpoint of the thermal transition curves.

CD thermal melting curve of CF-Gly$_3$-(PHG)$_6$ (4).

CD thermal melting curve of mPEG$_{2000}$-Gly$_3$-(PHG)$_7$ (5).

Figure 4

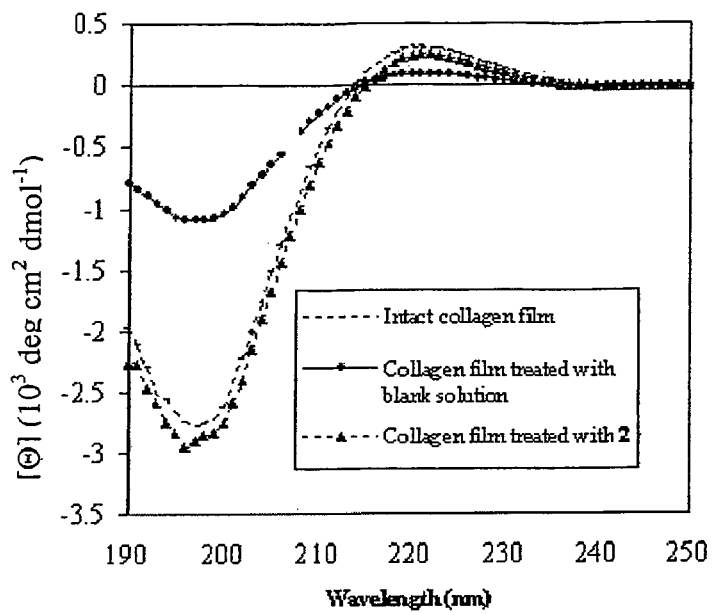

CD measurement of collagen films after the treatment with 2 or blank solution. Both solutions were pre-equilibrated at 80°C before addition to the collagen film. Treatment with blank solution (80°C) unfolded the native collagen and only 32% of collagen's original helical content remains after the treatment. However collagen film treated with 2 retains 80% of its original helical content. The additional helical content is likely due to 2 associating with partially unfolded collagen in the form of triple helix.

*Figure S5.* Transmission electron and fluorescence (inset) micrographs of collagen fibers (type I) after the treatment with 4 at 30°C. The collagen fibers exhibit native banding pattern suggesting that the modification process did not disrupt the native collagen structure. The presence of 4 on the collagen fiber was confirmed by fluorescence microscopy (inset).

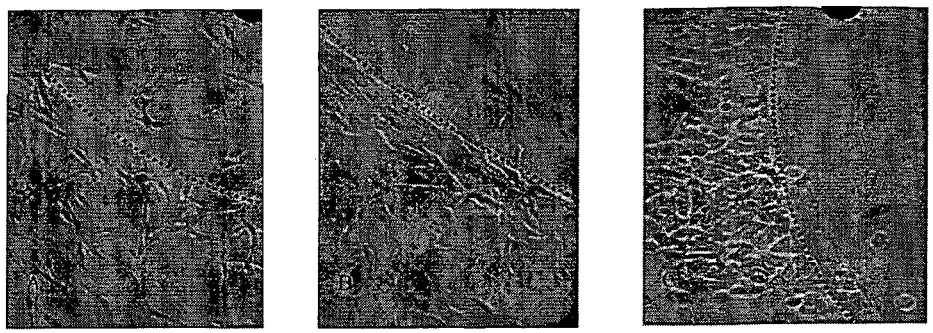
*Figure 7.* Optical micrographs of human fibroblasts (A, B) and breast epithelial cells (C) cultured on collagen films that were pre-treated with mPEG$_{2000}$ (A), or 5 (B and C). Areas of the picture to the right side of dotted lines were treated with mPEG$_{2000}$ or 5.

Figure 8

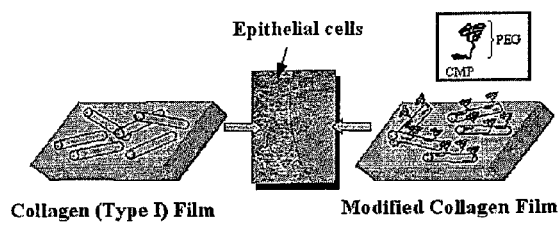

Collagen (Type I) Film     Epithelial cells     Modified Collagen Film

Recent widespread interest in the development of engineered tissue and organ replacement therapies has prompted demand for new approaches to immobilize exogenous components to natural collagen. Chemical coupling of synthetic moieties to amino acid side chains has been commonly practiced for such purposes; however such coupling reactions are difficult to control on large proteins and are generally not conducive to modifying integrated collagen scaffolds that contain live cells and tissues. As an alternative to the conventional "covalent" modification method, we have developed a novel "physical" modification technique that is based on collagen's native ability to associate into a triple-helical molecular architecture. Here we present a finding that collagen mimetic peptides (CMPs) of sequence -(Pro-Hyp-Gly)$_x$- exhibit strong affinity to both native and gelatinized type I collagen under controlled thermal conditions. We also show that the cell adhesion characteristics of collagen can be readily altered by applying a poly(ethyleneglycol)-CMP conjugate to a prefabricated collagen film.

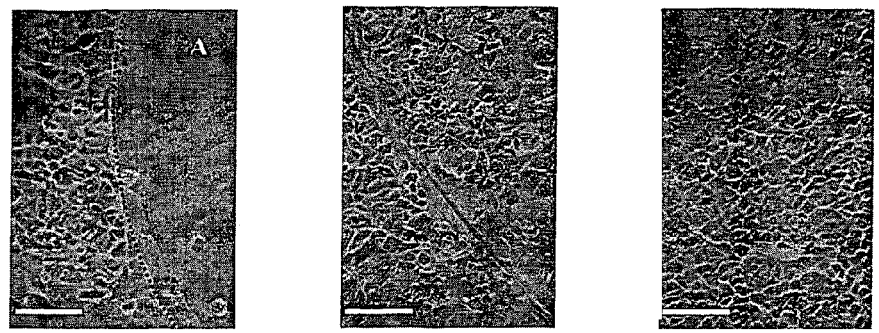
Figures 9A, 9B, and 9C. Optical micrographs of human breast epithelial cells cultured on collagen films that were treated with mPEG$_{2000}$-Gly$_3$-(Pro-Hyp-Gly)$_7$, 3rd day (A), 5th day (B), and 7th day (C). The bar scales represent 100 μm.

Figure 10 Optical micrographs of human breast epithelial cells cultured on collagen films that were treated with (Pro-Hyp-Gly)$_8$-Gly$_3$-PEG$_{5000}$-OH 3rd day (A), 5th day (B), and 7th day (C). The bar scales represent 250 µm.
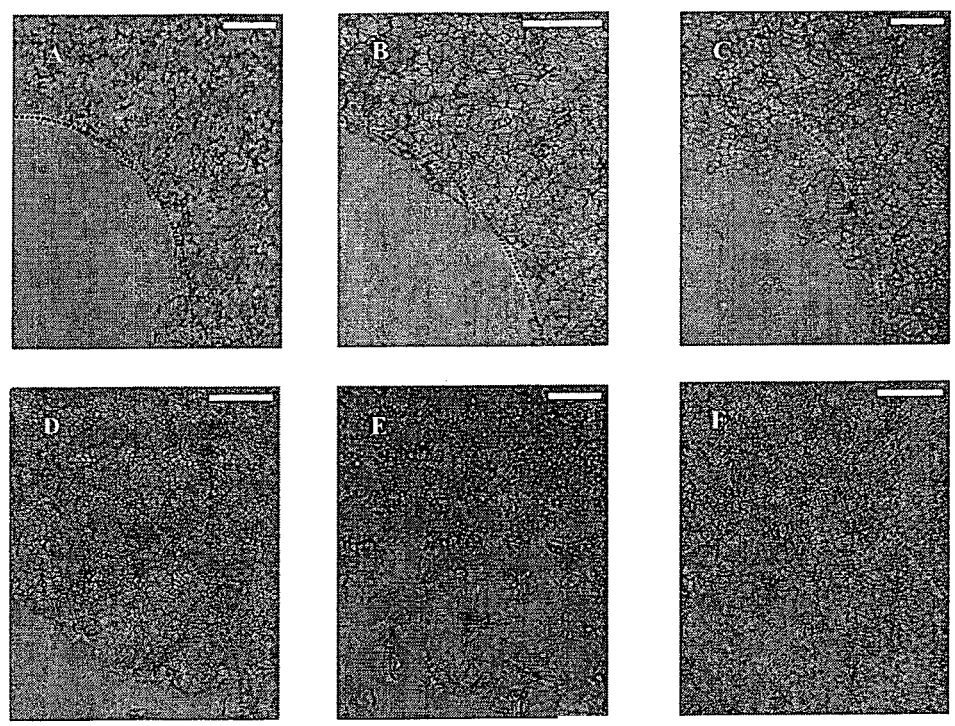

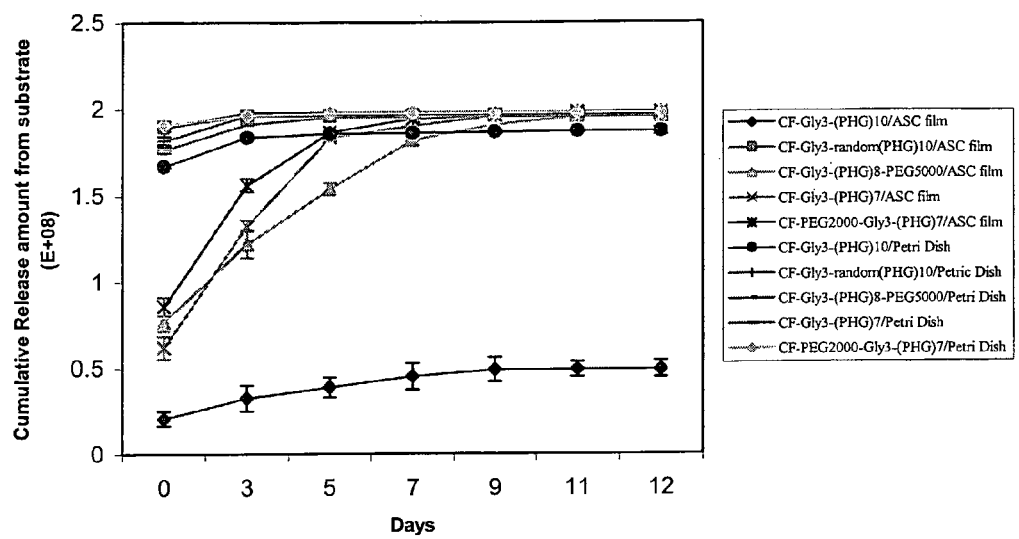
Figure 11. Release study of fluorescence-labeled CMP derivatives from collagen films incubated in PBS buffer solution of pH 7.4 at 37 °C.

Figure 12 is a schematic diagram showing the structure of star shaped, rigid and flexible linear PEG on substrate. The star shaped or suitable linear PEG (PEG5000) explains its highly capacity for repelling approaching molecules or cells compared to flexible linear PEG (PEG20000).
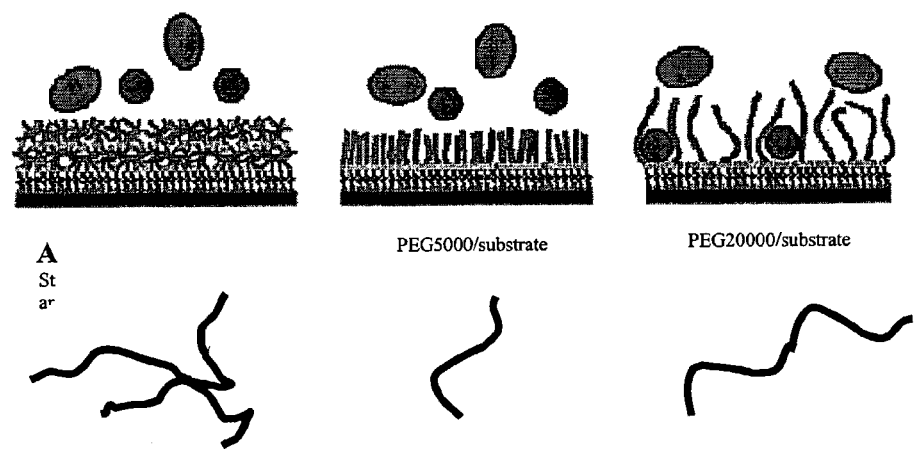

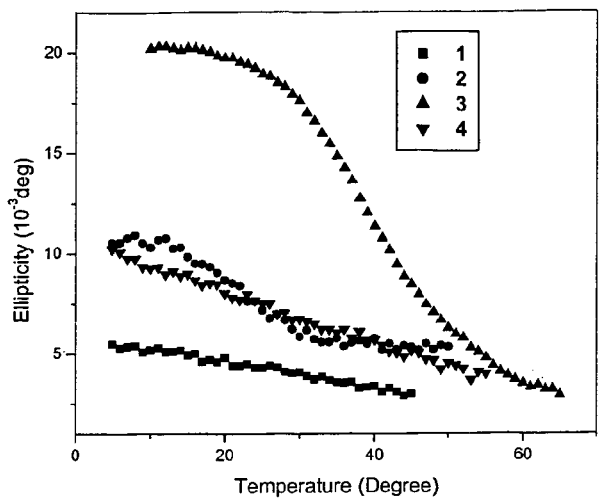
Figure 14. Thermal melting transition curves of 1~4.
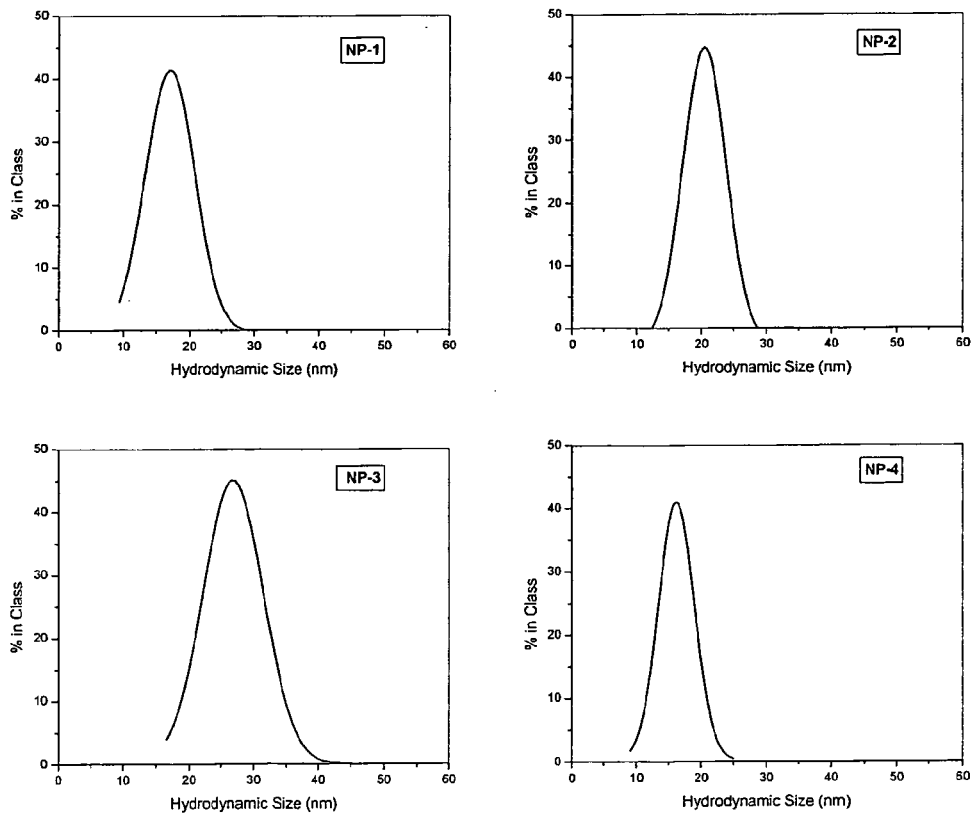
Figure 15. Gaussian fit of the DLS data showing the hydrodynamic size of NP-Xs.

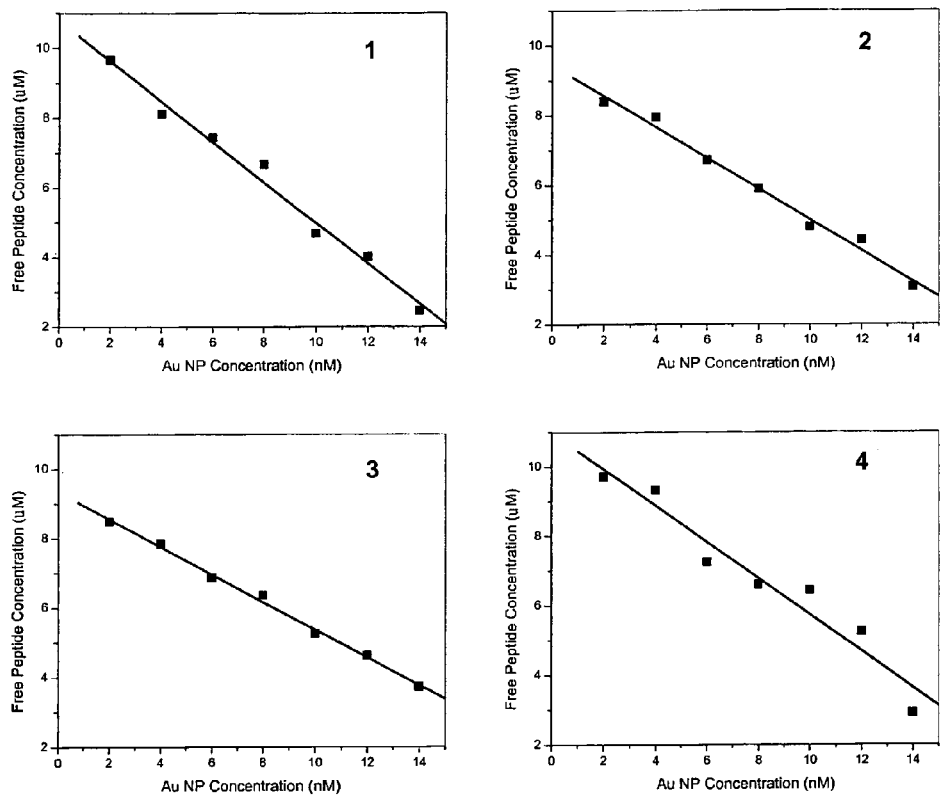
Figure 16 Determination of number of peptides per Au NP.

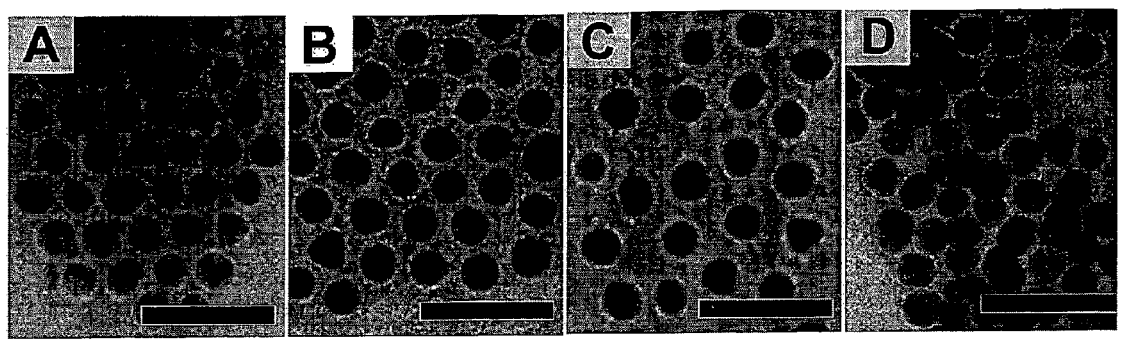
Figure 17. TEM micrographs of negatively stained NP-1 (A), NP-2 (B), NP-3 (C) and unmodified NPs (D). Scale bar = 50 nm.

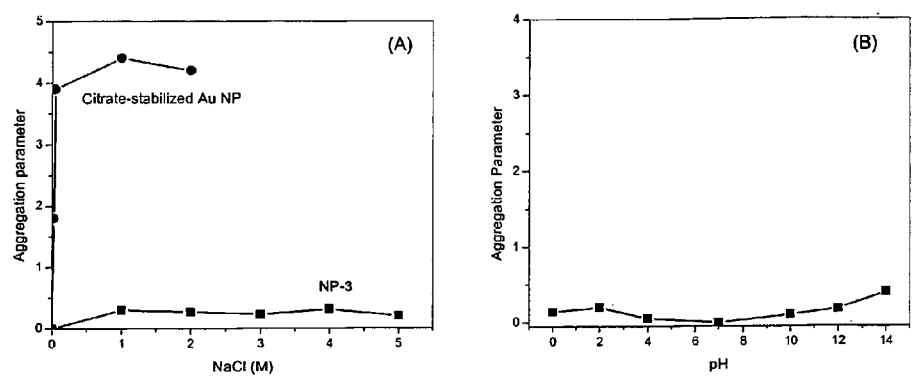
Figure 18. Aggregation parameters of NP-3 at different NaCl concentration (A) and pH (B).

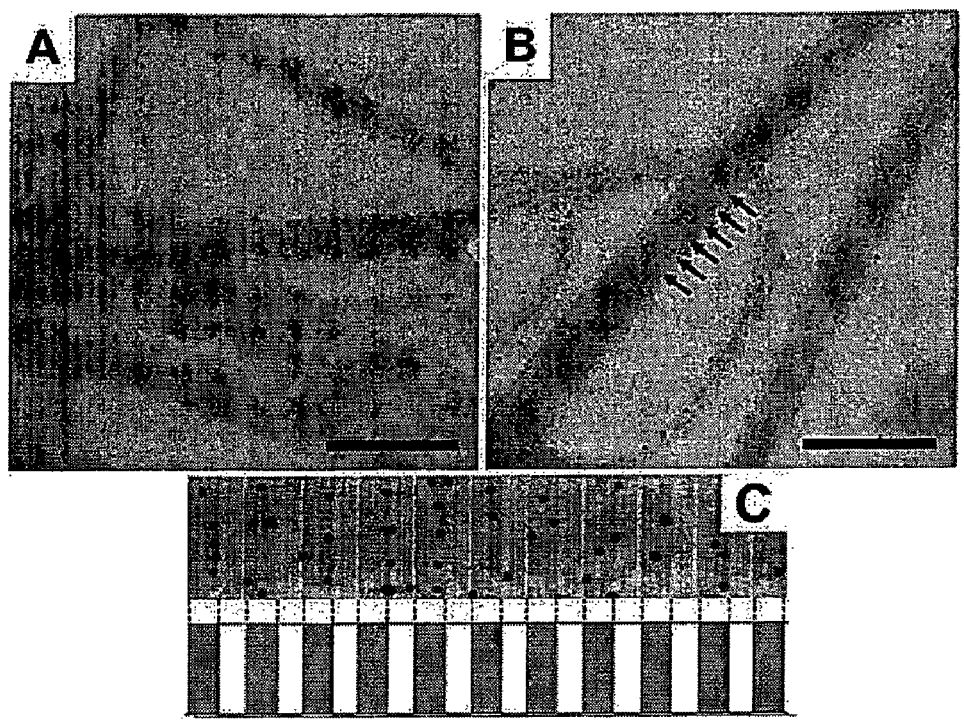
Figure 19. TEM micrographs of reconstituted type I collagen fibers after incubation with NP-4 (A) and NP-3 (B) at 25°C. NP-3 shows preferential affinity to the dark bands of collagen fiber (C). Scale bar = 500 nm.

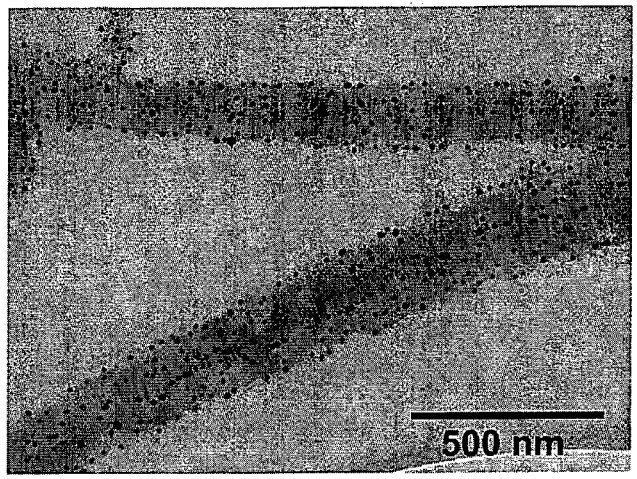
Figure 20. TEM micrograph of NP-3 incubated with reconstituted type I collagen fibers at 40°C.

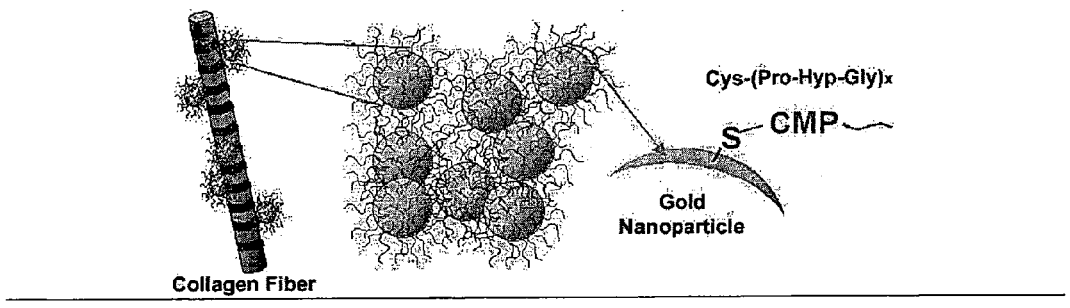

Figure 21 is a schematic diagram. Collagen is the principal tensile element of the extracellular matrix and a fundamental molecular scaffold in a wide range of animal connective tissues. A recent report suggested that the collagen mimetic peptide (CMP) of sequence (Pro-Hyp-Gly)$_x$ binds to type I collagen molecules through a process involving both strand invasion and triple-helix assembly. In effort to visualize this interaction in collagen fibers, we prepared CMP functionalized gold nanoparticles (NPs) as a TEM marker. Here we show that CMP functionalized NPs are highly stable in aqueous solution and exhibit preferential affinity to the gap regions of intact type I collagen fibers. The results indicate that deliberate collagen denaturation is not crucial for the binding of CMPs. CMP's ability to bind to collagen fibers under physiological conditions may have significant implications in understanding the behaviors of collagen-binding proteins that incorporate collagen-like sequences. The CMP functionalized NPs can potentially be used to identify structural abnormalities in collagen fibers that are related to many debilitating human diseases.

Figure 22 Cells are encapsulated in CMP/PEODA hydrogel, and the collagen secreted from the cell binds efficiently to CMP in the hydrogel matrix.
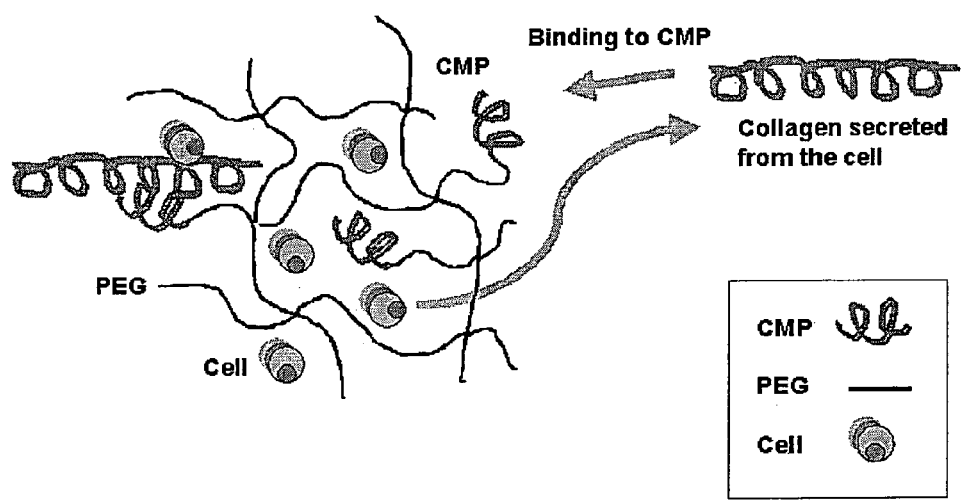

Figure 23 After one week of exogenous collagen encapsulation, hydroxyproline content in each construct was measured (n=3). Controls were selected as PEODA hydrogel alone without modified PEG-CMP.
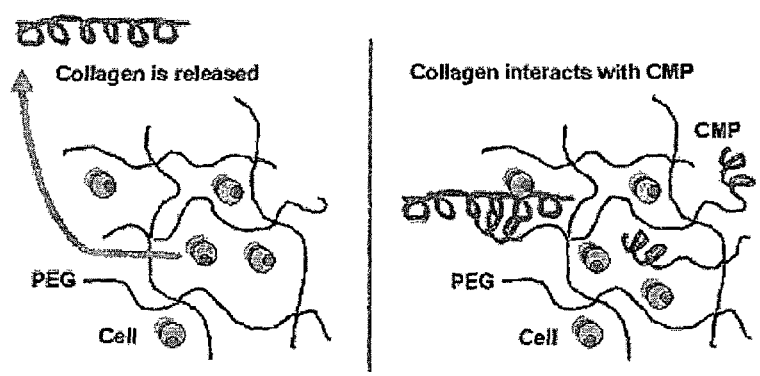
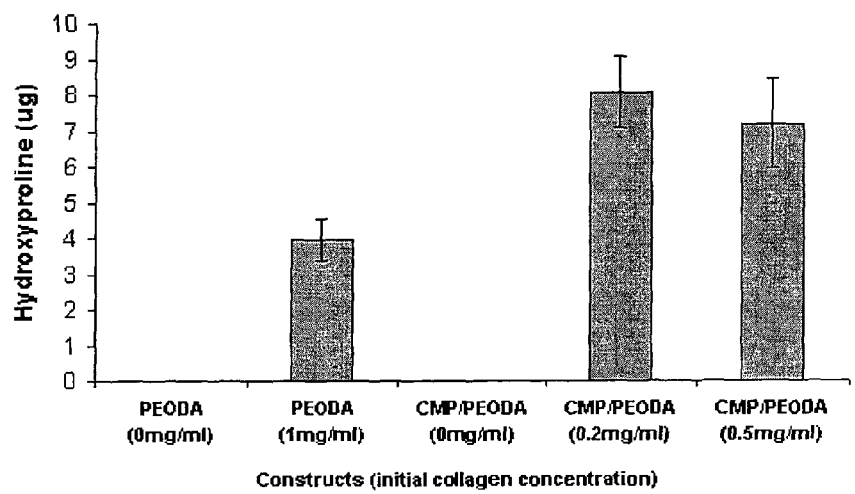

Figure 94. Fluorescence micrograph of chondrocytes encapsulated in 2% CMP/PEODA hydrogels after Live/Dead staining.
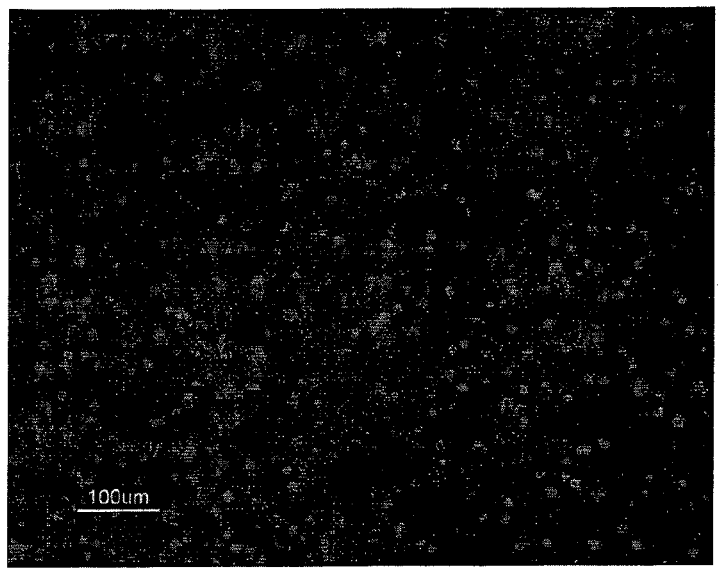

Figure 26 Histological sections were evaluated after 2 weeks of culture. Safranine-O staining for glycosaminoglycan (a, b, and c) and Masson Trichrome staining for collagen (d, e, and f) were used.
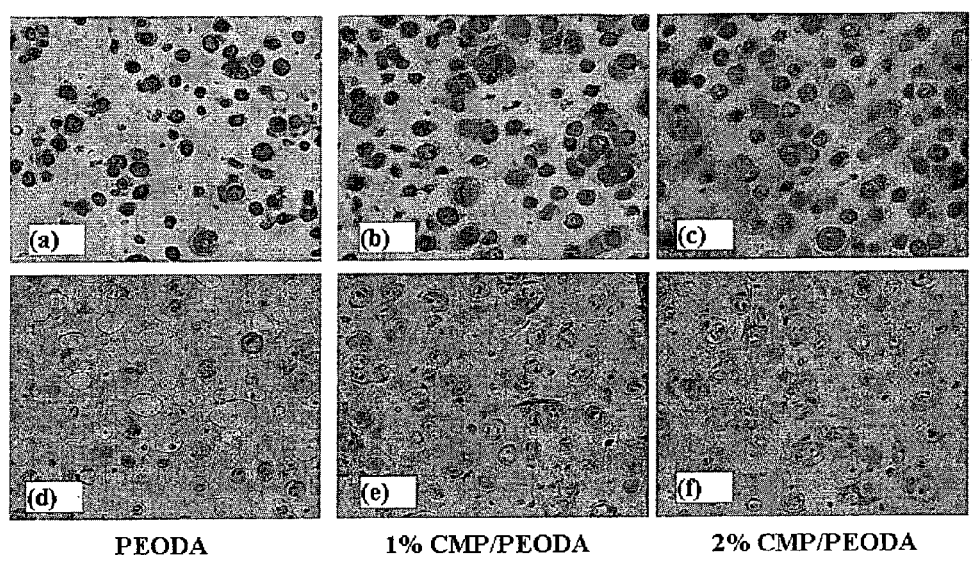

Figure 36 Immunohistochemical staining of paraffin-embedded sections for PEODA control, 1% CMP/PEODA and 2% CMP/PEODA constructs. Antibody for collagen type II was used. Controls showed no staining for antigen (not shown).
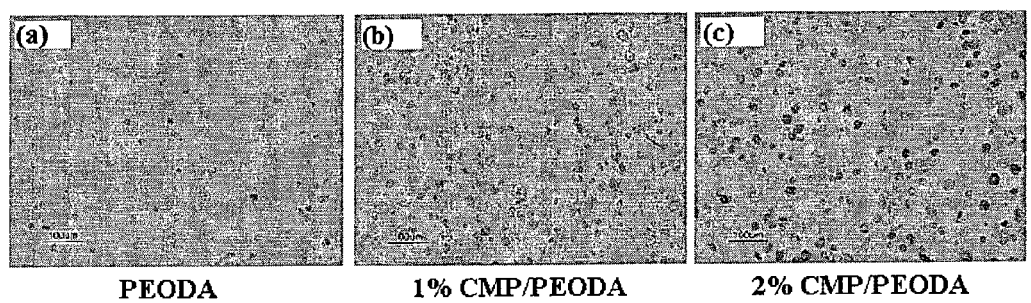
PEODA      1% CMP/PEODA      2% CMP/PEODA Figure 27 Extracellular matrix secretions of chondrocytes were evaluated by biochemical assays (n=3, *: $p<0.05$, : $p<0.0005$, *: $p<0.0001$): (a) Glycosaminoglycan content; (b) Total collagen content. Results were after the background subtraction of collagen content in the acellular CMP hydrogels.
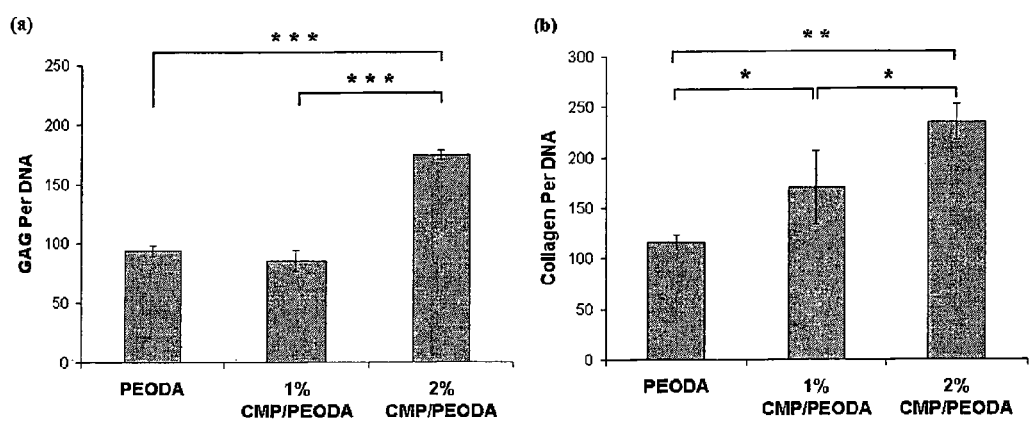

To create a hydrogel with CMP. The monoacrylated PEG-CMP is polymerized with a difunctional PEG to form a hydrogel.

COMPOSITIONS COMPRISING MODIFIED COLLAGEN AND USES THEREFOR

CROSS-REFERENCE TO RELATED APPLICATION

This application claims the benefit of U.S. Provisional Application No. 60/630,271, which was filed on Nov. 23, 2004, and U.S. Provisional Application No. 60/722,079, which was filed on Sep. 29, 2005, each of which is hereby incorporated by reference in its entirety.

STATEMENT OF RIGHTS TO INVENTIONS MADE UNDER FEDERALLY SPONSORED RESEARCH

This work was supported in part by the National Institutes of Health (Grant No. GM-74812) and the National Science Foundation (CTS-0210220). The government may have certain rights in the invention.

SEQUENCE LISTING

The instant application contains a Sequence Listing which has been submitted in ASCII format via EFS-Web and is hereby incorporated by reference in its entirety. Said ASCII copy, created on Mar. 18, 2011, is named 64411US7.txt and is 48,935 bytes in size.

BACKGROUND OF THE INVENTION

Collagen is used in a variety of medical applications ranging from hemostatic materials and biocompatible coatings to drug delivery and tissue engineering. Collagen-based biomaterials are presently used for soft-tissue engineering and repair, and medical products composed of collagen have been approved by the FDA, and are commercially available. These include collagen-based corneal shields, anti-infectious catheters, tissue sealants, hemostatic sponges, and topical wound dressing products. Collagen is also used for tissue engineering substrates targeted for skin, bone, and blood vessel replacement. There is increasing demand for biocompatible and biofunctional materials that feature collagen as a scaffold to support tissue growth, to promote healing, and to develop engineered tissues for organ replacement therapies.

Traditionally, collagen is used as a passive biomaterial that protects injured sites and supports healing processes. Methods for modifying collagen would be useful for the development of materials that can participate in tissue regeneration by actively regulating cell differentiation, proliferation, and tissue organization. Methods for producing modified collagens have focused on chemical modification, that include coupling modifying groups to collagen's amino acid side chains; however, the chemical reactions between exogenous components and collagen molecules are toxic and difficult to control because collagen molecules are large and complex biopolymers. Progress in the area of tissue repair and regeneration requires better methods for conjugating exogenous functionalities to collagen. Desirably, such methods should overcome challenges associated with controlling chemical reactions and chemical toxicity.

SUMMARY OF THE INVENTION

As described below, the present invention features compositions comprising modified collagen and therapeutic and diagnostic methods related to the use of such compositions.

In one aspect, the invention features a method for modifying collagen, the method involving contacting collagen with a collagen mimetic peptide, under conditions that provide for a physical interaction between the collagen and the collagen mimetic peptide.

In another aspect, the invention provides a modified collagen made by the process of the above aspect.

In another aspect, the invention features a collagen mimetic peptide conjugate, where the conjugate is selected from the group consisting of an antibiotic, a cell adhesion molecule, a contrast agent, a detectable label, a growth factor, a component of the extracellular matrix, an anti-inflammatory, a polymer, PEG, and a small molecule. In one embodiment, the collagen mimetic peptide contains a Z-[X-Y-Gly]$_n$ repeat unit (SEQ ID NO: 1), where Z is any amino acid, X is proline or modified proline, Y is proline or modified proline, and n is an integer between 1 and 20, inclusive.

In a related aspect, the invention provides collagen mimetic peptide that contains amino acid sequences Gly$_n$-(Pro-HypGly)$_{n'}$ (SEQ ID NO: 2), (ProHypGly)$_{n'}$-Tyr$_n$ (SEQ ID NO: 3), or Cys$_n$-(Pro-Hyp-Gly)$_{n'}$ (SEQ ID NO: 4) where n is an integer between 1 and 5, and n' is any integer between 1 and 15, and the peptide further comprises a modifier selected from the group consisting of an antibiotic, a cell adhesion molecule, a contrast agent, a detectable label, a growth factor, an anti-inflammatory, a component of the extracellular matrix, a polymer, PEG, and a small molecule. In one embodiment, n' is 5, 6, 7, or 8.

In another aspect, the invention provides a modified collagen containing a CMP mimetic peptide of any previous aspect or made by the process of a previous aspect. In yet another aspect, the invention provides a method of modifying the adhesiveness of a composition, the method involving contacting the composition with a CMP conjugate. In one embodiment, the composition comprises collagen, for example, in a three-dimensional matrix or in a collagen film. In other embodiments, the collagen is modified in a micropattern. In one embodiment, the CMP conjugate is a poly(ethyleneglycol)/CMP conjugate. In another embodiment, modification increases or decreases adhesiveness.

In another aspect, the invention provides a nanoparticle containing a collagen mimetic peptide fixed to the nanoparticle. In one embodiment, the collagen mimetic peptide contains the following sequence Cys$_n$-(Pro-Hyp-Gly)$_{n'}$ (SEQ ID NO: 5), where n is any integer between 1 and 5, and n' is any integer between 1 and 10. In another embodiment, n is 1 and n' is 3. In another embodiment, n' is 5, 6, 7, or 8. In yet another embodiment, the collagen mimetic peptide is fixed to the surface of the nanoparticle. In another embodiment, the nanoparticle is between 5 and 20 nm (e.g., between 10 and 15 nm in diameter). In another embodiment, the nanoparticle is a metal, such as gold (AU).

In another aspect, the transmission electron microscopy marker contains the nanoparticle of any previous aspect. In another embodiment, the nanoparticle comprises AU.

In another aspect, the invention provides a diagnostic marker containing a detectable CMP conjugate, where the marker binds collagen and detects a disease. In one embodiment, CMP is conjugated to a nanoparticle, a detectable label, or a contrast reagent. In another embodiment, the marker detects a disease characterized by disruption of collagen structure. In another embodiment, the marker detects the disease by binding to a collagen selected from the group consisting of collagen type 1-type 29 (e.g., type I, II, III, IV, IX, X, or XI). In one embodiment, the disease is selected from the group consisting of Ehlers-Danlos syndrome, osteogenesis imperfecta, achondrogenesis type 2, hypochondrogenesis, Kniest dysplasia, otospondylomegaepiphyseal dysplasia, spondyloepimetaphyseal dysplasia, Strudwick type, spondyloepiphyseal dysplasia congenita spondyloperipheral dysplasia, Stickler syndrome, and Weissenbacher-Zweymüller. In one embodiment, the marker is detectable using transmission electron microscopy.

In another aspect, the invention provides a method for diagnosing a subject as having or having a propensity to develop a disease characterized by disruption of a collagen structure, the method involving contacting a patient sample with a detectable CMP-conjugate; and detecting an alteration in a collagen structure present in the patient sample, where the alteration diagnoses the subject as having or having a propensity to develop a disease characterized by disruption of a collagen structure.

Zweymüller. In another embodiment, the marker binds a collagen present in a thombosis or a vessel wall.

In another aspect, the invention provides diagnostic kit containing a detectable CMP conjugate and directions for the use of the conjugate in the diagnosis of a disease characterized by a disruption in collagen structure. In one embodiment, the detectable CMP-conjugate binds a collagen selected from the group consisting of collagen type 1-type 29 (e.g., type I, II, III, IX, X, or XI). In another embodiment, the disease is selected from the group consisting of Ehlers-Danlos syndrome, Osteogenesis imperfecta, achondrogenesis type 2, hypochondrogenesis, Kniest dysplasia, otospondylomegaepiphyseal dysplasia, spondyloepimetaphyseal dysplasia, Strudwick type, spondyloepiphyseal dysplasia congenita spondyloperipheral dysplasia, Stickler syndrome, and Weissenbacher-Zweymüller.

In another aspect, the invention provides a composition for repelling cell adhesion, the composition containing a CMP-poly(ethylene glycol) conjugate. In one embodiment, CMP-poly(ethylene glycol) conjugate comprises methoxy-PEG$_{2000}$-Gly$_3$-(Pro-Hyp-Gly)$_7$ (SEQ ID NO: 6) or (Pro-Hyp-Gly)$_9$-Gly$_3$-PEG$_{5000}$ (SEQ ID NO: 7). In another embodiment, CMP-poly(ethylene glycol) conjugate comprises grafted linear PEG or NHS activated star-shaped PEG. In another embodiment, the composition comprises star shaped PEG having the following

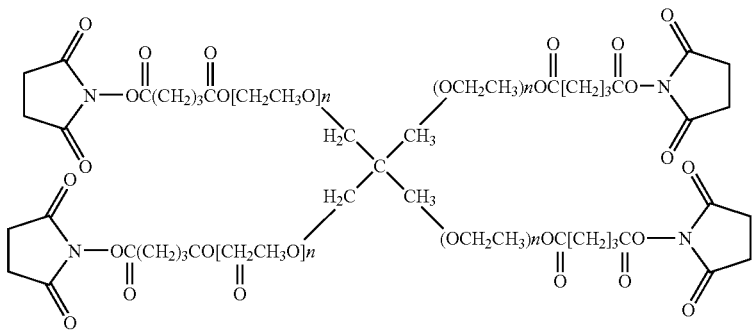

In another aspect, the invention provides a method for diagnosing a subject as having or having a propensity to develop a thrombosis, the method involving contacting a blood vessel with a detectable CMP-conjugate; and detecting an alteration present in the blood vessel, where the alteration diagnoses the subject as having or having a propensity to develop a thrombosis. In one embodiment, the detectable CMP-conjugate binds a collagen selected from the group consisting of collagen type 1-type 29 (e.g., type I, II, III, IV, IX, X, or XI). In another embodiment, the disease is selected from the group consisting of Ehlers-Danlos syndrome, Osteogenesis imperfecta, achondrogenesis type 2, hypochondrogenesis, Kniest dysplasia, otospondylomegaepiphyseal dysplasia, spondyloepimetaphyseal dysplasia, Strudwick type, spondyloepiphyseal dysplasia congenita spondyloperipheral dysplasia, Stickler syndrome, and Weissenbacherformula:
In another embodiment, the composition comprises AcGly-Gly$_2$-Lys-Gly$_3$-(Pro-Hyp-Gly)$_8$ (SEQ ID NO: 8) In another embodiment, the CMP comprises -(Pro-Hyp-Gly)$_{n'}$ (SEQ ID NO: 9), where n is any integer between 1 and 3, and n' is any integer between 1 and 10.

In another aspect, the invention provides matrix containing a CMP-polymer conjugate, where the CMP-polymer conjugate alters the adhesive properties of the matrix. In one embodiment, the CMP-poly(ethylene glycol) conjugate comprises methoxy-PEG$_{2000}$-Gly$_3$-(Pro-Hyp-Gly)$_7$ (SEQ ID NO: 6) or (Pro-Hyp-Gly)$_9$-Gly$_3$-PEG$_{5000}$ (SEQ ID NO: 7). In another embodiment, the CMP-poly(ethylene glycol) conjugate comprises grafted linear PEG. In another embodiment, the composition comprises NHS activated star-shaped PEG. In another embodiment, the composition comprises star shaped PEG star shaped PEG having the following formula:

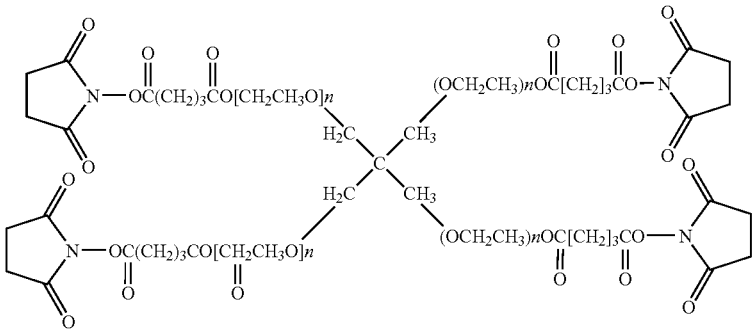

In another embodiment, the composition comprises AcGly-Gly$_2$-Lys-Gly$_3$-(Pro-Hyp-Gly)$_8$ (SEQ ID NO: 8). In another embodiment, the matrix further contains a cell selected from the group consisting of chondrocytes, endothelial cells, dendritic cells, stem cells, multipotent progenitor cells, skin cells, liver cells, heart cells, kidney cells, pancreatic cells, lung cells, bladder cells, stomach cells, intestinal cells, cells of the urogenital tract, breast cells, skeletal muscle cells, skin cells, bone cells, cartilage cells, keratinocytes, hepatocytes, gastrointestinal cells, epithelial cells, endothelial cells, mammary cells, skeletal muscle cells, smooth muscle cells, parenchymal cells, and osteoclasts. In another embodiment, the CMP-poly(ethylene glycol) conjugate is present in a pattern. In yet another embodiment, the CMP comprises -(Pro-Hyp-Gly)$_{n'}$ (SEQ ID NO: 9), where n is any integer between 1 and 3, and n' is any integer between 1 and 10.

In another aspect, the invention provides method for repelling cell adhesion on a composition, the method involving fixing a CMP-PEG conjugate to a composition, where the CMP-PEG conjugate repels cell adhesion on the composition. In one embodiment, the CMP-poly(ethylene glycol) conjugate comprises methoxy-PEG$_{2000}$-Gly$_3$-(Pro-Hyp-Gly)$_7$ (SEQ ID NO: 6) or (Pro-Hyp-Gly)$_9$-Gly$_3$-PEG$_{5000}$ (SEQ ID NO: 7). In another embodiment, the CMP-poly(ethylene glycol) conjugate comprises grafted linear PEG or NHS activated star-shaped PEG. In another embodiment, the method repels adhesion of a cell selected from the group consisting of endothelial cells, dendritic cells, stem cells or other multipotent progenitor cells, skin cells, liver cells, heart cells, kidney cells, pancreatic cells, lung cells, bladder cells, stomach cells, intestinal cells, cells of the urogenital tract, breast cells, skeletal muscle cells, skin cells, bone cells, cartilage cells, keratinocytes, hepatocytes, gastro-intestinal cells, epithelial cells, endothelial cells, mammary cells, skeletal muscle cells, smooth muscle cells, parenchymal cells, osteoclasts, and chondrocytes.

In another aspect, the invention provides composition containing a CMP-poly(ethylene glycol) conjugate that comprises a detectable marker. In one embodiment, CMP-poly (ethylene glycol) conjugate comprises methoxy-PEG$_{2000}$-Gly$_3$-(Pro-Hyp-Gly)$_7$ (SEQ ID NO: 6) or (Pro-Hyp-Gly)$_9$-Gly$_3$-PEG$_{5000}$ (SEQ ID NO: 7). In another embodiment, the CMP-poly(ethylene glycol) conjugate comprises grafted linear PEG, NHS activated star-shaped PEG, or star shaped PEG having the formula shown above.

In yet another embodiment, the composition comprises AcGly-Gly$_2$-Lys-Gly$_3$-(Pro-Hyp-Gly)$_8$ (SEQ ID NO: 8).

In another aspect, the invention provides a method of determining the presence of a CMP-poly(ethylene glycol) conjugate in a composition, the method involving contacting a composition with a CMP-poly(ethylene glycol) conjugate containing a detectable marker; and detecting binding of the CMP-poly(ethylene glycol) conjugate to the composition. In one embodiment, the detecting quantifies the level of detectable marker. In another embodiment, the detecting localizes the detectable marker in the composition.

In another aspect, the invention provides a composition for crosslinking collagen, the composition containing a CMP-poly(ethylene glycol) conjugate. In one embodiment, CMP is conjugated to a multi-armed PEG compound. In another embodiment, PEG comprises an amino group, a thiol group. In one embodiment, the composition comprises star shaped PEG of a Formula shown above. In another embodiment, the composition comprises AcGly-Gly$_2$-Lys-Gly$_3$-(Pro-Hyp-Gly)$_8$ (SEQ ID NO: 8).

In another aspect, the invention provides method for preventing or treating thrombosis in a subject, the method involving contacting a blood vessel having or having a propensity to develop a thrombosis with a CMP-anti-thrombosis conjugate; where the contacting prevents or treats a thrombosis. In one embodiment, the propensity to develop a thrombosis is related to angioplasty. In another aspect, the invention provides the vessel is contacted with a hydrogel containing a CMP-anti-thrombosis conjugate. In another embodiment, the CMP-anti-thrombosis conjugate binds collagen present in the thrombosis. In another embodiment, the CMP-anti-thrombosis conjugate degrades the thrombosis. In another embodiment, the method further involves monitoring the efficacy of the method (e.g., by determining plasma level of β-thromboglobulin or thrombin-antithrombin complexes).

In yet another aspect, the invention provides diagnostic marker that detects a vessel having or having an increased propensity to develop a thrombosis relative to a control vessel, the marker containing a detectable CMP conjugate that binds collagen. In one embodiment, the marker detects the presence of a thrombosis in the vessel. In another embodiment, the marker binds collagen type III. In yet another embodiment, the marker detects a vessel having a propensity to develop a thrombosis.

In another aspect, the invention provides a diagnostic kit containing the diagnostic marker of any previous aspect and directions for the use of the conjugate in the diagnosis of a thrombosis or a propensity to develop a thrombosis.

In another aspect, the invention provides an implantable, sustained release device containing a CMP conjugate fixed to a collagen matrix. In one embodiment, the conjugate is selected from the group consisting of an antibiotic, a growth factor, an anti-inflammatory, a component of the extracellular matrix, and a small molecule. In another embodiment, the antibiotic is selected from the group consisting of penicillin, tetracycline, plectasin, LAH4. In another embodiment, the growth factor is selected from the group consisting of angiogenin, erythropoietin, vascular endothelial growth factor (VEGF), granulocyte/macrophage colony stimulating factor, macrophage-colony stimulating factor, platelet-derived endothelial cell growth factor, and platelet-derived growth factor. In another embodiment, the small molecule is selected from the group consisting of anti-thrombotics, anti-atherosclerosis agents, cartilage repair agent. In one embodiment, the collagen matrix is a hydrogel. In another embodiment, the collagen matrix is a pellet or a film.

In another aspect, the invention provides a kit containing an effective amount of an implantable, sustained release device of a previous aspect, and directions for the use of the device in the treatment of a disease or disorder.

In another aspect, the invention provides a hemostatic sponge containing a collagen mimetic peptide and collagen. In one embodiment, the collagen mimetic peptide physically associates with the collagen. In another embodiment, the sponge further contains a natural or synthetic polymer. In another embodiment, the collagen mimetic peptide further comprises a conjugate selected from the group consisting of clotting agents, growth factors, and antibiotics. In another embodiment, the clotting agents is the group selected from the group consisting of thrombin and fibrin.

In another aspect, the invention provides a corneal shield containing a collagen mimetic peptide conjugate and a polymer. In one embodiment, the CMP conjugate comprises an antibiotic, an anti-inflammatory, or a small molecule.

In another aspect, the invention provides a wound healing device containing a collagen mimetic peptide conjugate and a polymer. In one embodiment, the CMP conjugate comprises an antibiotic, a cell adhesion molecule, a growth factor, a component of the extracellular matrix, an anti-inflammatory, and a small molecule. In another embodiment, the device is in the form of a plug, mesh, strip, suture, dressing, patch, threads, suture, or biological fastener. In other embodiments, the device further contains a cell selected from the group consisting of endothelial cells, dendritic cells, stem cells or other multipotent progenitor cells, skin cells, liver cells, heart cells, kidney cells, pancreatic cells, lung cells, bladder cells, stomach cells, intestinal cells, cells of the urogenital tract, breast cells, skeletal muscle cells, skin cells, bone cells, cartilage cells, keratinocytes, hepatocytes, gastro-intestinal cells, epithelial cells, endothelial cells, mammary cells, skeletal muscle cells, smooth muscle cells, parenchymal cells, osteoclasts, and chondrocytes.

In another aspect, the invention provides a kit containing the wound healing device of any previous aspect.

In another aspect, the invention provides matrix containing a polymer in association with a collagen mimetic peptide, where the matrix promotes the survival, differentiation, or proliferation of a cell. In one embodiment, the polymer is in a hydrogel, is biochemically inert, or is photopolymerizable. In another embodiment, the polymer is collagen, poly(ethylene oxide) diacrylate (PEODA), poly(ethylene glycol), polyvinyl alcohol, or polyacrylic acid. In one embodiment, the physical interaction occurs by helical assembly or strand invasion. In another embodiment, collagen mimetic peptide conjugate (e.g., a conjugate containing a reactive group, such as an acrylate group (e.g., PEG mono- or diacrylate)) acts as a cross-linking agent. In another embodiment, the matrix is susceptible to proteolytic breakdown. In another embodiment, the matrix further comprises an antibiotic, a cell adhesion molecule, a contrast agent, a detectable label, a growth factor, a component of the extracellular matrix, an anti-inflammatory, a polymer, PEG, and a small molecule. In another embodiment, CMP is conjugated to an antibiotic, a cell adhesion molecule, a growth factor, a component of the extracellular matrix, an anti-inflammatory, a polymer, PEG, and a small molecule.

In other embodiment of the above aspects, PEG is star shaped PEG, a multi-armed PEG, a graft linear PEG, $PEG_{2000}$, or $PEG_{5000}$. In still other embodiments of the above aspects, the matrix further contains a cell selected from the group consisting of endothelial cells, dendritic cells, stem cells or other multipotent progenitor cells, skin cells, liver cells, heart cells, kidney cells, pancreatic cells, lung cells, bladder cells, stomach cells, intestinal cells, cells of the urogenital tract, breast cells, skeletal muscle cells, skin cells, bone cells, cartilage cells, keratinocytes, hepatocytes, gastrointestinal cells, epithelial cells, endothelial cells, mammary cells, skeletal muscle cells, smooth muscle cells, parenchymal cells, osteoclasts, and chondrocytes.

In another aspect, the invention provides a method for synthesizing a matrix, the method involving contacting a collagen mimetic peptide to a polymer and cross-linking the polymer such that a molecular matrix is formed. In one embodiment, the polymer is in a hydrogel, is biochemically inert, or is photopolymerizable. In another embodiment, the polymer is selected from the group consisting of poly(ethylene glycol), poly(ethylene oxide) diacrylate (PEODA), polyvinyl alcohol, or polyacrylic acid.

In another aspect, the invention provides a method for promoting cell survival or proliferation, involving growing a cell in contact with a matrix containing a polymer and a collagen mimetic peptide. In one embodiment, the collagen mimetic peptide is capable of retaining a cell-secreted collagen. In another embodiment, the matrix further comprises an antibiotic, a cell adhesion molecule, a contrast agent, a detectable label, a growth factor, a component of the extracellular matrix, an anti-inflammatory, a polymer, PEG, and a small molecule. In another embodiment, the CMP is conjugated to an antibiotic, a cell adhesion molecule, a growth factor, a component of the extracellular matrix, an anti-inflammatory, a polymer, PEG, and a small molecule. In another embodiment, the polymer is in a hydrogel, is biochemically inert, or is photopolymerizable. In another embodiment, the cell is selected from the group consisting of endothelial cells, dendritic cells, stem cells or other multipotent progenitor cells, skin cells, liver cells, heart cells, kidney cells, pancreatic cells, lung cells, bladder cells, stomach cells, intestinal cells, cells of the urogenital tract, breast cells, skeletal muscle cells, skin cells, bone cells, cartilage cells, keratinocytes, hepatocytes, gastro-intestinal cells, epithelial cells, endothelial cells, mammary cells, skeletal muscle cells, smooth muscle cells, parenchymal cells, osteoclasts, and chondrocytes.

In yet another aspect, the invention provides a method for replacing a damaged or absent tissue, the method involving growing a cell in a matrix of any one of a previous aspect; and contacting a damaged tissue or site of an absent tissue with the cell and matrix, such that the cell and matrix replaces the damaged or absent tissue.

In yet another aspect, the invention provides a method for or for tissue augmentation, the method involving growing a cell in a matrix of a previous aspect; and contacting a tissue that requires augmentation with the cell and matrix, such that the cell and matrix augments the tissue.

In various embodiments of the above aspects, the cell is derived from or the tissue is selected from any one or more of muscle, cartilage, heart, bladder, brain, nervous tissue, glial tissue, esophagus, fallopian tube, heart, pancreas, intestines, gallbladder, kidney, liver, lung, ovaries, prostate, spinal cord, spleen, stomach, testes, thymus, thyroid, trachea, urogenital tract, ureter, urethra, uterus, breast, skeletal muscle, skin, bone, and cartilage. In still other embodiments of the above aspects, the cell is any one or more of endothelial cells, dendritic cells, stem cells, multipotent progenitor cells, skin cells, liver cells, heart cells, kidney cells, pancreatic cells, lung cells, bladder cells, stomach cells, intestinal cells, cells of the urogenital tract, breast cells, skeletal muscle cells, skin cells, bone cells, cartilage cells, keratinocytes, hepatocytes, gastro-intestinal cells, epithelial cells, endothelial cells, mammary cells, skeletal muscle cells, smooth muscle cells, parenchymal cells, adipocytes, osteoclasts, and chondrocytes. In another embodiment, the method is useful for cosmetic surgery. In another embodiment, the method reconstructs a breast, a face, or a body part after cancer surgery or trauma.

In yet another aspect, the invention provides a method for promoting cartilage repair, the method involving growing a chondrocyte in a matrix of a previous aspect; and contacting cartilage with the chondrocyte and matrix, where the contact promotes cartilage repair.

In various embodiments of any of the above aspects, the collagen mimetic peptide or collagen mimetic peptide conjugate comprises a Z-[X-Y-Gly]$_n$ repeat unit (SEQ ID NO: 1), where Z is any amino acid, X is proline or modified praline (e.g., 4-hydroxyl proline, 4-fluoro praline), Y is proline or modified proline (e.g., 4-hydroxyl proline, 4-fluoro praline), and n is an integer between 1 and 20. In other embodiments of any of the above aspects, the collagen mimetic peptide comprises (ProHypGly)$_x$ (SEQ ID NO: 10), (ProProGly)$_x$ (SEQ ID NO: 11), or (ProFlpGly)$_x$ (SEQ ID NO: 12), where Hyp is hydroxyl proline, Flp is 4-fluoro proline, and x is any integer between 1 and 30 (e.g., 1, 2, 3, 4, 5, 6, 7, 8, 9, 10, 11, 12, 13, 14, 15, 16, 20, 25, 30). In yet other embodiments of any of the above aspects, the collagen mimetic peptide comprises at least 5, 10, 15, 20, 25, 30, 40, or 50 amino acids. In still other embodiments of any of the above aspects, the collagen mimetic peptide is conjugated to an antibiotic (e.g., penicillin, tetracycline, plectasin, LAH4), a cell adhesion molecule (e.g., cadherin, fibronectin, integrin, laminin, selectin), a contrast agent (e.g., a gadolinium complex, gadodiamide derivative, ferric ammonium citrate, and mangafodipar trisodium), a detectable label (e.g., a colloidal particle, an enzyme, an electron-dense reagent, a fluorescent dye, a hapten, an immunogen, a magnetic bead, a radiolabel, carboxy-fluorescein), a growth factor that promotes angiogenesis, cell growth, differentiation, proliferation, neurogenesis, osteogenesis, stem cell renewal, or cell survival, such as angiogenin, erythropoietin, vascular endothelial growth factor (VEGF), granulocyte/macrophage colony stimulating factor, macrophage-colony stimulating factor, platelet-derived endothelial cell growth factor, or platelet-derived growth factor, a component of the extracellular matrix (e.g., collagen, elastin, fibrillin, fibronectin, laminin; proteoglycans, hyaluronan, chondroitin sulfate, dermatan sulfate, heparan sulfate, heparin, keratan sulfate, and aggrecan), an anti-inflammatory (e.g., corticosteroids, NSAIDS), a polymer (e.g., collagen, poly(ethylene oxide) diacrylate (PEODA), poly(ethylene glycol) (PEG) (e.g., a star shaped PEG, a multi-armed PEG, a graft linear PEG, PEG$_{2000}$, and PEG$_{5000}$), and a small molecule, such as an anti-thrombotics (e.g., heparin-CMP, Hirudin-CMP, Saratin-CMP), atherosclerosis therapeutic (e.g., cholestyramine, colestipol, nicotinic acid, gemfibrozil, probucol, atorvastatin, lovastatin), a cartilage repair agent (e.g., chondroitan sulfate). In various embodiments, the collagen mimetic peptide binds to any one or more collagen selected from the group consisting of type 1-29 collagen, such as type I, II, III, IV, IX, X, or XI. In yet other embodiments of the above aspects, collagen mimetic peptide peptide comprises an amino acid sequence selected from the group consisting of Gly$_3$-(ProHypGly)$_6$ (SEQ ID NO: 13), Gly$_3$-(ProHypGly)$_7$ (SEQ ID NO: 14), Gly$_3$-(ProHypGly)$_8$ (SEQ ID NO: 15), Gly$_3$-(ProHypGly)$_9$ (SEQ ID NO: 16), (ProHypGly)$_6$-Tyr (SEQ ID NO: 17) (Pro-HypGly)-7-Tyr (SEQ ID NO: 18), (ProHypGly)-8-Tyr (SEQ ID NO: 19), Cys-(Pro-Hyp-Gly)$_3$ (SEQ ID NO: 20), Cys-(Pro-Hyp-Gly)$_5$ (SEQ ID NO: 21), and Cys-(Pro-Hyp-Gly)$_7$ (SEQ ID NO: 22), $_{carboxyfluorescein}$-Gly$_3$-(Pro-Hyp-Gly)$_6$ (SEQ ID NO: 23) carboxyfluorescein-Gly$_3$-lys-(Pro-Hyp-Gly)$_8$ (SEQ ID NO: 24) PEG$_{2000}$-Gly$_3$-(Pro-Hyp-Gly)$_7$ (SEQ ID NO: 25), Methoxy PEG$_{2000}$-Gly$_3$-(Pro-Hyp-Gly)$_7$ (SEQ ID NO: 6), (Pro-Hyp-Gly)$_8$-Gly$_3$-PEG$_{5000}$-OH (SEQ ID NO: 26), [AcGly-Gly$_2$-Lys-Gly$_3$-(Pro-Hyp-Gly)$_8$]$_4$-star shaped PEG (core sequence disclosed as SEQ ID NO: 27), [CF-Gly$_3$-Lys-Gly$_3$-(Pro-Hyp-Gly)$_8$]$_4$-star shaped PEG (core sequence disclosed as SEQ ID NO: 28), AcGly-Gly$_2$-Lys-Gly$_3$-(Pro-Hyp-Gly)$_8$ (SEQ ID NO: 29), FL-PEG$_{2000}$-Gly$_3$-(Pro-Hyp-Gly)$_7$ (SEQ ID NO: 30), and 5 carboxyfluorescein -Gly$_3$-(Pro-Hyp-Gly)$_8$-Gly$_3$-PEG$_{5000}$-OH (SEQ ID NO: 31). In various embodiments of the above aspects, the peptide has a melting transition temperature between 5° C. and 95° C. (e.g., between 10° C. and 80° C., 15° C. and 40° C., 20° C. and 37° C.). In various embodiments of the above aspects, CMP is conjugated to a multi-armed PEG compound. In other embodiment, PEG comprises an amino group, a thiol group, is monoacrylated, or is diacrylated. In yet other embodiments of any of the above aspects, CMP is conjugated to a clotting agent, such as thrombin or fibrin. In yet other embodiments of the above aspects, the polymer is collagen, poly(ethylene oxide) diacrylate (PEODA), poly(ethylene glycol), polyvinyl alcohol, or polyacrylic acid. In still other embodiments of the above aspects, the CMP physically interacts or binds collagen. In other embodiments, the physical interaction occurs by helical assembly or strand invasion. In still other embodiments of the above aspects the collagen mimetic peptide conjugate (e.g., a conjugate containing a reactive group, such as an acrylate group (e.g., PEG mono- or diacrylate)) acts as a cross-linking agent. In still other embodiments of any of the above aspects, the polymer is in a hydrogel, is biochemically inert, or is photopolymerizable By "collagen" is meant a protein component of an extracellular matrix having a tertiary structure that includes polypeptide chains intertwining to form a collagen triple helix or having a characteristic amino acid composition comprising Gly-X-Y repeat units, or a fragment thereof. Collagens useful in the methods of the invention include any collagen known in the art (e.g., one of collagen type 1-29).

By "collagen mimetic peptide" (CMP) is meant a peptide that is able to form a collagen triple helical structure and physically interacts with a collagen polypeptide. In general a CMP has an amino acid sequence comprising -[X-Y-Gly]$_n$ repeat units. In general a CMP binds collagen with high affinity.

A "collagen mimetic peptide conjugate" is a CMP covalently bound to another molecule. Molecules capable of acting as CMP conjugates include, but are not limited to, polypeptides, or fragments thereof, nucleic acid molecules, small molecule compounds, detectable labels, nanoparticles, and polymers.

By "ameliorate" is meant decrease, suppress, attenuate, diminish, arrest, or stabilize the development or progression of a disease.

By "alteration" is meant a change (increase or decrease) in the expression levels of a gene or polypeptide as detected by standard art known methods such as those described above. As used herein, an alteration includes a 10% change in expression levels, preferably a 25% change, more preferably a 40% change, and most preferably a 50% or greater change in expression levels."

"Biological sample" as used herein refers to a sample obtained from a biological subject, including sample of biological tissue or fluid origin, obtained, reached, or collected in vivo or in situ, that contains or is suspected of containing nucleic acids or polypeptides. Such samples can be, but are not limited to, organs, tissues, fractions and cells isolated from mammals including, humans such as a patient, mice, and rats. Biological samples also may include sections of the biological sample including tissues, for example, frozen sections taken for histologic purposes.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ.

By "an effective amount" is meant the amount required to ameliorate the symptoms of a disease relative in an untreated patient. The effective amount of active compound(s) used to practice the present invention for therapeutic treatment of a neurodegenerative disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "immunological assay" is meant an assay that relies on an immunological reaction, for example, antibody binding to an antigen. Examples of immunological assays include ELISAs, Western blots, immunoprecipitations, and other assays known to the skilled artisan.

By "polymer" is meant a natural or synthetic organic molecule formed by combining smaller molecules in a regular pattern.

By "small molecule" is meant any chemical compound.

By "modulation" is meant any alteration (e.g., increase or decrease) in a biological function or activity.

By "nanoparticle" is meant an aggregate of anywhere from a few hundred to tens of thousands of atoms that have a diameter ranging from 3-300 nanometers.

By "matrix" is meant a substance that fills the spaces between isolated cells in culture. For some applications, a matrix is an adhesive substrate used to coat a glass or plastic surface prior to cell culture.

By "repelling cell adhesion" is meant decreasing an adhesive characteristic of a composition relative to an untreated composition.

By "reference" is meant a standard or control condition.

By "subject" is meant a mammal, including, but not limited to, a human or non-human mammal, such as a bovine, equine, canine, ovine, or feline.

By "physical interaction" is meant an association that does not require covalent bonding. In one embodiment, a physical interaction includes incorporation into a helical structure.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The invention provides modified collagen and related therapeutic methods. Other features and advantages of the invention will be apparent from the detailed description, and from the claims.

BRIEF DESCRIPTION OF THE DRAWINGS

FIG. 4 shows a CD measurement of collagen films after the treatment with peptide 2 or blank solution. Both solutions were pre-equilibrated at 80° C. before addition to the collagen film. Treatment with blank solution (80° C.) unfolded the native collagen and only 32% of collagen's original helical content remains after the treatment. However collagen film treated with peptide 2 retains 80% of its original helical content. The additional helical content is likely due to peptide 2 associating with partially unfolded collagen in the form of triple helix.

FIG. 5A shows the binding of peptide 2 and control samples to collagen (groups a and b) and gelatin (group c) films (SEQ ID NOS 37-38, respectively, in order of appearance). The gelatin film was prepared by subjecting the collagen film to heat (80° C.) for 30 minutes. FIG. 5B shows the binding of peptide 4 (SEQ ID NO: 39) to collagen films.

FIGS. 7A, 7B and 7C are optical micrographs of human fibroblasts (FIGS. 7A and 7B) and breast epithelial cells (FIG. 7C) cultured on collagen films that were pre-treated with mPEG$_{2000}$ (FIG. 7A), or peptide 5 (FIGS. 7B and 7C). Areas of the picture to the right side of the dotted lines were treated with mPEG$_{2000}$ or peptide 5.

FIG. 8 is a schematic diagram showing methods for altering the growth of epithelial cells on a collagen gel using modified CMP conjugated to PEG.

FIGS. 9A-9C are optical micrographs of human breast epithelial cells cultured on collagen films that were treated with mPEG$_{2000}$-Gly$_3$-(Pro-Hyp-Gly), (SEQ ID NO: 6) 3rd day (FIG. 9A), 5th day (FIG. 9B), and 7th day (FIG. 9C). The bar scales represent 100 µm.

FIGS. 10A-10F are optical micrographs of human breast epithelial cells cultured on collagen films that were treated with (Pro-Hyp-Gly)$_8$-Gly$_3$-PEG$_{5000}$-OH (SEQ ID NO: 26) 3rd day (A), 5th day (B), and 7th day (C), or longer 10D-10F. The bar scales represent 250 µm.

FIG. 11 is a graph that quantitates the release of fluorescence-labeled CMP derivatives from collagen films incubated in PBS buffer solution of pH 7.4 at 37° C. FIG. 11 discloses SEQ ID NOS 46-49 and 46-49, respectively, in order of appearance.

FIG. 12 is a schematic diagram showing the structure of star shaped, rigid and flexible linear PEG on substrate. The structure of star shaped or suitable linear PEG (PEG5000) explains its capacity for repelling approaching molecules or cells compared to flexible linear PEG (PEG20000).

FIG. 14 shows the thermal melting transition curves for peptides 1'–4'.

FIG. 15 shows the Gaussian fit of the dynamic light scattering (DLS) data showing the hydrodynamic size of nanoparticle-peptide number (NP-Xs).

FIG. 16 shows the determination of the number of peptides per Au NP.

FIGS. 17A-17D are transmission electron microscope (TEM) micrographs of negatively stained NP-1 (FIG. 17A), NP-2 (FIG. 17B), NP-3 (FIG. 17C) and unmodified NPs (FIG. 17D). Scale bar=50 nm FIGS. 18A and 18B show the aggregation parameters of NP-3 at different NaCl concentration (FIG. 18A) and pH (FIG. 18B).

FIGS. 19A-19C show TEM micrographs of reconstituted type I collagen fibers after incubation with NP-4 (FIG. 19A) and NP-3 (FIG. 19B) at 25° C. NP-3 shows preferential affinity to the dark bands of collagen fiber (FIG. 19C). Scale bar=500 nm.

FIG. 20 shows a TEM micrograph of NP-3 incubated with reconstituted type I collagen fibers at 40° C.

FIG. 21 is a schematic diagram showing the general approach used for collagen mimetic peptide (CMP) functionalized gold nanoparticle (NPs) use. CMP functionalized NPs are highly stable in aqueous solution and exhibit preferential affinity to the gap regions of intact type I collagen fibers. CMP functionalized NPs are used to identify structural abnormalities in collagen fibers that are related to many debilitating human diseases. FIG. 21 discloses SEQ ID NO: 50.

FIG. 22 is a schematic diagram showing a CMP/poly(ethylene oxide) diacrylate (PEODA) hydrogel containing cells. The collagen secreted from the cell binds efficiently to the CMP present in the hydrogel matrix.

FIGS. 23A and 23B show the effects of CMP on collagen retention. FIG. 23A is a schematic diagram showing that cell-secreted collagen is more effectively retained by hydrogels that include CMP (right panel) than by hydrogels lacking CMP (left panel). FIG. 23B is a graph showing hydroxyproline content measured (n=3) in a hydrogel following one week of cell culture. Controls were as PEODA hydrogel alone without modified PEG-CMP.

FIG. 24 is a fluorescence micrograph of chondrocytes encapsulated in 2% CMP/PEODA hydrogels after Live/Dead staining.

FIGS. 25A-25F are micrographs of chondrocytes cultured in PEODA, 1% CMP/PEODA, and 2% CMP/PEODA matrices. Histological sections were evaluated after 2 weeks of culture. Safranine-O staining for glycosaminoglycan (FIG. 25A, 25B, and 25C) and Masson Trichrome staining for collagen (FIG. 25D, 26E, and 26F) were used.

FIGS. 26A-26C are micrographs showing immunohistochemical staining of chondrocytes cultured in matrices containing PEODA control, 1% CMP/PEODA, and 2% CMP/PEODA. Antibody for collagen type H was used. Controls showed no staining for antigen.

FIGS. 27A and 27B are graphs showing the quantitation of extracellular matrix secretions of chondrocytes as evaluated by biochemical assays (n=3, *: p<0.05, : p<0.0005, *: p<0.0001): for glycosaminoglycan content (FIG. 27A); or total collagen content (FIG. 27B). Background levels of collagen content present in the acellular CMP hydrogels was subtracted from these totals.

DETAILED DESCRIPTION OF THE INVENTION

Figure 1:
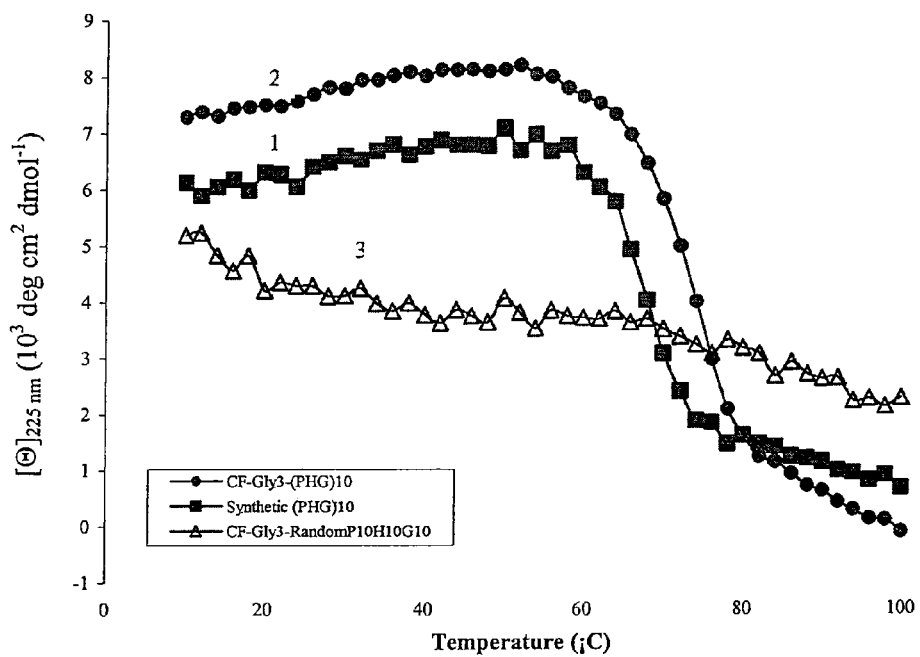
FIG. 1 shows circular dichroism (CD) thermal melting curves of collagen mimetic peptide derivatives 1~3 (SEQ ID NOS 37, 36 and 38, respectively, in order of appearance). The values of Tm (° C.) are determined from the temperature at the midpoint of the thermal transition curves.

The invention features compositions comprising modified collagen and related therapeutic and diagnostic methods. In contrast with previous methods, which typically rely on chemical modifications, particularly covalent modifications, the methods described herein provide for the physical modification of collagen. This invention is based, in part, on the discovery that collagen mimetic peptides (CMPs) of sequence -(Pro-Hyp-Gly)$_x$- exhibited strong affinity for collagen. In addition, the invention provides for the modulation of the cell adhesion characteristics of collagen by contacting a poly(ethyleneglycol)-CMP conjugate with collagen.

Collagen

Collagen is the most abundant structural protein in the body, existing as the foremost component of the extracellular matrix (ECM). Most types of collagen contain a unique tertiary structure that includes three individual right-handed helical polypeptide chains intertwining to form a left-handed helix. Collagen has a characteristic amino acid composition comprised of Gly-X-Y repeat units, where 28% of the X positions consist of proline (Pro) and 38% of the Y positions consist of post-translationally modified 4-hydroxyproline residues (Hyp). The triple-helical structure can be denatured upon heating above its melting temperature[1]. Collagen mimetic peptides (CMPs) with Gly-X-Y sequences have been used to analyze collagen. CMPs based on Pro-Pro-Gly and Pro-Hyp-Gly trimers have been widely studied, and their collagen-like triple helical structure and melting behaviors have been charaterized[2-8]. Unlike collagen, CMPs exhibit reversible melting behavior due to their small size. When denatured collagen is cooled, it regains only about 5-10% of its original triple helical content, and the remainder turns into gelatin. In contrast, CMP regains almost 100% of its original triple helical structure after denaturation.

Collagen is used in a variety of medical applications including hemostatic materials, biocompatible coatings, drug delivery and tissue engineering. Collagen-based biomaterials are also used in soft-tissue engineering and repair. In the past two decades, a multitude of medical products composed of collagen have been approved by the FDA, and many are available as commercial products[9], including collagen-based corneal shields, anti-infectious catheters, tissue sealants, hemostatic sponges, and topical wound dressing products. Collagen is also used as a tissue engineering substrate for skin[10], bone[11], and blood vessel replacement[12]. Collagen has typically been used as a scaffold to support tissue growth and promote healing or for the development of engineered tissues in organ replacement therapies. In virtually any application, wherever collagen is used, CMP modified collogen maybe substituted.

Collagen and Human Disease

Collagens are complex molecules that provide structure, strength, and elasticity (the ability to stretch) to connective tissue. Mutations in I, II, III, IX, X, and XI collagens are associated with a variety of human connective tissue disorders affecting bone, cartilage, and blood vessels. Ehlers-Danlos syndrome (EDS) is most often associated with a genetic defect in type I collagen that is characterized by skin hyperextensibility, fragile and soft skin, delayed wound healing with formation of atrophic scars, easy bruising, and generalized joint hypermobility. Osteogenesis imperfecta or "brittle bone disease" arises from mutations in two genes encoding type I collagen. People with osteogenesis imperfecta (OI) have bones that fracture easily, low muscle mass, and joint and ligament laxity. There are four major types of OI ranging in severity from mild to lethal. The appearance of people with OI varies considerably. Individuals may also have a blue or gray tint to the sclera (whites of the eyes), thin skin, growth deficiencies, and fragile teeth. They may develop scoliosis, respiratory problems, and hearing loss.

Type II and type XI collagens are components of the cartilage found in joints and the spinal column, the inner ear, and the vitreous humor of the eye. The type H and XI collagenopathies include achondrogenesis type 2, hypochondrogenesis, Kniest dysplasia, otospondylomegaepiphyseal dysplasia, spondyloepimetaphyseal dysplasia, Strudwick type, spondyloepiphyseal dysplasia congenita spondyloperipheral dysplasia, Stickler syndrome, and Weissenbacher-Zweymüller. The clinical features of the type II and XI collagenopathies typically include problems with bone development that results in short stature, enlarged joints, spinal curvature, and juvenile arthritis. Problems with vision and hearing, as well as a cleft palate with a small lower jaw, are common.

Diagnostics

Given the propensity of collagen mimetic peptides to interact with collagen, compositions of the invention can be used to visualize the structure of collagen by binding a collagen mimetic peptide conjugate to collagen present in a patient sample. In one embodiment, compositions of the invention are used for the diagnosis of a disease or disorder characterized by an alteration in the structure of collagen. In one approach, a nanoparticle having a collagen mimetic peptide, or collagen mimetic peptide conjugate is used as a diagnostic. Such nanoparticles are used to examine the structure of collagen in biological samples derived from patients suspected of having a connective tissue disorder related to the disruption of collagen. The collagen mimetic peptide allows for the physical association of the nanoparticle with a collagen (e.g., type 1-29) present in the tissue sample. The tissue sample is then analysed using a transmission electron microscopy. Under transmission electron microscopy, collagen fibers exhibit characteristic banding patterns. CMP-NPS bind to defined locations within the collagen fiber. This binding pattern provides an indication of the structural integrity of the collagen molecules and their assembly. Alterations in the structural integrity can be visualized with CMP-NP and correlated with particular connective tissue disease states. Thus, CMP-NP are useful as diagnostics for the identification of alterations in collagen types 1-29.

In other embodiments, compositions of the invention are used to identify the presence of a thrombosis comprising collagen in a vessel or to identify vessels having an increased risk of having a thrombosis. Vessels that have been subjected to angioplasty are particularly prone to the formation of a thrombosis.

Collagen Mimetic Peptide Conjugates

Collagen mimetic peptides may be conjugated to a variety of agents using methods known in the art and described herein. Typically, this conjugation is mediated by a covalent bond. Suitable agents include therapeutic and diagnostic agents. Such agents include, but are not limited to, antibiotics, anti-thrombotics, cell adhesion molecules, components of the extracellular matrix, contrast reagents, detectable labels, growth factors, polymers, PEG, and small compounds having biological activity.

Antimicrobial Agents

Any antimicrobial agent known in the art can be used in the compositions of the invention at concentrations generally used for such agents. Antimicrobial agents include antibacterials, antifungals, and antivirals.

Exemplary antibiotics (i.e., antibacterial agents) include the penicillins (e.g., penicillin G, ampicillin, methicillin, oxacillin, and amoxicillin), the cephalosporins (e.g., cefadroxil, ceforanid, cefotaxime, and ceftriaxone), the tetracyclines (e.g., doxycycline, minocycline, and tetracycline), the aminoglycosides (e.g., amikacin, gentamycin, kanamycin, neomycin, streptomycin, and tobramycin), the macrolides (e.g., azithromycin, clarithromycin, and erythromycin), the fluoroquinolones (e.g., ciprofloxacin, lomefloxacin, and norfloxacin), and other antibiotics including chloramphenicol, clindamycin, cycloserine, isoniazid, rifampin, and vancomycin.

In particular embodiments, a penicillin-CMP antibiotic has the following structure:

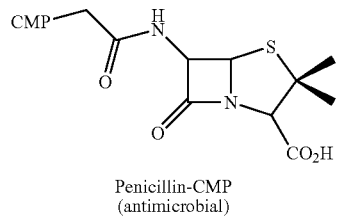

Penicillin-CMP
(antimicrobial)

In another embodiment, a tetracycline-CMP antibiotic has the following structure:

Tetracycline-CMP (antimicrobial)

In still other embodiments, the antimicrobial is a plectasin-CMP or an LAH4-CMP having the following sequences, respectively:

```
Plectasin-CMP (antimicrobial)          (SEQ ID NO: 32)
GFGCNGPWDEDDMQCHNHCKSIKGYKGGYAKGGFVCKCY-CMP LAH4-CMP                               (SEQ ID NO: 33)
KKALLALALHHLAHLALHLALALKKA-CMP.
```

Antiviral agents are substances capable of inhibiting the replication of viruses. Examples of anti-viral agents include 1,-D-ribofuranosyl-1,2,4-triazole-3 carboxamide, 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Antifungal agents include both fungicidal and fungistatic agents such as, for example, benzoic acid, undecylenic alkanolamide, ciclopirox olamine, polyenes, imidazoles, allylamine, thicarbamates, amphotericin B, butylparaben, clindamycin, econaxole, fluconazole, flucytosine, griseofulvin, nystatin, and ketoconazole.

Atherosclerosis Therapeutics

In other embodiments, a CMP conjugate is used for the treatment of atherosclerosis. For such applications a CMP is conjugated, for example to an anti-platelet medication (e.g., aspirin), anti-coagulants (e.g., as heparin, warfarin, aspirin, ticlopidine, and clopidogrel) or inhibitors of platelet clumping. Other atherosclerosis therapeutics include, but are not limited to, cholestyramine, colestipol, nicotinic acid, gemfibrozil, probucol, atorvastatin, lovastatin.

Anti-Thrombotics

The collagen mimetic peptides are also useful for the delivery of compounds having anti-thrombotic activity. Such compounds include heparin, hirudin, ReoPro™, Streptokinase, urokinase, and tissue plasminogen activator (t-PA). Other drugs include recombinant, or genetically engineered, t-PA (a newer version of t-PA) and TNK (Tenecteplase) or other anti-thrombotic compounds. In one particular embodiment, the anti-thrombotic is PEG-CMP having the following structure:

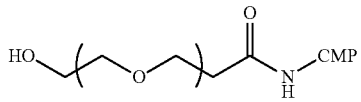

In still other embodiments, the anti-thrombotic is a saratin-CMP or a hirudin CMP conjugate having the following sequences, respectively:

```
Saratin-CMP (anti-platelet)              (SEQ ID NO: 34)
EEREDCWTFYANRKYTDFDKSFKKSSDLDECKKTCFKTEYCYIVFEDTVN

KECYYNVVDGEELDQEKFVVDENFTENYLTDCEGKDAGNAAGTGDESDEV

DED-K-(CMP)₂

Hirudin-CMP (anti-platelet)              (SEQ ID NO: 35)
LTYTDC(6)TESGQNLC(14)LC(16)EGSNVC(22)GQGNKC(28)ILG

SDGEKNQC(39)VTGEGTPKPQSHNDGDFEEIPEEY(SO3)LQ-K-

(CMP)₂.
```

Cell Adhesion Molecules

Cell adhesion molecules suitable for CMP conjugation include components of the extracellular matrix that promote cell spreading or extension or fragments thereof. Preferably, fragments of a cell adhesion molecule include the adhesion molecule binding domain. Such binding domains include consensus sequences that mediate cell-cell interactions, including the RGD peptide. Integrins bind the RGD motif in cell attachment proteins (See, for example, Tosatti et al., J Biomed Mater Res. 68(3):458-72, 2004; and Reyes et al., J Biomed Mater Res 69:591-600, 2004, which are hereby incorporated by reference). Such molecules may be conjugated to a collagen mimetic peptide of the invention for use in the therapeutic compositions described herein. Exemplary cell adhesion molecules include cadherin (e.g., E-cadherin, N-cadherin), cell adhesion molecule (CAM) (e.g., vascular cell adhesion molecule (VCAM)-1 and intracellular adhesion molecule (ICAM)-1 neuronal cell adhesion molecule), fibronectin, integrin (e.g., B-integrin), laminin, and selectin.

Growth Factors

Growth factors are typically polypeptides or fragments thereof that support the survival, growth, or differentiation of a cell. A collagen mimetic peptide described herein can be conjugated to virtually any growth factor known in the art. Such growth factors include angiopoietin, acidic fibroblast growth factors (aFGF) (GenBank Accession No. NP_149127) and basic FGF (GenBank Accession No. AAA52448), bone morphogenic protein (GenBank Accession No. BAD92827), vascular endothelial growth factor (VEGF) (GenBank Accession No. AAA35789 or NP_001020539), epidermal growth factor (EGF) (GenBank Accession No. NP_001954), transforming growth factor α (TGF-α) (GenBank Accession No. NP_003227) and transforming growth factor β (TFG-β) (GenBank Accession No. 1109243A), platelet-derived endothelial cell growth factor (PD-ECGF) (GenBank Accession No. NP_001944), platelet-derived growth factor (PDGF) (GenBank Accession No. 1109245A), tumor necrosis factor α (TNF-α) (GenBank Accession No. CAA26669), hepatocyte growth factor (HGF) (GenBank Accession No. BAA14348), insulin like growth factor (IGF) (GenBank Accession No. P08833), erythropoietin (GenBank Accession No. P01588), colony stimulating factor (CSF), macrophage-CSF (M-CSF) (GenBank Accession No. AAB59527), granulocyte/macrophage CSF (GM-CSF) (GenBank Accession No. NP_000749) and nitric oxide synthase (NOS) (GenBank Accession No. AAA36365).

Components of the Extracellular Matrix

In still other embodiments, a CMP is conjugated to a component of the extracellular matrix (ECM). ECM components include structural proteins, such as collagen and elastin; proteins having specialized functions, such as fibrillin, fibronectin, and laminin; and proteoglycans that include long chains of repeating disaccharide units termed of glycosaminoglycans (e.g., hyaluronan, chondroitin sulfate, dermatan sulfate, heparan sulfate, heparin, keratan sulfate, aggrecan).

Anti-Inflammatories

In other embodiments, a CMP is conjugated to an anti-inflammatory agent. Such anti-inflammatory agents include, but are not limited to, Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen;

Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; and Zomepirac Sodium.

In other embodiments, a CMP is conjugated to an agent having diagnostic applications. Such agents include contrast reagents and detectable labels.

Contrast Reagents

Magnetic resonance imaging (MRI) is typically used for diagnostic purposes to visualized diseased organs or tissues. The utility of MRI is hampered by poor image quality. Collagen mimetic peptides can be conjugated to conventional MRI contrast reagents and then introduced to a desired tissue or tissue sample where the collagen-contrast reagent conjugate binds to collagens present in the tissue to enhance MRI image quality. Exemplary contrast reagents include gadolinium complex, gadodiamide derivative, ferric ammonium citrate, and mangafodipar trisodium.

Detectable Labels

Detectable labels include compositions that when linked to a collagen mimetic peptide render the peptide detectable via spectroscopic, photochemical, biochemical, immunochemical, or chemical means. Exemplary detectable labels include radioactive isotopes, magnetic beads, metallic beads, colloidal particles, fluorescent dyes, electron-dense reagents, enzymes (for example, as commonly used in an ELISA), biotin, digoxigenin, and haptens.

Polymers

Figure 28:
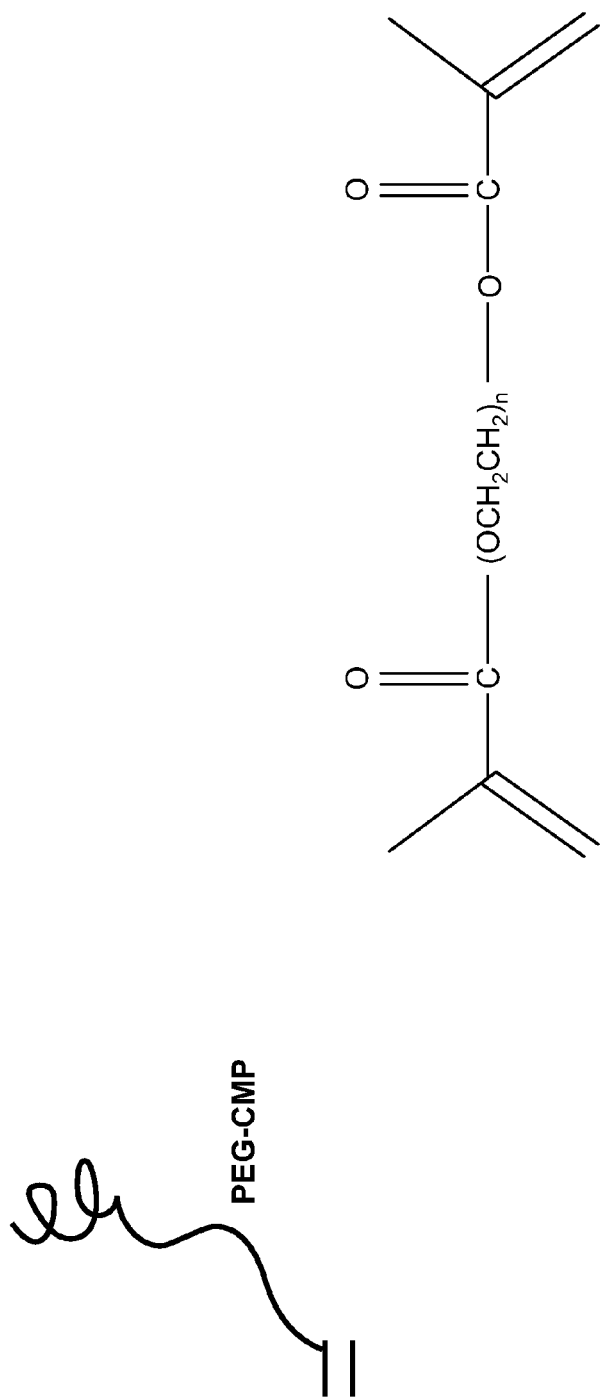
FIG. 28 provides a schematic diagram showing monoacrylated PEG-CMP. Monoacrylated PEG-CMP is polymerized with difunctional PEG to form a hydrogel.

Virtually any polymer known in the art may be conjugated to a CMP. In one embodiment, attachment occurs via an acrylate group (e.g., PEG monoacrylate, PEG diacrylate, see FIG. 28). Polymers that are biocompatible, non-immunogenic, or that support cell survival or proliferation are preferred. Natural or synthetic polymers capable of forming a matrix are particularly useful. A matrix is a substance that fills the spaces between isolated cells in culture. For some applications, a matrix is an adhesive substrate used to coat a glass or plastic surface prior to cell culture. For other applications, cells are embedded in a matrix, or injected into a matrix already implanted at a desired site. In another approach, a matrix provides a physical support and an adhesive substrate for isolated cells during in vitro culturing and subsequent implantation. Preferred polymers for use in a matrix have mechanical and biochemical properties that enhance the viability and proliferation of transplanted cells, tissues, or organs. The matrix configuration is dependent on the tissue that is to be treated, repaired, or produced, but desirably, the matrix is a pliable, biocompatible, porous template that allows for cell and/or vascular growth.

Preferred polymers for use in the methods of the invention include poly(ethylene glycol) (PEG), star shaped PEG, grafted linear PEG, poly(ethylene oxide) diacrylate (PEODA), polyacrylic acid, poly vinyl alcohol, collagen gels, poly (D, L-lactide-co-glycolide (PLGA) fiber matrices, polyglactin fibers, calcium alginate gels, polyglycolic acid (PGA) meshes, and other polyesters, such as poly-(L-lactic acid) (PLLA) and polyanhydrides. Matrices can include materials that are non-biodegradable or biodegradable. Desirably, biodegradable materials will degrade over a time period of less than a year, more preferably less than six months.

Desirably, a collagen mimetic peptide is conjugated to a polymer capable of forming a hydrogel. A hydrogel is formed when an organic polymer (natural or synthetic) is cross-linked via covalent, ionic, or hydrogen bonds to create a three-dimensional open-lattice structure that entraps water molecules to form a gel. Examples of materials that can be used to form a hydrogel include poly(ethylene glycol), polysaccharides (e.g., alginate), polyphosphazenes, and polyacrylates (e.g., hydroxyethyl methacrylate). Other materials that can be used include proteins (e.g., fibrin, collagen, fibronectin) and polymers (e.g., polyvinylpyrrolidone), and hyaluronic acid.

In general, these polymers are at least partially soluble in aqueous solutions, such as buffered salt solutions, or aqueous alcohol solutions. In one embodiment, the polymer includes a charged side group, or monovalent ionic salt thereof. Examples of polymers with acidic side groups that can be reacted with cations are poly (phosphazenes), poly (acrylic acids), poly (methacrylic acids), copolymers of acrylic acid and methacrylic acid, poly (vinyl acetate), and sulfonated polymers (e.g., sulfonated polystyrene). Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups. Examples of polymers with basic side groups that can be reacted with anions are poly (vinyl amines), poly (vinyl pyridine), poly (vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations in water at room temperature to form a hydrogel matrix. Additional methods for the synthesis of the other polymers described above are known to those skilled in the art (see, for example, Concise Encyclopedia of Polymer Science and Polymeric Amines and Ammonium Salts, E. Goethals, editor, Pergamen Press, Elmsford, N.Y. 1980). Many polymers, such as poly (acrylic acid), are commercially available.

In another approach, a synthetic polymer capable of forming a matrix is used. For some applications, synthetic polymers are preferred for reproducibility and controlled release kinetics. Synthetic polymers that can be used include biodegradable polymers, such as poly(lactide), poly(glycolic acid), poly(lactide-co-glycolide), poly (caprolactone), polycarbonates, polyamides, polyanhydrides, polyamino acids, poly-ortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly (vinyl imidazole), chlorosulphonated polyolifins, polyethylene oxide, polyvinyl alcohol, Teflon and nylon. Non-degradable materials can also be used to form a matrix.

One preferred non-degradable material for implantation of a matrix is a polyvinyl alcohol sponge, or alkylation or acylation derivatives thereof (e.g., ester derivatives), including esters.

Delivery of CMP Conjugates

The invention provides a simple means for delivering biologically active compounds (including nucleic acids, peptides, small molecule inhibitors, and mimetics) conjugated to a collagen mimetic peptide (CMP). Typically, the CMP conjugate is incorporated into a polymer matrix containing natural or synthetic polymers. In one embodiment, the CMP conjugate is incorporated in a collagen matrix. The collagen matrix comprising the CMP conjugate is delivered to a subject and the CMP conjugate is released from the collagen matrix. The CMP conjugate is capable of acting as a therapeutic for the treatment of a disease or disorder that requires controlled and/or localized drug delivery over some period of time (e.g., 1, 3, 5, 7 days; 2, 3, 4 weeks; 1, 2, 3, 6, 12 months). A biologic agent conjugated to a collagen mimetic peptide and found to have medicinal value using the methods described herein is useful as a drug or as information for structural modification of existing compounds, e.g., by rational drug design. Desirably, the conjugates include antibiotics (e.g., penicillin, tetracycline, plectasin, LAH4), cell adhesion molecules (e.g., cadherin, fibronectin, integrin, laminin, selectin), growth factors that promote angiogenesis, cell growth, differentiation, proliferation, neurogenesis, osteogenesis, stem cell renewal, or cell survival (e.g., angiogenin, erythropoietin, vascular endothelial growth factor (VEGF), granulocyte/macrophage colony stimulating factor, macrophage-colony stimulating factor, platelet-derived endothelial cell growth factor, and platelet-derived growth factor), or small molecules, such as anti-thrombotics (e.g., heparin-CMP, Hirudin-CMP, Saratin-CMP), anti-atherosclerosis agents, cartilage repair agents (e.g., chondroitin sulfate, glucosamine sulfate, hyaluronic acid). The polymers including the collagen mimetic peptide conjugates are administered either as liquids or solids. Where the polymers are administered as a liquid, they are typically converted to a solid in vivo by cross-linking. Such crosslinking may be accomplished using any method known in the art, such as photopolymerization.

If desired, collagen mimetic peptide conjugates are incorporated into hydrogel-forming polymeric materials that are useful as drug delivery devices. Hydrogel-forming polymers are polymers that are capable of absorbing a substantial amount of water to form elastic or inelastic gels. Medical devices incorporating hydrogel-forming polymers are capable of being implanted in liquid or gelled form. Once implanted, the hydrogel forming polymer absorbs water and swells. The release of a pharmacologically active agent incorporated into the device using a collagen mimetic peptide takes place through this gelled matrix via a diffusion mechanism. Many hydrogels, although biocompatible, are not biodegradable or are not capable of being remodeled and incorporated into a host tissue.

For therapeutic uses, the compositions or agents identified using the methods disclosed herein may be administered systemically. In one embodiment, a matrix comprising a CMP conjegate is formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the subject. Treatment of subjects (e.g., human patients or other animals) will be carried out using a therapeutically effective amount of a CMP therapeutic conjugate in a physiologically-acceptable carrier, such as a collagen matrix that includes the CMP therapeutic conjugate. Suitable carriers and their formulation are described, for example, in Remington's Pharmaceutical Sciences by E. W. Martin. The amount of the therapeutic agent, to be administered varies depending upon the manner of administration, the age and body weight of the subject, and with the clinical symptoms of the subject. Generally, amounts will be in the range of those used for other agents used in the treatment of similar diseases (e.g., thrombosis, atherosclerosis). A compound is administered at a dosage that controls the clinical or physiological symptoms of the disease as determined by a diagnostic method known to one skilled in the art.

Formulation of Pharmaceutical Compositions

The administration of a compound for the treatment of a disease may be by any suitable means that results in a concentration of the therapeutic that, combined with other components, is effective in ameliorating, reducing, or stabilizing the disease. The compound may be contained in any appropriate amount in a any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in proximity to the tissue or organ that requires treatment; (v) formulations that allow for convenient dosing, such that doses are administered, for example, once every one or two weeks; and (vi) formulations that target an disease by using carriers or chemical derivatives to deliver the therapeutic agent to a particular cell type whose function is perturbed in the disease. For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes that include the CMP therapeutic conjugate.

Typically, a polymer comprising the CMP therapeutic conjugate is delivered to the subject identified as in need of such treatment. A large number of polymers can be used to construct the delivery devices of the present invention. The only requirements are that they are inert, non-immunogenic and of the desired permeability. The rate of passage of the drug through the material by diffusion is generally dependent on the solubility of the drug therein, as well as on the thickness of the wall. This means that selection of appropriate materials for fabricating the wall will be dependent on the particular drug to be used. The rate of diffusion of the effective agent through a polymeric layer(s) of the present invention may be determined via diffusion studies using, for example, a CMP therapeutic conjugate comprising a detectable label as described herein.

In one embodiment, the CMP therapeutic conjugate is contained within a collagen matrix, such that the CMP therapeutic conjugate physically associates with the collagen. The drug delivery devices of the invention may be made in a wide variety of ways, such as by obtaining an effective amount of a CMP therapeutic conjugate in a collagen matrix and compressing the matrix to a desired shape. Once shaped, one or more coating layers is applied. Such coatings are used to delay release of the CMP therapeutic conjugate. The drug delivery system of the invention is administered to subject via any route of administration known in the art. Such routes of administration include intraocular, oral, subcutaneous, intramuscular, intraperitoneal, intranasal, dermal, and the like. The drug delivery system of the invention is particularly suitable for direct implantation.

The delivery system is disclosed for the controlled release of CMP therapeutic conjugate from a collagen matrix into the surrounding environment. Controlled release delivery systems include those systems capable of site specific delivery, extended release, sustained release, delayed release, repeat action, prolonged release, bimodal release, pulsitile release, modified delivery, pH sensitive delivery, and/or target specific delivery, among others.

As used herein, optionally, the system may include agents added to aid in gastric bypass or to modify the release profile due to pH-specific swelling characteristics or site-specific enzyme degradation within the gastrointestinal tract. These agents may include, but are not limited to, at least one of alginate, polysaccharides such as such as gelatin or collagen, guar gum, xanthan gum, pectin, heterogeneous protein mixtures, and polypeptides. The polysaccharides may be pectin and/or an alginate salt, among others. The galactomannan gums may be guar gum, xanthan gum and/or locust bean gum, among others. The polyethylene derivatives may be polyethylene oxide (PEO) and/or polyethylene glycol (PEG), among others. The hydrolyzed proteins may be gelatin and/or collagen, among others.

Release of the CMP conjugate into the surrounding environment may be accomplished through a rate-controlled hydration and subsequent swelling of hydrophilic agents. The release of the CMP conjugate is determined by the erosion rate and polymeric disentanglement of the swollen hydrophilic matrix. Typically, the swelling of the hydrophilic matrix allows for a highly reproducible, programmable release pattern. The programmability of the system allows for nearly any physiologically relevant release pattern to be accomplished. Formulation specific to the physical characteristics of a CMP therapeutic conjugate and the desired release profile can be accomplished through both theoretical and empirical means, allowing dissolution of the system and CMP therapeutic conjugate release to occur in a specific physiologic region. Release of contents in a given region of the gastrointestinal tract is accomplished by the slowly hydrating hydrophilic matrix containing the biological actives segregated from the external environment until the desired physiologic region of release, which may be employed to achieve gastric bypass. Consideration of both the area and duration of release is essential in formulation so as to program the system with an appropriate ratio of components to ensure the desired release profile.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active active inflammatory bowel disorder therapeutic(s), the composition may include suitable parenterally acceptable carriers and/or excipients. The active inflammatory bowel disorder therapeutic(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active CMP therapeutic conjugate(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers, such as polygalactin, poly-(isobutyl cyanoacrylate), poly(2- hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active active inflammatory bowel disease therapeutic substance). The coating may be applied on the solid dosage form in a similar manner as that described in Encyclopedia of Pharmaceutical Technology, supra.

At least two active therapeutics may be mixed together in the tablet, or may be partitioned. In one example, the first active therapeutic is contained on the inside of the tablet, and the second active therapeutic is on the outside, such that a substantial portion of the second therapeutic is released prior to the release of the first active therapeutic.

Formulations for oral use may also be presented as chewable tablets, or as hard gelatin capsules where the active ingredient is mixed with an inert solid diluent (e.g., potato starch, lactose, microcrystalline cellulose, calcium carbonate, calcium phosphate or kaolin), or as soft gelatin capsules where the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

CMP Conjugates Coatings

A CMP conjugate may be included in a coating material that is used to coat a medical device (e.g., drug delivery or other medical device). Such coatings are used, for example, for altering the adehesive properties of the device or for drug delivery. For example, a polymeric coating, such as collagen, polyethylene glycol, polyurethane, polytetrafluoroethylene, polyalkylmethacrylates, polyarylmethacrylates, poly(ethylene-co-vinyl acetate), or any other polymer or combination of polymers, may be combined with a CMP of the present invention, such that the CMP is fixed to or physically associates with the polymer, and the CMP conjugate polymer combination is applied to a medical device. The CMP conjugate thereby modulates the cell adhesive properties of the medical device or provides for release of a therapeutic from the device. Such coatings can be applied to any medical device known in the art, including, but not limited to, drug-delivering vascular stents (e.g., a balloon-expanded stents); other vascular devices (e.g., grafts, catheters, valves, artificial hearts, heart assist devices); implantable defibrillators; blood oxygenator devices (e.g., tubing, membranes); surgical devices (e.g., sutures, staples, anastomosis devices, vertebral disks, bone pins, suture anchors, hemostatic barriers, clamps, screws, plates, clips, vascular implants, tissue adhesives and sealants, tissue scaffolds); membranes; cell culture devices; chromatographic support materials; biosensors; shunts for hydrocephalus; wound management devices; endoscopic devices; infection control devices; orthopedic devices (e.g., for joint implants, fracture repairs); dental devices (e.g., dental implants, fracture repair devices), urological devices (e.g., penile, sphincter, urethral, bladder and renal devices, and catheters); colostomy bag attachment devices; ophthalmic devices (e.g. intraocular coils/screws); glaucoma drain shunts; synthetic prostheses (e.g., breast); intraocular lenses; respiratory, peripheral cardiovascular, spinal, neurological, dental, ear/nose/throat (e.g., ear drainage tubes); renal devices; and dialysis (e.g., tubing, membranes, grafts), urinary catheters, intravenous catheters, small diameter grafts, vascular grafts, artificial lung catheters, atrial septal defect closures, electro-stimulation leads for cardiac rhythm management (e.g., pacer leads), glucose sensors (long-term and short-term), degradable coronary stents (e.g., degradable, non-degradable, peripheral), blood pressure and stent graft catheters, birth control devices, prostate cancer implants, bone repair/augmentation devices, breast implants, cartilage repair devices, dental implants, implanted drug infusion tubes, intravitreal drug delivery devices, nerve regeneration conduits, oncological implants, electrostimulation leads, pain management implants, spinal/orthopedic repair devices, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, hemodialysis devices, catheter cuff, anastomotic closures, vascular access catheters, cardiac sensors, uterine bleeding patches, urological catheters/stents/implants, in vitro diagnostics, aneurysm exclusion devices, and neuropatches. Examples of other suitable devices include, but are not limited to, vena cava filters, urinary dialators, endoscopic surgical tissue extractors, atherectomy catheters, clot extraction catheters, coronary guidewires, drug infusion catheters, esophageal stents, circulatory support systems, angiographic catheters, coronary and peripheral guidewires, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, electrophysiology catheters, stroke therapy catheters, abscess drainage catheters, biliary drainage products, dialysis catheters, central venous access catheters, and parental feeding catheters.

Other examples of medical devices suitable for the present invention include, but are not limited to implantable vascular access ports, blood storage bags, blood tubing, central venous catheters, arterial catheters, vascular grafts, intraaortic balloon pumps, cardiovascular sutures, total artificial hearts and ventricular assist pumps, extracorporeal devices such as blood oxygenators, blood filters, hemodialysis units, hemoperfusion units, plasmapheresis units, and artificial organs. It is noted that in other embodiments of the present invention, the CMP conjugates of the present invention may also be adhered to the medical device by means other than coating materials, such as adhesives or compression.

In one embodiment, a polymeric solution is applied to the surface of a device, and a CMP conjugate is applied subsequently. The polymeric solution comprising the CMP is allowed to dry, cure and/or polymerize thereby fixing the CMP conjugate to the polymeric material coating. In another embodiment, the CMP is allowed to associate with the polymer prior to, during or following application of the CMP polymer conjugate to the device. In still other embodiments, the CMP conjugate includes a therapeutic agent suitable for delivery from a CMP polymer coating.

Any suitable administration method know in the art may be utilized to administer the CMP conjugate to the surface. For example, the CMP conjugate may be administered to the surface by press rolling the polymer coated surface in the CMP conjugate, spraying the CMP conjugate onto the device, or gently heating (e.g., below the transition melting temperature) the polymer coating in the presence of a CMP conjugate, such that the heating facilitates the incorporation of the CMP conjugate into the polymer. Typically, such heating is to a temperature sufficient to denature the CMP.

The polymeric materials with biocompatible surfaces may be utilized for various medical applications including, but not limited to, drug delivery devices for the controlled release of pharmacologically active agents, including drug delivery patches, encapsulated or coated stent devices, vessels, tubular grafts, vascular grafts, wound healing devices, including protein matrix suture material and meshes, skin/bone/tissue grafts, adhesion prevention barriers, cell scaffolding, medical device coatings/films and other biocompatible implants.

Wound Healing Devices

The present invention also provides wound healing compositions that utilize a polymeric material comprising a CMP conjugate. The wound healing devices may be configured by fixing a CMP conjugate to a polymer (e.g., a collagen film or PEODA) and forming the CMP conjugate containing polymer into a shape and size sufficient to accommodate the wound being treated. Such wound healing devices are desirably produced in whatever shape and size is necessary to provide optimum treatment to the wound. These devices can be produced in forms that include, but are not limited to, plugs, meshes, strips, sutures, or any other form able to accommodate and assist in the repair of a wound. The damaged portions of the patient that may be treated with a devices made of the particles of the present invention include, but are not limited to, skin, tissue (nerve, muscle, cartilage, brain, spinal cord, heart, lung, etc.) and bone. Other similar devices are administered to assist in the treatment repair and remodeling of a damaged tissue, bone, or cartilage. If desired, the wound healing device comprises a matrix containing one or more cells. For some applications, it is desirable for the device to be incorporated into an existing tissue to facilitate wound repair. For other applications, it is desirable for the device to degrade over the course of days, weeks, or months.

If desired the CMP is conjugated to a therapeutic agents and the CMP conjugate is delivered to a wound using a polymeric material to form a delivery system. Preferably, the polymer contains an effective amount of a CMP conjugate that includes a dosage of the chemical or pharmaceutically active component. An adhesive or other adhering means may be applied to the outer edges of the polymeric material to hold the patch in position during the delivery of the chemical or pharmaceutically active component. This polymeric delivery system provides for the systematic and/or locally administration of a desired amount of a therapeutic agent.

Other embodiments of the present invention include wound-healing devices configured and produced as polymeric material biological fasteners, such as threads, sutures and woven sheets. Threads and sutures comprising various embodiments of the polymeric material provide a biocompatible fastening and suturing function for temporarily treating and sealing an open wound. Additionally, the biological fasteners may include pharmacologically active agents that may assist in the healing and remodeling of the tissue within and around the wound.

In other embodiments, the CMP conjugate is administered directly to an injured area. The CMP conjugate is administered by sprinkling, packing, implanting, inserting or applying or by any other administration means to open wounds on the body.

Hemostatic Applications

The invention further provides hemostatic matrices (e.g., hemostatic sponges) that contain a polymer, such as collagen, and a CMP or CMP conjugate capable of absorbing bodily fluids (e.g. blood). Such matrices generally comprise porous compositions formed from a suitable biocompatible matrix. Suitable biocompatible matrix materials include naturally-occurring polymers, such as collagen, and/or synthetic polymers. In general, sponge matrices can be formed by providing a liquid solution or suspension of a matrix-forming material, and causing the material to form a porous three-dimensionally stable structure. In one embodiment, a collagen solution is prepared. Collagen is derived from a natural source (e.g., bovine, porcine, human) or is synthetically-derived. The collagen is typically digested to form a collagen solution. Such digestion is usually carried out under acidic conditions. Optionally, enzymatic digestion may be utilized using known enzymes for this purpose such as pepsin, trypsin, and/or papain. After digestion, the enzymes are removed using standard methods. Additional information relating to collagenous matrix materials and their preparation, is described in U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety.

A CMP or CMP conjugate is incubated with the collagen prior to, during, or after polymerization, such that the CMP or CMP conjugate is incorporated into the collagen. This incubation is typically carried out at a temperature that is above the melting point of the CMP as determined using methods described herein. If desired, the collagen solution is heated gently (e.g., at or below the transition melting temperature of the CMP) to destabilize the collagen and to facilitate incorporation of the CMP. Preferably, the heating is below the level required to denature the collagen. If desired, the resulting collagen solution is crosslinked. Such crosslinking may be achieved using CMPs. Alternatively, conventional crosslinking agents are used, such as glutaraldehyde, formaldehyde, carbodiimides, UV irradiation, or other crosslinking agents. In one embodiment, a polyepoxide crosslinker is used, such as polyglycidyl ether (e.g., ethylene glycol diglycidyl ether). Typically, polyglycidyl ethers or polyepoxide compounds impart polar groups and a hydrophilic character to the resulting matrix. Preferably, the resulting matrix is wettable and provides for rapid hydration and expansion.

Sponge matrix materials of the invention will advantageously be highly expandable when wetted. Preferably, the sponge has the capacity to expand at least 100%, 200%, 300%, 500%, or 1000% by volume when wetted to saturation with deionized water. Preferred sponge materials achieve rapid volume expansions (e.g., maximum expansion in less than 10 seconds or 5 seconds, when immersed in deionized water) Hemostatic sponges are produced in any size required for application to a wound. Preferably, the expanded sponge exerts compression on surrounding tissues when implanted or delivers an active agent to the implantation site and surrounding tissue.

Compact, dense sponge matrices of the invention are prepared by first hydrating a porous sponge matrix, and then compressing and drying the matrix. Drying will be conducted to reduce the liquid (e.g. water) content of the matrix to less than about 5%, 10%, or 20% by weight. The sponge matrix is stabilized structurally and remains in a highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

For medical use, the compacted or compressed sponge is sterilized using any suitable means (e.g., radiation). The device is packaged in sterile packaging for medical use.

Sponge elements or other devices of the invention may also contain one or more active therapeutic agents. For example, they include agents that promote clotting (e.g., thrombin and/or fibrinogen). Alternatively or in addition, sponge elements or other devices of the invention include growth factors that promote tissue growth and healing.

Methods for Constructing Engineered Tissue Scaffolds

Polymeric matrices that comprise a collagen mimetic peptide are useful for supporting the survival of a variety of cell types including, but not limited to, endothelial cells, dendritic cells, stem cells or other multipotent progenitor cells, skin cells, liver cells, heart cells, kidney cells, pancreatic cells, lung cells, bladder cells, stomach cells, intestinal cells, cells of the urogenital tract, breast cells, skeletal muscle cells, skin cells, bone cells, cartilage cells, keratinocytes, hepatocytes, gastro-intestinal cells, epithelial cells, endothelial cells, mammary cells, skeletal muscle cells, smooth muscle cells, parenchymal cells, osteoclasts, or chondrocytes. These cell-types may be introduced prior to, during, or after gelation. This introduction may take place in vitro or in vivo. When the cells are introduced in vivo, the introduction may be at the site where implantation is desired or at a location removed from that site. Exemplary routes of administration of the cells include injection (e.g., by catheter) and surgical implantation.

A polymeric matrix comprising a collagen mimetic peptide can be filled with cells from virtually any organ. Because many cell-types can be expanded in vitro, grafts can be made using a limited number of cells (e.g., 100, 500, 1000, 10,000, 100,000, 1,000,000, 10,000,000, or 100,000,000), which represent a small percentage (e.g., 0.0001%, 0.001%, 0.005%, 0.01%, 0.05%, 0.10%, 1.0%, 2.0%, or 5.0%) of the cells present in a naturally-occurring tissue or organ. Exemplary cells for organogenesis include, hepatocytes, myocytes (e.g., cardiac or skeletal muscle myocytes), keratinocytes, osteocytes, chondrocytes, islet cells, nerve cells, astrocytes, glial cells from the central or peripheral nervous system, preadipocytes derived from fat or breast tissue, and adipocytes. Such cells might be obtained from the intended implant recipient (an autograft), from a donor (allogeneic graft), or from a cell line. One particular advantage of autografts is that the grafted tissue does not induce an immune response because the grafted cells are recognized as self (Heath et al., Trends Biotechnol, 18: 17-19, 2000). In other embodiments, such cells are obtained from a mammal of a different species (e.g., pig or primate).

Cell Isolation

One aspect of the invention pertains to a matrix that may be used to promote the healing of an injured tissue, for replacement of a damaged or absent tissue, or for tissue augmentation. The implanted cells may be derived from the recipient's own tissue, derived from a different individual of the same species, or derived from a mammalian species that is different from the recipient (e.g., pig or primate). Cells can be isolated from a number of sources, for example, from biopsies or autopsies using standard methods. The isolated cells are preferably autologous cells obtained by biopsy from the subject. The cells from a biopsy can be expanded in culture. Cells from relatives or other donors of the same species can also be used with appropriate immunosuppression. Methods for the isolation and culture of cells are discussed in Fauza et al. (J. Ped. Surg. 33, 7-12, 1998).

Cells are isolated using techniques known to those skilled in the art. For example, a selected tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with digestive enzymes (e.g., trypsin, chymotrypsin, collagenase, elastase, hyaluronidase, DNase, pronase, and dispase). Mechanical disruption can be accomplished by scraping the surface of the organ, the use of grinders, blenders, sieves, homogenizers, pressure cells, or sonicators. For a review of tissue disruption techniques, see Freshney, (Culture of Animal Cells. A Manual of Basic Technique, 2d Ed., A. R. Liss, Inc., New York, Ch. 9, pp. 107-126, 1987) Preferred cell types include, without limitation, chondrocytes, endothelial cells, osteoblasts, and nerve cells. Once the tissue has been reduced to a suspension of individual cells, the suspension can be fractionated into subpopulations. This may be accomplished using standard techniques (e.g., cloning and positive selection of specific cell types or negative selection, i.e., the destruction of unwanted cells). Selection techniques include separation based upon differential cell agglutination in a mixed cell population, freeze-thaw procedures, differential adherence properties of the cells in the mixed population, filtration, conventional and zonal centrifugation, unit gravity separation, countercurrent distribution, electrophoresis and fluorescence-activated cell sorting. For a review of clonal selection and cell separation techniques, see Freshney, Culture of Animal Cells, A Manual of Basic Techniques, 2d Ed., A. R. Liss, Inc., New York, Ch. 11 and 12, pp. 137-168, 1987).

Cell fractionation may be useful when the donor has a disease, such as cancer. Isolated cells can be cultured in vitro to increase the number of cells available for transplantation. The use of allogenic cells, and more preferably autologous cells, is preferred to prevent tissue rejection. However, if an immunological response does occur in the subject after implantation of the engineered organ, the subject may be treated with immunosuppressive agents, such as cyclosporin or FK506, to reduce the likelihood of rejection.

Isolated cells may be transfected. Useful genetic material may be, for example, genetic sequences that are capable of reducing or eliminating an immune response in the host. For example, the expression of cell surface antigens such as class I and class II histocompatibility antigens may be suppressed. This may allow the transplanted cells to have reduced chance of rejection by the host. In addition, transfection could also be used for gene delivery. The cell-substrate construct can carry genetic information required for the long-term survival of the host or the artificial organ or for detecting or monitoring the cells. In one example, the implanted cell or cells are genetically modified to express a bioactive molecule that promotes cell growth or survival. In another example, the cell or cells are genetically modified to expresses a fluorescent protein marker. Exemplary markers include GFP, EGFP, BFP, CFP, YFP, and RFP. The cell-substrate construct can also carry genetic information required for promoting or maintaining angiogenesis. Transfection may be used for transient gene expression or stable gene expression by incorporation of the gene into the host cell.

Isolated cells can be normal or genetically-engineered to provide additional or normal function. Methods for genetically engineering cells with viral vectors such as retroviral vectors or other methods known to those skilled in the art can be used. These include using expression vectors which transport and express nucleic acid molecules in the cells (see, for example, Goeddel et al., (Gene Expression Technology: Methods in Enzymology 185, AcademiPress, San Diego, Calif., 1990). Vector DNA is introduced into prokaryotic oreukaryotic cells via conventional transformation or transfection techniques. Suitable methods for transforming or transfecting host cells can be found in Sambrook et al. (Molecular Cloning: A Laboratory Manual, 2nd Edition, Cold Spring Harbor Laboratory press (1989)), and other laboratory textbooks.

Methods for Repairing Damaged Tissues and Organs

The invention features methods of repairing diseased or damaged tissues and organs. Cells are administered to a damaged or diseased tissue or organ. These methods may stabilize a damaged tissue or organ in a patient on a transplantation waiting list; or the methods may repair a damaged or diseased tissue or organ, thereby obviating the need for transplantation. Methods for repairing damaged tissue or organs may be carried out either in vitro, in vivo, or ex vivo.

Methods for Producing Engineered Tissues or Organs

The invention features methods of producing an engineered replacement tissue. Cells are preferably cultured in the presence of a matrix that contains a CMP or CMP conjugate. If desired, a CMP conjugate is used to modulate the adhesive properties of the matrix. For some applications, the CMP is conjugated to a PEG, such that the CMP PEG conjugate is designed to repel the adhesion of a cell. In another embodiment, the CMP conjugate is designed to promote cell adhesion, thereby promoting incorporation of the matrix (e.g., a synthetic polymer based matrix, decellularized skin or other tissue source; collagen or other extracellular matrix gel) into an existing tissue as described herein. Methods for producing an engineered tissue or organ may be carried out either in vitro, in vivo, or ex vivo. It is also contemplated that matrices of the invention comprising cells are administered to a mammal to treat damage or deficiency of cells in an organ, muscle, or other body structure, or to form an organ, muscle, or other body structure. Desirable organs include the bladder, brain, nervous tissue, glial tissue, esophagus, fallopian tube, heart, pancreas, intestines, gallbladder, kidney, liver, lung, ovaries, prostate, spinal cord, spleen, stomach, testes, thymus, thyroid, trachea, urogenital tract, ureter, urethra, uterus, breast, skeletal muscle, skin, bone, and cartilage.

Engineered Bone or Cartilage

Exemplary transplantation methods of the present invention include repairing or replacing bone or cartilaginous tissue, such as articular cartilage. Traditional bone or cartilage tissue engineering methods can be improved by administering chondrocytes in a matrix comprising collagen mimetic peptides to the damaged or diseased bone or cartilage in vivo or to a bone or cartilage transplant tissue before, during, or after the transplant tissue is administered to a mammal. Traditional bone and cartilaginous tissue reconstruction methods are described, for example, in U.S. Pat. Nos. 6,197,061; 6,197,586; 6,228,117; 6,419,702; and 6,451,060. Engineered bone is useful for the treatment of a variety of diseases or disorders, including arthritis, cancer, congenital defects of bone or cartilage such as worn or torn cartilage in joint linings (e.g., knee joint, hip joint, and temporomandibular joint) and trauma. It is known that connective-tissue cells, including fibroblasts, cartilage cells, and bone cells, can undergo radical changes of character. A great variety of materials are useful as matrices for this purpose. For example, materials such as PEODA, collagen gels, poly (D, L-lactide-co-glycolide (PLGA) fiber matrices, polyglactin fibers, calcium alginate gels, polyglycolic acid (PGA) meshes, and other polyesters such as poly-(L-lactic acid) (PLLA) and polyanhydrides are among those suggested. Matrices can include materials that are non-biodegradable or biodegradable. Desirably, biodegradable materials will degrade over a time period of less than a year, more preferably less than six months.

Methods for treating connective tissue disorders using engineered cartilaginous or connective tissues are described, for example, in U.S. Pat. Nos. 5,226,914; 5,041,138; 5,368,858; 5,632,745; 6,451,060; 6,197,586; and 6,197,061. Surgical procedures related to bone tissue deficiencies vary from joint replacement or bone grafting to maxillo-facial reconstructive surgery. Such methods are known to the skilled artisan.

Engineered Soft Tissue

Traditional methods of soft tissue reconstruction, as described in U.S. Pat. No. 5,716,404, can be improved by administering cells of the invention in a matrix comprising collagen mimetic peptides to the soft tissue to be transplanted. For example, engineered soft tissue is useful for cosmetic surgery or for reconstruction of the breast, face, or other body part after cancer surgery or trauma. For soft tissue reconstruction, the matrix, which is mixed with cells may form a hydrogel.

Engineered Tissue and Organ Transplantation

A donor organ, donor cell, engineered tissue, or engineered organ is transplanted into a patient (e.g., a human or mammal) for the treatment or stabilization of a condition, disease, or disorder using standard methods known to the skilled artisan. Methods for three-dimensional skeletal muscle tissue-engineering are described by Saxena et al., (Biomed. Mater. Eng. 11 (4): 275-281, 2001).

Corneal Shields

Corneal shields of the invention are ophthalmic lens that contain collagen in association with a collagen mimetic peptide Collagen is a major component of the white sclera and the clear cornea. Natural or synthetic collagens are shaped into a contact lens that can be placed on the surface of the eye. The collagen shield provides a protective environment that promotes the healing of surgical and traumatic wounds to the eye. Such shields are useful as ophthalmic dressings and as ophthalmic drug delivery devices. Drugs or diagnostic agents which can be administered include antibiotics, such as beta-lactam antibiotics, such as cefoxitin, n-formamidoylthienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin and sulfonamides; anti-inflammatories, such as cortisone, hydrocortisone, hydrocortisone acetate, betamethasone, dexamethasone, dexamethasone sodium phosphate, prednisone, methylprednisolone, medrysone, fluorometholone, prednisolone, prednisolone sodium phosphate, triamcinolone, indainethacin, sulindac. Desirably, the corneal shield comprises a physiologically acceptable vehicle having a buffered pH and hypoosmotic, hyperosmotic, or isoosmotic characteristics. Typically, the pH and osmolality of the ophthalmic delivery device is matched to the pH and osmolality of the eye. In some embodiments, the corneal shield is subject to degradation over time. Such degradation is typically accomplished via a naturally occurring enzyme present in tears.

Delivery of Collagen Mimetic Peptide Therapeutics

Collagen mimetic peptide therapeutics include cell containing matrices as well as collagen mimetic peptide conjugates. These therapeutics can be delivered by any method known to the skilled artisan. In one approach, a CMP conjugate is administered via an intravenous catheter that is inserted into a blood vessel and guided through am artery or vein to a desired location. For example, a CMP conjugate that includes an anti-thrombotic is administered via a catheter directly to a clot. The end of the catheter may be placed in the vessels leading to the brain, lung, heart, arm, or leg depending upon the location of the clot. In another approach, a liquid solution containing cells and CMP-polymer conjugates is injected into a desired site or is surgically implanted. The liquid is then polymerized in vivo. Alternatively, the CMP-polymer conjugate is polymerized in vitro and subsequently administered.

The present invention provides methods of treating diseases and/or disorders or symptoms thereof which comprise administering a therapeutically effective amount of a pharmaceutical composition comprising a collagen mimetic peptide of a formulae herein to a subject (e.g., a mammal such as a human). Thus, one embodiment is a method of treating a subject suffering from or susceptible to a disease or disorder that requires targeting of a therapeutic composition to a site comprising collagen or a symptom thereof. The method includes the step of administering to the mammal a therapeutic amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which it is desirable to target a tissue comprising collagen may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Methods for Evaluating Therapeutic Efficacy

Methods of the invention are useful for treating or stabilizing in a patient (e.g., a human or mammal) a condition, disease, or disorder affecting a tissue or organ. Therapeutic efficacy is optionally assayed by measuring, for example, the biological function of the treated or transplanted organ (e.g., bladder, bone, brain, breast, cartilage, esophagus, fallopian tube, heart, pancreas, intestines, gallbladder, kidney, liver, lung, nervous tissue, ovaries, prostate, skeletal muscle, skin, spinal cord, spleen, stomach, testes, thymus, thyroid, trachea, ureter, urethra, urogenital tract, and uterus). Such methods are standard in the art and exemplary methods follow. Preferably, a transplantation method of the present invention, increases the biological function of a tissue or organ by at least 5%, 10%, 20%, 40%, 50%, 60%, 70%, 80%, 90%, 100%, 150%, 200%, or even by as much as 300%, 400%, or 500%. In addition, the therapeutic efficacy of the methods of the invention can optionally be assayed by measuring an increase in cell number in the treated or transplanted tissue or organ as compared to a corresponding control tissue or organ (e.g., a tissue or organ that did not receive treatment). Preferably cell number in a tissue or organ is increased by at least 5%, 10%, 20%, 40%, 60%, 80%, 100%, 150%, or 200% relative to a corresponding tissue or organ. Methods for assaying cell proliferation are known to the skilled artisan and are described in (Bonifacino et al., Current Protocols in Cell Biology Loose-leaf, John Wiley and Sons, Inc., San Francisco, Calif.).)

Screening Assays

As described herein, the present invention provides for the delivery of therapeutic agents to cells, tissues, or organs in vitro or in vivo. The invention is based in part on the discovery that therapeutic agents can be conjugated to a collagen mimetic peptide. Collagen is then contacted with the collagen mimetic peptide conjugate, such that the collagen mimetic peptide conjugate physically associates with collagen. Based in part on this discovery, compositions of the invention are useful for the high-throughput low-cost screening of compounds conjugated to CMP. Desired CMP conjugates physically interact with collagen (e.g., bind with high affinity) without disrupting collagen structure. The CMP conjugate thereby modulates a biological function of a cell, tissue, or organ. Collagen, or tissues or cells comprising collagen are treated with a collagen mimetic peptide conjugate and are subsequently compared to untreated control samples to identify therapeutic CMP conjugates that bind collagen with high affinity without disrupting collagen structure and/or enhance a biological function of the cell, tissue, or organ. Any number of methods are available for carrying out screening assays to identify such compounds.

In one working example, candidate compounds are added at varying concentrations to the culture medium of cultured cells. Any desired biological function is then measured using standard methods. The biological function in the presence of the candidate compound is compared to the level measured in a control culture medium lacking the candidate molecule. A compound that enhances cell function is considered useful in the invention; such a candidate compound may be used, for example, as a therapeutic to prevent, delay, ameliorate, stabilize, or treat a disease described herein (e.g., atherosclerosis, thrombosis, inflammation, tissue damage). In other embodiments, the candidate compound prevents, delays, ameliorates, stabilizes, or treats a disease or disorder described herein. Such therapeutic compounds are useful in vivo as well as ex vivo.

In one working example, CMP conjugates are screened for those that specifically bind to collagen. The efficacy of such a candidate compound is dependent upon its ability to interact with collagen, or with functional equivalents thereof. Such an interaction can be readily assayed using any number of standard binding techniques and functional assays (e.g., those described in herein).

In one example, a CMP conjugate that binds to a collagen is identified using a chromatography-based technique. For example, collagen is immobilized on a column. A solution comprising a CMP conjugate is then passed through the column, and a CMP conjugate is identified on the basis of its ability to bind to the collagen and be immobilized on the column. To isolate the CMP conjugate, the column is washed to remove non-specifically bound molecules, and the CMP conjugate of interest is then released from the column and collected. Similar methods may be used to isolate a CMP conjugate bound to a collagen microarray comprising any collagen type desired (e.g., collagen types 1-29). A CMP conjugate identified using such methods is assayed for an effect on the biological function of a cell, tissue, or organ as described herein.

In another example, the CMP conjugate, e.g., the substrate, is coupled to a radioisotope or enzymatic label such that binding of the compound, e.g., the substrate, to collagen can be determined by detecting the labeled compound, e.g., substrate, in a complex. For example, compounds can be labeled with 125I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

In yet another embodiment, a cell-free assay is provided in which a CMP conjugate or a biologically active portion thereof is contacted with a collagen and the ability of the CMP conjugate to bind to the collagen thereof is evaluated.

The interaction between two molecules can also be detected, e.g., using fluorescence energy transfer (FET) (see, for example, Lakowicz et al., U.S. Pat. No. 5,631,169; Stavrianopoulos et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of a CMP conjugate to bind to a collagen can be accomplished using real-time Biomolecular Interaction Analysis (BIA) (see, e.g., Sjolander, S, and Urbaniczky, C., *Anal. Chem.* 63:2338-2345, 1991; and Szabo et al., *Curr. Opin. Struct. Biol.* 5:699-705, 1995). "Surface plasmon resonance" or "BIA" detects bio-specific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

It may be desirable to immobilize either the CMP conjugate or the collagen target to facilitate separation of complexed from uncomplexed forms of one or both of the proteins, as well as to accommodate automation of the assay. Binding of a CMP conjugate to a collagen, or interaction of a CMP conjugate with a target collagen in the presence and absence of a CMP conjugate, can be accomplished in any vessel suitable for containing the reactants. Examples of such vessels include microtiter plates, test tubes, and micro-centrifuge tubes. Following incubation, the beads or microtiter plate wells are washed to remove any unbound components, the matrix immobilized in the case of beads, complex determined either directly or indirectly, for example, as described above.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., *Trends Biochem Sci* 18:284-7, 1993); chromatography (gel filtration chromatography, ion-exchange chromatography); electrophoresis and immunoprecipitation (see, for example, Ausubel, F. et al., eds. (1999) Current Protocols in Molecular Biology, J. Wiley: New York). Such resins and chromatographic techniques are known to one skilled in the art (see, e.g., Heegaard, N. H., *J Mol Recognit* 11:141-8, 1998; Hage, D. S., and Tweed, S. A., *J Chromatogr B Biomed Sci Appl.* 699:499-525, 1997). Further, fluorescence energy transfer may also be conveniently utilized, as described herein, to detect binding without further purification of the complex from solution.

One skilled in the art appreciates that the effects of a CMP conjugate on biological activity are typically compared to the biological activity in the absence of the CMP conjugate. Thus, the screening methods include comparing the value of a cell modulated by a candidate CMP conjugate to a reference value of an untreated control cell. Changes in tissue or organ morphology further comprise values and/or profiles that can be assayed by methods of the invention by any method known in the art.

Test Compounds and Extracts

In general, therapeutic compounds suitable for coupling to CMP are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is identified as containing a compound of interest, further fractionation of the positive lead extract is necessary to isolate chemical constituents responsible for the observed effect. Thus, the goal of the extraction, fractionation, and purification process is the careful characterization and identification of a chemical entity within the crude extract that achieves a desired biological effect. Methods of fractionation and purification of such heterogenous extracts are known in the art.

Small molecules of the invention preferably have a molecular weight below 2,000 daltons, more preferably between 300 and 1,000 daltons, and most preferably between 400 and 700 daltons. It is preferred that these small molecules are organic molecules.

Kits

The invention provides diagnostic and therapeutic kits that include CMP or CMP conjugates capable of interacting with collagen in vitro or in vivo. In one embodiment, the kit includes a diagnostic composition containing a detectable CMP conjugate (e.g., CMP conjugated to a nanoparticle, a detectable label, or a contrast reagent). In other embodiments, the kit contains a therapeutic device, such as a wound healing device, hemostatic sponge, or drug delivery device containing a CMP conjugate and a polymer.

In some embodiments, the kit comprises a sterile container which contains a CMP conjugate or a CMP conjugate and a polymer; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired a CMP conjugate of the invention is provided together with instructions for using it in a diagnostic or therapeutic method described herein. The instructions will generally include information about the use of the composition for the diagnosis or treatment of a disease in a subject in need thereof. The instructions may be printed directly on the container (when present), or as a label applied to the container, or as a separate sheet, pamphlet, card, or folder supplied in or with the container.

EXAMPLES

Example 1

Methods of Characterizing a CMP or CMP Conjugate

Figure 2:
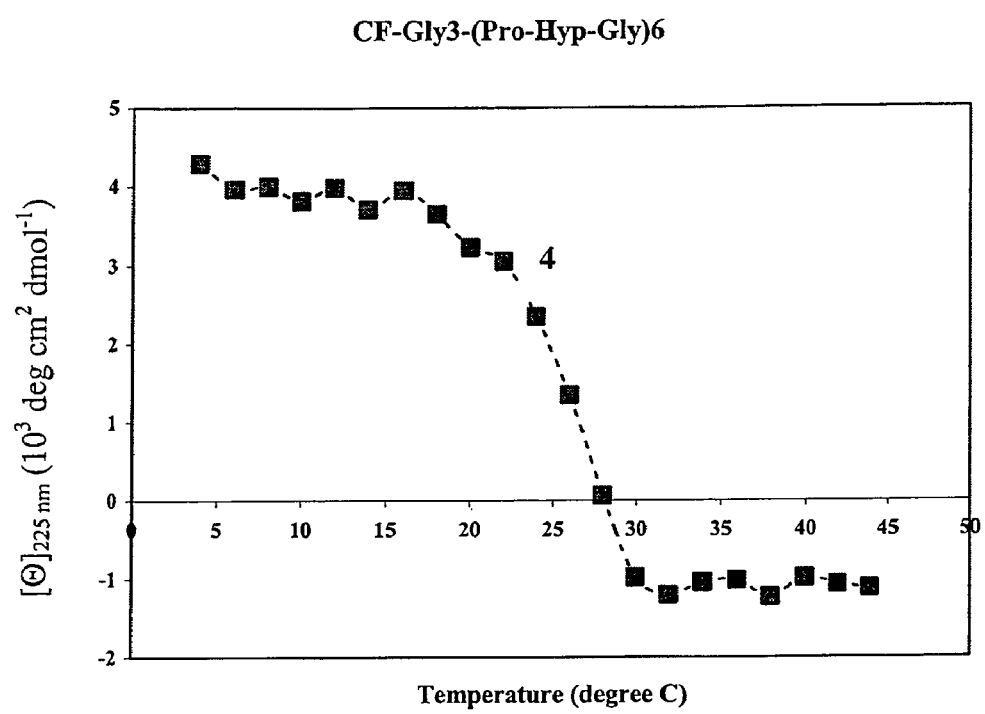
FIG. 2 shows a CD thermal melting curve of CF-Gly$_3$-(PHG)$_6$ (peptide 4) (SEQ ID NO: 23).
Figure 3:
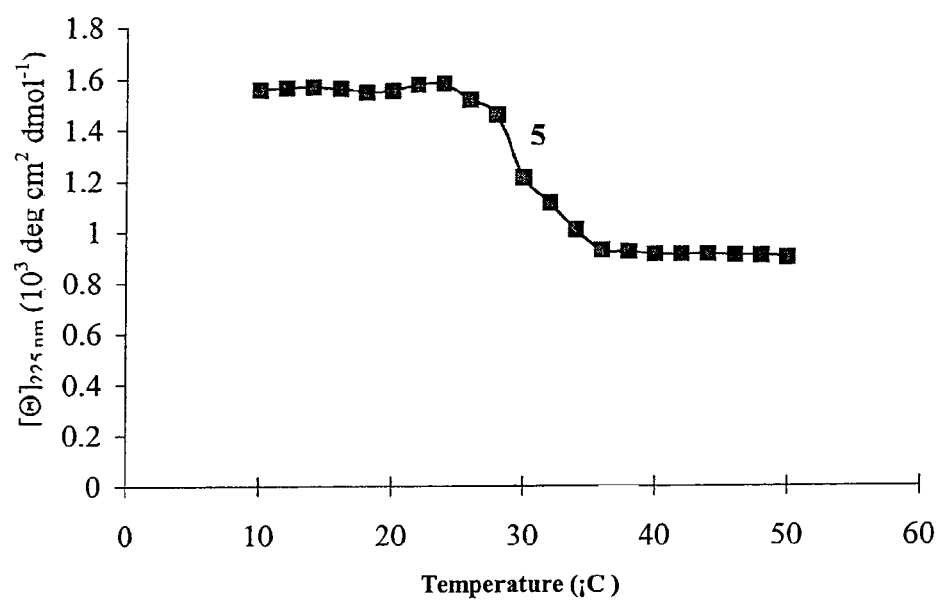
FIG. 3 shows a CD thermal melting curve of mPEG$_{2000}$-Gly$_3$-(PHG)$_7$ (peptide 5) (SEQ ID NO: 6).

To determine whether the propensity of CMPs to form collagen-like triple helices enables it to bind to partially denatured collagen by associating with disentangled domains of the collagen molecules, CMP and 5-carboxy fluorescein (5CF) labeled CMP derivatives were prepared as shown in Table 1 (Table 1:1 and 2, respectively), which provides the sequence and transition melting temperature ($T_m$) of peptides 1-5, as determined by circular dichroism spectroscopy (FIGS. 1-3).

TABLE 1

Transition Temperatures of Collagen Mimetic Peptide Derivatives Determined by Circular Dichroism Spectroscopy[a].

| Compound | Sequence | SEQ ID NO: | Tm |
|---|---|---|---|
| 1 | -(ProHypGly)10- | 36 | 69° C. |
| 2 | 5CF-Gly3-(ProHypGly)10- | 37 | 75° C. |
| 3[b] | 5CF-Gly3-randomPro10Hyp10Gly10- | 38 | — |
| 4 | 5CF-Gly3-(ProHypGly)6- | 39 | 25° C. |
| 5[c] | mPEG2000-Gly3-(ProHypGly)7- | 6 | 29° C. |

[a]measured in 57.5 μM acetic acid solution.
[b]5CF-GGGGPPP$^H$P$^H$GPGGGPP$^H$PP$^H$GP$^H$GPP$^H$PGP$^H$P$^H$PGGP$^H$P$^H$PP (SEQ ID NO: 38), (P$^H$:Hyp).
[c]mPEG$_{2000}$: CH$_3$O—(CH$_2$—CH$_2$—O)$_n$—OH, 2250 Da In addition, peptide 3 was synthesized having the same amino acid composition as peptide 2, but the Pro, Hyp, Gly sequence was scrambled, rendering peptide 3 non-helicogenic. Three consecutive glycines were inserted as a spacer between the fluorescence tag and the CMP. Attaching 5CF and three glycines to 1 elevated its melting temperature from 69° C. to 75° C. (Table 1). This is due in part to the hydrophobic nature of the fluorescence tag. Attachment of a hydrophobic fatty acid to the CMP was previously shown to stabilize the triple helix elevating its melting temperature.[5] As expected, no melting behavior was observed for compound 3.

Figure 5:
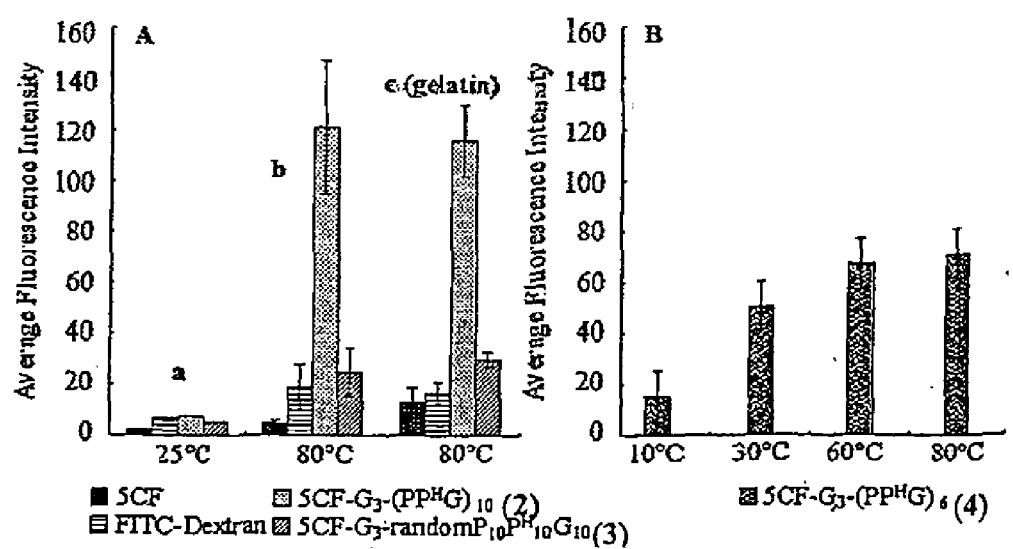
FIGS. 5A and 5B are graphs showing the fluorescence intensities of collagen films (type I, bovine) treated with 5CF labeled CMPs and other control samples. The X axis represents the temperature at which fluorescence solutions were equilibrated prior to addition to the collagen film (see support information).
Figure 5A:
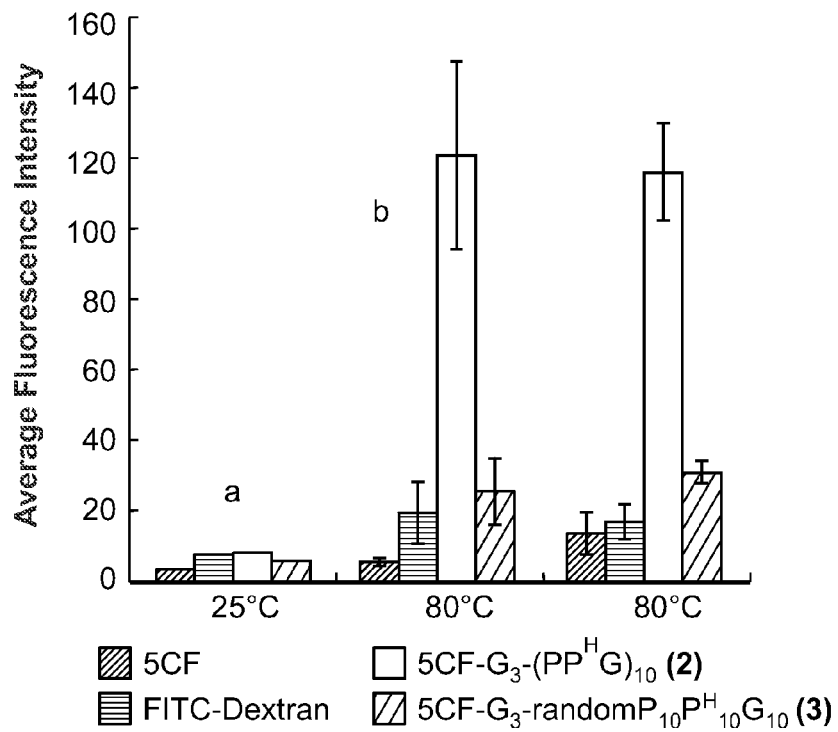

The binding of CMP to natural collagen (acid soluble, bovine type I) or denatured collagen (gelatin) was demonstrated by treating collagen films with solutions of the fluorescently labeled CMP, rinsing, and measuring the fluorescence intensity of the exposed film. The transition melting temperature of collagen film as determined by circular dichroism spectroscopy is shown at FIG. 4. To the collagen-coated cell culture wells (at room temperature) was added a solution of 2 which was pre-equilibrated at either 25° C. or 80° C. After three hours of incubation at room temperature, the collagen films were washed with buffer solution and observed by fluorescence microscope. As control samples, 5CF, fluorescein isothiocyanate-dextran (FITC-Dextran), and peptide 3 were used to treat collagen films under identical experimental conditions. All control samples exhibited negligible affinity toward collagen film evidenced by low fluorescence intensity at both experimental conditions (FIG. 5A: Group a and b). Collagen film treated with peptide 2 at 25° C. also showed negligible fluorescence. In contrast, the collagen film treated with peptide 2 that was pre-equilibrated at 80° C., the temperature above peptide 2's melting transition temperature (75° C.), exhibited strong fluorescence. Similar results were obtained when gelatin films were used as a substrate (FIG. 5A: Group c). In addition, the helical content of CMP treated collagen film was 3.5 times higher than that of the film treated with a blank solution (see support information). These results suggested that peptide 2 tightly attached to partially denatured collagen when it is introduced as a single strand and that its ability to assemble into triple helix is relevant for the attachment.

Figure 5B:
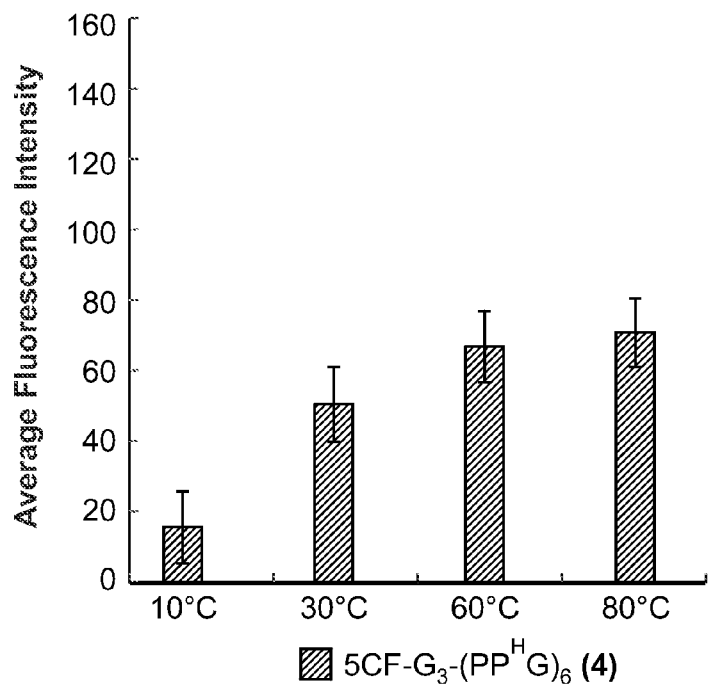
Figure 6:
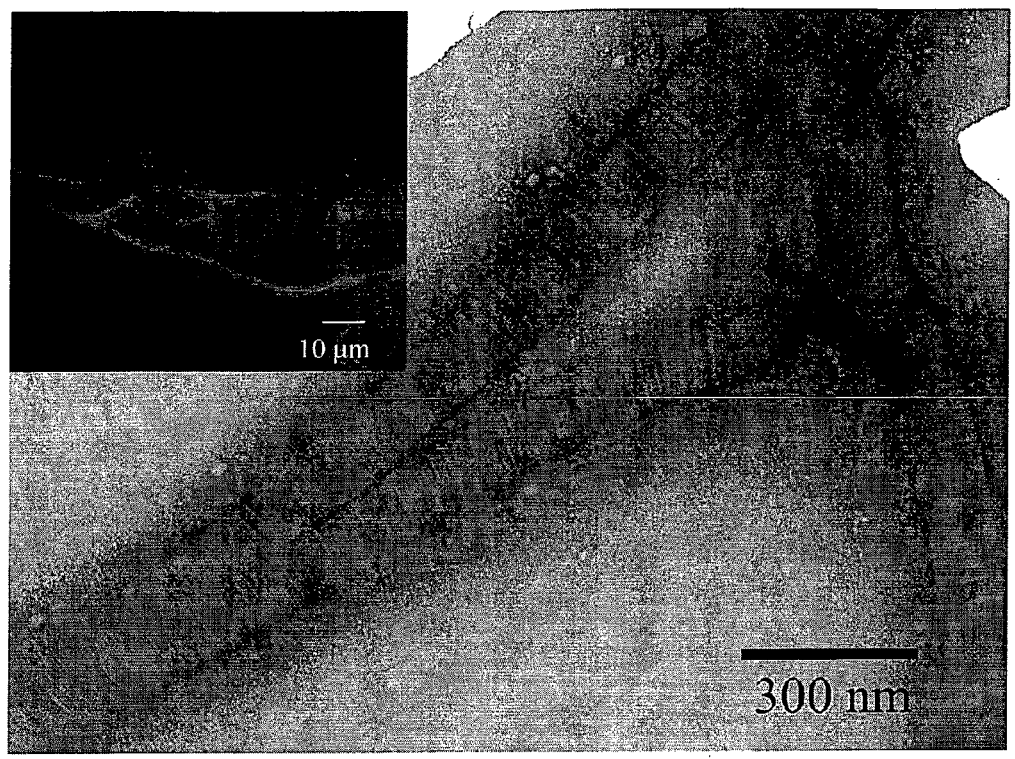
FIG. 6 shows transmission electron and fluorescence (inset) micrographs of collagen fibers (type I) after the treatment with peptide 4 at 30° C. The collagen fibers exhibit native banding pattern suggesting that the modification process did not disrupt the native collagen structure. The presence of peptide 4 on the collagen fiber was confirmed by fluorescence microscopy (inset).

In order to understand the effect of collagen film denaturation in the CMP binding process, a shorter CMP derivative was synthesized, peptide 4, with a melting temperature (25° C.) well below that of the collagen film. Little binding was observed when a peptide 4 solution at 10° C. was used to treat the collagen film (FIG. 5B). Treatment with the same solution pre-equilibrated at 30° C., the temperature above 4's melting temperature but below the denaturation temperature of collagen film (37° C.), induced more than three-fold increase in CMP attachment compared to that of the 10° C. solution. In addition, the modified collagen fiber retained its native banding texture when investigated by transmission electron microscopy (FIG. 6). Hotter solutions (60° C. and 80° C.) which denature the collagen film during the treatment produced collagen films with slightly higher CMP content (approximately 20% increase from that of the 30° C. solution). These results indicated that the CMP melting into monomers, but not collagen denaturation supported CMP immobilization.

The observed adhesion arises from a strand exchange reaction and triple helix association between CMP and the collagen. It is interesting to note that a number of researchers have proposed existence of thermally labile domains within the type I collagen sequence which may serve as potential sites for the presumed strand exchange reaction.[6] Within the collagen family a class of collagen known as Fibril Associated Collagens with Interrupted Triple-helices exists (FAC-ITs)[22-24]. FACITs do not form fibrous structure by themselves but are always found as individual collagen molecules decorating the surface of collagen fibers. The findings reported herein do not indicate if CMP is binding to the thermally labile domains, or if the binding event mimics that of a FACIT protein.

To evaluate the potential of the new modification technique in tissue engineering, poly(ethyleneglycol)$_{2000}$-CMP conjugate polymer[25,26] (Table 1: 5) was prepared. This modified collagen was designed to reduce the adhesiveness of collagen to cells.

The melting temperature of 5 was determined to be 29° C. which is 7° C. lower than the melting temperature of (Pro-HypGly)$_7$ (SEQ ID NO: 40) (Table 1).[27] Here, the hydrophilic and bulky PEG group seems to destabilize the triple helix in water. A solution containing 5 at 45° C. was added to the collagen coated culture plate (prepared as above) and human fibroblasts or breast epithelial cells were seeded and incubated for three days at 37° C. Homogenous distribution of fibroblasts is seen on the collagen film that was treated with mPEG$_{2000}$ (Control sample, FIG. 7A). In contrast, areas of collagen films treated with 5 are almost devoid of fibroblasts (FIG. 7B) and epithelial cells (FIG. 7C). This experiment demonstrates that the adhesive properties of prefabricated collagen film can be readily modified by the simple action of delivering CMP conjugate solutions to the target area.

These results demonstrate that a prefabricated collagen matrix can be readily modified by delivering CMP conjugate solutions to a target area (FIG. 8). Such methods are useful for applications where it is desirable to repel cell growth while new tissue structures are organized.

For applications where it is desirable to repel cell growth for prolonged periods (e.g., weeks or months), it is desirable to employ CMPs of increased length. In films that were treated with mPEG$_{2000}$-Gly$_3$-(Pro-Hyp-Gly)$_7$ (SEQ ID NO: 6), cell growth extending into the treated area was observed after 3 days in culture (FIGS. 9A, 9B, and 9C). This might be due to the release of mPEG$_{2000}$-Gly$_3$-(Pro-Hyp-Gly)$_7$ (SEQ ID NO: 6) from the PEG-CMP modified collagen film during incubation at 37° C.

(Pro-Hyp-Gly)$_8$-Gly$_3$-PEG$_{5000}$-OH (SEQ ID NO: 26) with lengthened CMP and PEG, was designed to prolong the anti-adhesive property of pegylated CMP modified collagen to cells. Its melting temperature is 38° C. in PBS solution. A delay in invasive cell growth was observed on areas of the collagen film treated with (Pro-Hyp-Gly)$_8$-Gly$_3$-PEG$_{5000}$-OH (SEQ ID NO: 26) (FIG. 10A and FIG. 10B). The treated gel repelled extensive cell growth for close to eleven days. After five days in culture, little invasion into treated areas of the collagen film is observed. After nine days in culture only moderate invasion is observed. Extensive invasion is observed after eleven days in culture. It can also be seen from the images that cells outside the treated area grow vertically before invading the treated area.

To determine whether PEG-CMP derivatives are diffusing out of the gel, fluorescence labeled PEG-CMPs, FL-PEG$_{2000}$-Gly$_3$-(Pro-Hyp-Gly)$_7$ (SEQ ID NO: 30) and 5CF-Gly$_3$-(Pro-Hyp-Gly)$_s$-Gly$_3$-PEG$_{5000}$-OH (SEQ ID NO: 31), were prepared. The CF-Gly$_3$-(Pro-Hyp-Gly)$_{10}$ (SEQ ID NO: 51) derivatives bound collagen film with high affinity. FIG. 11 shows a quantitation of the release of fluorescence-labeled CMP derivatives from culture dish and collagen film at 37° C. in PBS solution (pH 7.4). On the fluorescence labeled PEG-CMP modified area of collagen film, the release of FL-PEG$_{2000}$-Gly$_3$-(Pro-Hyp-Gly)$_7$ (SEQ ID NO: 30) from collagen film was faster than that of 5CF-Gly$_3$-(Pro-Hyp-Gly)$_8$-Gly$_3$-PEG$_{5000}$-OH (SEQ ID NO: 31). The release of fluorescence-labeled PEG-CMPs derivatives from collagen films is shown in (FIG. 11). These results suggest that a collagen matrix or other polymer matrix that incorporates a CMP conjugate (e.g., a CMP conjugated to a biologically active agent, is useful for the controlled release of that CMP conjugate as described herein.

These experiments indicate that fibroblast and epithelial cell adhesion to natural collagen can be readily altered by applying CMP-poly(ethylene glycol) conjugates to pre-fabricated collagen films. These PEG-CMP derivatives include methoxy-PEG$_{2000}$-Gly$_3$-(Pro-Hyp-Gly)$_7$ (SEQ ID NO: 6) and (Pro-Hyp-Gly)$_8$-Gly$_3$-PEG$_{5000}$ (SEQ ID NO: 41). Films treated with these compounds showed dramatically reduced invasion by fibroblasts or epithelial cells. For applications where prolonged repellant activity is required stable CMP-PEG derivatives, such as (Pro-Hyp-Gly)$_8$ (SEQ ID NO: 42), will be utilized. (Pro-Hyp-Gly)$_8$ (SEQ ID NO: 42) exhibits stronger affinity for collagen. Also useful in such methods are linear PEG of suitable lengths or star-shaped PEG. Such molecules have increased surface-shielding effects, and are more effective in protecting the conjugates from cell adhesion and protein adsorption (see FIG. 12). A comparison of protein and cell repellent properties of grafted linear PEG and star shaped PEG has been described[13-16]. In particular, star shaped PEG-coated glass, titanium and silicon samples inhibit cell adhesion[17].

Figure 13:
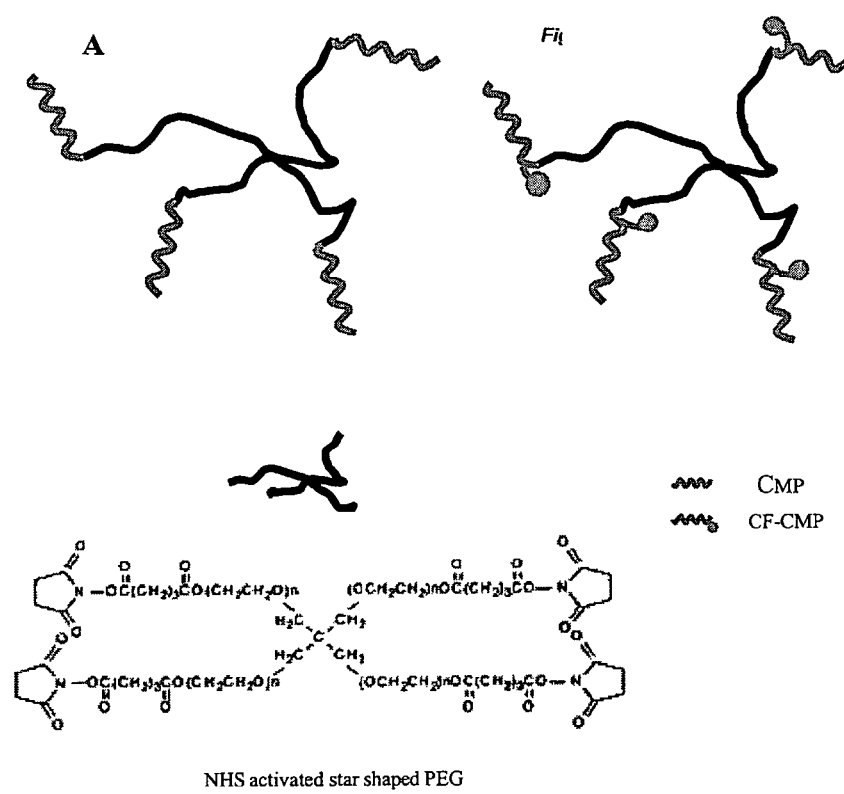
FIG. 13 is a schematic diagram showing the structures of CMP-star shaped PEG. A) [AcGly-Gly$_2$-Lys-Gly$_3$-(Pro-Hyp-Gly)$_8$]$_4$-star shaped PEG (core sequence disclosed as SEQ ID NO: 27). B) [CF-Gly$_3$-Lys-Gly$_3$-(Pro-Hyp-Gly)$_8$]$_4$-star shaped PEG wore sequence disclosed as SEQ ID NO: 28), fluorescence tagged star shaped PEG-CMP. Star shaped PEG: NHS activated four-armed star shaped PEG, molecular weight is approximately 10,000 Da; CMP: AcGly-Gly$_2$-Lys-Gly$_3$-(Pro-Hyp-Gly)$_8$ (SEQ ID NO: 29); CF-CMP: carboxyfluorescein-Gly$_3$-lys-(Pro-Hyp-Gly)$_8$ (SEQ ID NO: 24).

In order to increase the cell repelling activity CMP is conjugated to multi-armed PEG or to star shaped PEG (MW: 10,000 Da). These molecules provide for an increase in the number of collagen binding sites. [AcGly-Gly$_2$-Lys-Gly$_3$-(Pro-Hyp-Gly)$_8$]$_4$-star shaped PEG (core sequence disclosed as SEQ ID NO: 27) (MW: 10,000 Da) will be synthesized by conjugation of four NHS activated sites on 4-armed star PEG with AcGly-Gly$_2$-Lys-Gly$_3$-(Pro-Hyp-Gly)$_8$ (SEQ ID NO: 29) (FIG. 12). The amount of PEG-CMP immobilized in the collagen scaffold will be empirically determined. [Carboxy-fluorescein-Gly$_3$-Lys-Gly$_3$-(Pro-Hyp-Gly)$_8$]$_4$-star shaped PEG (core sequence disclosed as SEQ ID NO: 43) will be prepared (FIG. 13). Fluorescence tagged star shaped PEG-CMP that can be quantified and visualized by fluorescence techniques will also be prepared to facilitate detection of star shaped PEG-CMP release. HPLC will be used to purify the CMP-star shaped PEGs and MALDI-TOF will be used to identify the target products and check for purity.

The ability to control the organization of cells in collagen matrix provides a new pathway for engineered tissues. Furthermore, the affinity between the CMP and collagen could issued to immobilize therapeutic drugs to collagens in the living tissues, and to biomaterials that incorporate natural collagens.

Example 2

Use of PEG-CMP for the Organization of Endothelial Cell Growth

Results using PEG-CMP to repel fibrobast cell growth suggest that PEG-CMP can be used to direct the growth and organization of endothelial cell growth as well, given the similarities that exist between the two cell types. Like fibroblasts, endothelial cells rely on integrin-ECM interaction for initial binding to the scaffolds. To determine the effects of PEG-CMP collagen gels on proliferation, tubulogenesis, and capillary sprouting collagen (type I) films are treated with PEG-CMP of varying concentrations. The amount and pattern of immobilized PEG-CMP present in the collagen film is determined using fluorescien labeled-PEG. Endothelial cells are then plated on PEG-CMP modified collagen and cell attachment, morphology, and cytoskeletal organization is assessed to determine the effect of CMP-PEG modified collagen on cell attachment pattern and cell proliferation. Methods of characterizing cytoskeletal organization include staining with Oregon-Green conjugated phalloidin.

To determine the effects of PEG-CMP on the growth and organization of endothelial cells in three dimensional collagen gel, endothelial cells are cultured in PEG-CMP modified three dimensional collagen gels. On a two dimensional collagen film the PEG-CMP inhibits fibroblast attachment. Without wishing to be bound by theory, this effect is likely due to the PEG blocking the ECM-integrin interaction. To determine whether similar effects are observed in three dimensional ECMs, a three dimensional collagen gel containing varying concentrations of PEG-CMP is prepared by adding PEG-CMP to a collagen solution prior to gelation. Cell morphology is analysed to assess the efficacy of PEG-CMP in regulating cell growth, proliferation, tubulogenesis, and capillary sprouting in a three dimensional collagen gel. Samples of the gel are easily fixed and fluorescently labeled using actin and nuclear immunostaining. One end of the collagen gel is immersed in fluoroscein labeled PEG-CMP solution to create a detectable PEG gradient along the length of the collagen gel. Cell morphology is visualized by actin and nuclear immunostaining, and evaluated using fluorescence microscope, which also provides for visualization of the PEG gradient.

In another approach, CMP-PEG is injected into the collagen gel via microsyringe. This injection is performed at the final stage of gel formation thus minimizing damage to the collagen matrix. The distribution of immobilized fluororescein labeled PEG-CMP is visualized and quantified by fluorescence microscope and the morphology of endothelial cells and capillary distribution is evaluated with respect to the local concentration of PEG-CMP.

Example 3

Tissue Fixation Using $(CMP)_n$ Conjugated-Homo Multifunctional PEG as a Cross-Linker Present methods for tissue fixation use crosslinking reagents, such as formaldehyde, glutaraldehyde (GA), expoxy compounds, carbodiimide, proanthocyanidin and reactive multifunctional PEGs[18,19]. The use of such reagents reduces the antigenicity of many proteins and increases their resistance to enzymatic degradation when tissues treated with these reagents are implanted[20,21]. Additional drawbacks to the use of such agents includes their toxicity, unmanageable crosslinking rates, and instability. The present invention provides a a collagen crosslinking reagent that exhibits low cytotoxicity and can form biocompatible crosslinked products. CMPs conjugated onto multi-armed PEG compounds mediate physical binding to collagen and can serve as crosslinking reagents. CMP conjugated with homo-bifunctional or homo-tetrafunctional PEG, which are commercially available from NEKTAR (San Carlos, Calif.) (such as NHS or thiol) are prepared and purified by HPLC. The reaction products are characterized using MALDI-TOF and CD measurements and rheometry, tensile gel swelling analyses and gel degradation analyses using collagenase are carried out on CMPs-multi armed PEG conjugate cross-linked collagen gels and fixed tissues.

Example 4

CMP Functionalized Gold Nanoparticles

CMP, (Pro-Hyp-Gly)x (Hyp=hydroxyproline), binds to type I collagen molecules through a process involving both strand invasion and triple-helix assembly. In an effort to visualize this interaction in collagen fibers, CMP functionalized gold nanoparticles (NPs) were prepared to use as a transmission electron microscopy marker. The CMP functionalized gold NPs were highly stable in aqueous solution and exhibited a preferential affinity to the gap regions of intact type I collagen fibers.

The triple helical structure of collagen and CMP bears similarity in structure to the DNA double helix. Both collagen and DNA are composed of long coaxial multiplex helices that are held together by inter-chain hydrogen bonds. They exhibit reversible melting transitions that reflect the stability and strength of the helix assembly. In DNA, strand invasion by short DNAs or peptide nucleic acids is well documented in the literature.[28] Although collagens are known to incorporate thermally unstable domains where small segments of the triple helix are thought to be partially unraveled,[29] strand invasion by other collagen molecules or collagen analogs have not been previously reported.

Under transmission electron microscopy, collagen fibers exhibit characteristic banding patterns that indicate the structural integrity of the collagen molecules and their assembly.[30] The banding patterns also provide approximate position markers along the length of collagen molecules. The binding event between type I collagen fibers and CMP conjugated gold NPs was investigated to see if strand invasion occurs without destroying the native structure of collagen fibers. Antibody passivated gold NPs have been used successfully to identify specific types of collagen fibers in tissue samples.[31]

A series of three CMPs was synthesized, each with a single cysteine at the N terminus (Table 2, peptides 1'~3') using conventional Fmoc-mediated solid phase peptide coupling methods.

TABLE 2

| CD Melting Transition Temperatures of CMP Derivatives | | | |
|---|---|---|---|
| Compound | Sequence | SEQ ID NO: | Tm |
| 1 | Cys-(Pro-Hyp-Gly)3 | 20 | — |
| 2 | Cys-(Pro-Hyp-Gly)5 | 21 | 21° C. |
| 3 | Cys-(Pro-Hyp-Gly)7 | 22 | 39° C. |
| 4a | Cys-randomPro7Hyp7Gly7 | 44 | — |

$^a$Cys-GPGP*PP*PPGPPP*GP*P*PP*GP*GG (P* = Hyp)(SEQ ID NO: 44)

A fourth peptide, peptide 4', with an amino acid composition identical to that of peptide 3' but with a scrambled amino acid sequence that is unable to support a triple helical structure was also prepared. The melting transition temperatures (Table 3) of these compounds determined by circular dichroism (CD) spectrometry was consistent with those of other CMP analogs reported previously.[32,33] The citrate reduction method was used to prepare relatively monodisperse gold NPs of diameter 13.2±3.5 nm.[38] Incubating the gold NPs and Cys-CMPs (1'~4') at room temperature produced CMP functionalized gold NPs (Table 3; NP-X, X=1'~4').

TABLE 3

Properties of CMP functionalized Au NPs.

|  | Particle Size by DLS | Measured Peptide layer thickness | Calculated Peptide layer thickness | Number of peptides per NP |
|---|---|---|---|---|
| NP-1 | 17.2 ± 3.7 nm | 2.0 nm | 2.6$^a$ (2.8)$^b$ nm | 582 ± 32 |
| NP-2 | 20.5 ± 3.3 nm | 3.65 nm | 4.3 (4.7) nm | 444 ± 18 |
| NP-3 | 26.9 ± 4.6 nm | 6.85 nm | 6.0 (6.6) nm | 399 ± 21 |
| NP-4 | 16.2 ± 3.1 nm | 1.5 nm | — | 524 ± 59 |

$^a$CMP triple helix,
$^b$poly(proline)-II helix

The melting temperatures of CMPs bound to the NP surfaces could not be determined because circular dichroism measurements were hampered by light scattering from the NPs; calorimetric analysis was unsuccessful due to a trace amount of CMPs present on the NP surfaces. Thermal melting curves as determined by ellipicity of CMPs is shown in FIG. 14. The thickness of the peptide layer on the gold NP surface was determined by dynamic light scattering (DLS) (FIG. 15). The peptide layer thicknesses of NP-1, NP-2 and NP-3 were 2.0 nm, 3.65 nm and 6.85 nm, respectively (Table 3). These values were commensurate with the estimated lengths of the corresponding CMPs in helical conformation.[35] In contrast, the peptide layer thickness of NP-4 was only 1.5 nm, indicating that this peptide was either a random coil or had a distinctively different secondary structure that tended to lie flat on the particle surface.

The average number of CMPs on the NPs was determined by measuring the concentrations of free CMPs remaining in solution after the removal of the NPs from a series of incubation mixtures with varying CMP/NP ratios (FIG. 16 and Table 3).[36] The numbers of CMPs immobilized on the NP surfaces were 582, 444, and 399 for NP-1, NP-2, and NP-3, respectively. These values correspond to the effective footprint areas (per single chain) of 94 Å$^2$, 123 Å$^2$, and 137 Å$^2$, which are comparable to the cross-sectional area of the CMP triple helix, 80 Å$^2$.[35] The peptide layer is likely composed of laterally packed single stranded CMPs. This may have been caused by surface anchoring of the chain ends that prohibited the staggered arrangement of the peptide chains required for the formation of triple helix.

The DLS and average number of peptides per NP data are in agreement with CMPs standing upright on the NP surfaces in an extended conformation that resembles the poly(proline)-II helix. In negatively stained transmission electron microscopy micrographs, the peptides appear as a dense white layer covering the NP surface (FIGS. 17A-17D). All CMP functionalized NPs were able to assemble into a pseudo-hexagonal lattice, indicating that the CMPs fully passivated the NP surfaces and prevented the NPs from aggregating.

The CMP conjugated NPs were highly stable in aqueous solution. No sign of aggregation was detected in buffer solutions of up to 5 M NaCl or within a pH range from 0 to 14 (FIGS. 18A and 18B). All NPs can be freeze-dried and resuspended without aggregation of the particles. Peptides usually make poor passivating layers for NPs and even peptides that are carefully designed to disperse NPs did not protect NPs under such wide range of conditions.[36] CMP triple helices consist of three parallel peptide chains; hence the association of peptides with anti-parallel alignment from two different NPs is unlikely. It is likely that the high Hyp content and extended conformation of the peptides, as shown by DLS, caused the CMPs to mimic the behavior of poly(ethylene glycol) brushes on surfaces and prevent the NPs from aggregating in aqueous solution.

Type I collagen fibers were prepared by adjusting the pH and ionic strength of an acid soluble type I collagen solution.[37] In forming a fiber, collagen molecules aligned head to tail in the direction of the long axis in overlapping rows with a gap between the molecules within each row. Accumulation of staining agents (uranyl acetate) in these gap regions produced dark bands that repeated every 67 nm along the length of the fiber. Compound 3 had the highest melting temperature among the three CMPs, suggesting that it likely makes the most stable adduct with the collagen fiber. Therefore, NP-3 binding to reconstituted collagen fibers was characterized.

When NP-3 or NP-4 was allowed to bind to type I collagen fibers by incubating in a phosphate buffer at 25° C., transmission electron microscopy studies revealed drastically contrasting results. NP-4 exhibited little binding to the collagen fibers, whereas NP-3 was highly attracted to collagen fibers (FIG. 19A, 19B, and 19C). Moreover, NP-3 seemed to bind to defined locations within the gap regions along the fiber axis (FIG. 19C). Due to the large particle size and limitations of transmission electron microscopy resolution, the exact locations of these binding sites could not be determined. Twice as many NP-3 particles per unit area was found in the gap regions (dark bands) than on the overlap regions (light bands) of the collagen fibers. This difference was abolished at incubation temperatures above 40° C. (FIG. 20).

These results indicated that CMP-functionalized NPs bind to the collagen fiber in its native state, possibly at specific locations within collagen molecules, and that the CMP's propensity to form a triple-helix was critical in the binding process. Collagen fibers exhibited clear banding morphology even after incubating with NPs, suggesting that they remained intact. This was not surprising since the incubation temperatures in these experiments was kept below the melting temperature of collagen fibers (65.1° C.).[38] Recent studies using calorimetry and isothermal circular dichroism spectroscopy demonstrated that type I collagen molecules are unstable at body temperature.[39] Miles and Bailey identified three thermally unstable domains in type I collagen that lack helix stabilizing Hyps. Interestingly, all three domains are located within the gap region of the collagen fiber.[29] Without wishing to be bound by theory, it is likely that accumulation of NPs in this gap region indicates a preferential CMP interaction with the thermally labile domains of collagen molecules (FIG. 21). This selectivity in binding is not apparent at higher temperatures since additional thermal energy makes other regions of the molecules unstable and susceptible to invasion by CMPs.

The NP labeling technique may be used to identify structural abnormalities in collagen fibers that are related to debilitating human diseases.[15] Strand invasion or similar forms of strand association by collagen and collagen derivatives may uncover the behaviors of fibril-associated collagens (type IX and XII) and other proteins that incorporate collagen-like sequences.

Example 5

CMP-Containing Hydrogels are Useful for Cartilage Repair

The discovery that collagen mimetic peptides can be used to modified collagen compositions provides for the development of a variety of therapeutic compositions featuring such peptides. For example, collagen mimetic peptides may be used to produce improved biocompatible tissue scaffolds that contain CMP conjugated to biochemically inert polymers. Such scaffolds retain collagens and other extracellular matrix components secreted by the cells cultured within them. Thus, tissue scaffolds containing CMP reproduce a microenvironment that more closely resembles the cell's natural environment than conventional scaffolds (FIG. 22).

Example 6

Acryloyl-PEG-CMP is a Photopolymerizable CMP Derivative

The CMP, (Pro-Hyp-Gly)$_7$-Tyr (SEQ ID NO: 18), was synthesized at greater than 99% purity. Purity was analyzed using MALDI-TOF spectrometry. (ProHypGly)$_7$-Tyr (SEQ ID NO: 18) was selected because the (ProHypGly)$_7$-CMP (SEQ ID NO: 40) unit was shown, as described above, to bind to collagen fiber at physiological temperatures. Tyr was added to the peptide to facilitate the accurate measurement of CMP concentration by UV-Vis spectrophotometer. The peptide was synthesized on a solid support (Wang resin), cleaved, and purified by reverse phase HPLC. The peptide's ability to form a collagen triple helix was confirmed using circular dichroism. The CD trace included a positive peak near 225 nm, a crossover around 215 nm, and a minimum at around 180 nm.

The CD melting temperature (midpoint of CD melting curve) of the (ProHypGly)$_7$-Tyr (SEQ ID NO: 18) CMP was determined to be 38.5° C. This melting temperature is slightly higher than that of the (Pro-Hyp-Gly)$_7$ CMP (SEQ ID NO: 40), which had a melting temperature of 37° C. A similar change in melting temperature was observed when a hydrophobic fluorescence tag was attached to the N-termini of a CMP.

Reaction of the purified (ProHypGly)$_7$-Tyr (SEQ ID NO: 18) CMP with acryloyl-PEG-N-hydroxysuccinimide produced acryloyl-PEG-CMP, a photopolymerizable CMP derivative. A CMP/poly(ethylene oxide) diacrylate (PEODA) hydrogel was prepared by photopolymerizing an aqueous solution containing the acryloyl-PEG-CMP and PEODA monomers (combined weight percent: 10%) as well as a photo reactive initiator (0.05%). Unconjugated reactants were removed using ultrafiltration and gel permeation chromatography. Purity of the final peptide-polymer conjugate was 80% as determined using MALDI-TOF.

Example 7

A CMP/PEODA Hydrogel Retained Added Collagen

To determine whether a CMP/PEODA hydrogel was capable of retaining added collagen, varying concentrations of type I collagen were added to the initial CMP/PEODA polymer solution. The solution was then exposed to UV radiation to produce a hydrogel and the hydrogel was incubated for one week in PBS buffer. The incubation in PBS provided an opportunity for the collagen to leach out of the hydrogel. Following the incubation in PBS buffer, the hydroxyproline content of the hydrogel was assayed. Hydroxyproline content is used to measure the presence of collagen. Hydroxyproline content in the CMP containing hydrogel was significantly greater than that observed in control gels that did not contain CMP (FIG. 23). The amount of collagen retained by the CMP/PEODA hydrogel reached saturation when the gel was incubated with 0.2 mg/mL of collagen. The amount of collagen retained did not increase when 0.5 mg/mL of collagen was added to the CMP/PEODA hydrogels.

Example 8

CMP Containing Hydrogels have Increased Water Content

Water content of a hydrogel is closely correlated to crosslinking density and mesh size of the scaffold. The water content of hydrogels with and without CMP was determined following a twenty-four hour equilibration in chondrocyte medium. The wet and dry weights of gels crosslinked with various concentrations of collagen mimetic peptides was measured and the water content of each hydrogel was determined. Hydrogels crosslinked to CMP contained 10% more water than hydrogels that did not contain CMP (Table 4).

TABLE 4

| Water content of hydrogels as a function of CMP concentration | | |
|---|---|---|
| Percentage of CMP (%) | Water Content (Q, %) | S.D. |
| 0 | 82.963 | 0.11401 |
| 0.1 | 90.355 | 0.22550 |
| 0.5 | 90.444 | 0.30966 |
| 1 | 90.608 | 3.3092 |
| 2 | 90.844 | 0.60216 |

Water content was significantly higher in the CMP/PEODA hydrogels relative to the PEODA hydrogel. This was not surprising because a single PEG-CMP molecule is crosslinked to each PEODA molecule the hydrogel containing CMP has a lower crosslinking density than the hydrogel without CMP.

Little difference in water content was observed in CMP/PEODA hydrogels containing greater than 0.1% of ACRL-PEG-CMP. In fact, hydrogels containing 0.1-2% CMP all had similar water contents (approximately 90% water). This may be a result of CMP's tendency to associate with and form triple helixes with other CMPs. Since the triple helix brings together three separate chains to form a single complex, these association effectively crosslink the hydrogel and may affect the swelling characteristics of the gel.

Example 9

A CMP/PEODA Hydrogel Supported Cell Survival

To determine whether the peptide-polymer conjugate was capable of supporting cell survival, chondrocytes were harvested and encapsulated in control, 1%, and 2% CMP/PEODA hydrogels. The CMP containing hydrogel successfully supported cell survival as shown by a cell viability assay (FIG. 24). Moreover, cell viability was homogenous throughout the CMP/PEODA gels (FIG. 24).

Example 10

A CMP/PEODA Hydrogel Retained Cell-Secreted Collagen

Cartilage is mainly comprised of collagen and proteoglycans. Collagen is a good marker of the cultured chondrocyte's biosynthetic capability because collagen is the most abundant extracellular matrix component in cartilage. The collagen produced by chondrocytes is mostly type II collagen. Type II collagen is also expected to physically interact with CMP. To determine whether the collagen secreted from the encapsulated cells bound to the CMP/PEODA hydrogel, collagen content present in the hydrogel was assayed following one week of chondrocyte culture. Collagen content was 37% higher in the 2% CMP/PEODA hydrogel than in the 1% CMP/PEODA hydrogel. Total collagen production was CMP dose dependent and for the 2% CMP/PEODA gel, the ratio of collagen content in the two gel (PEODA:2% CMP/PEODA=1:2) was comparable to that determined from the model collagen retention experiment. Only negligible amounts of collagen were detected in acellular hydrogels.

Example 11

Cells Grown in CMP/PEODA Hydrogel Secreted Extracellular Matrix Components that were Retained by the Hydrogel Production of extracellular matrix components, such as collagen and glycosaminoglycan, is indicative not only of cell viability, but also of functionality. Histological evaluation was used to determine whether encapsulated chondrocyte cells were distributed evenly throughout of the hydrogel and whether the cells were secreting extracellular matrix components (FIG. 17). To determine whether chondrocytes were producing glycosaminoglycan (GAG), which is a component of the extracellular matrix, GAG content in the hydrogel was assayed following two weeks of culture. GAG is a hydrophilic polysaccharide unit attached to proteoglycans that, in combination with collagen, is a major constituent of cartilage extracellular matrix. GAG synthesis in the 2% CMP/PEODA hydrogel was significantly greater than that in the 1% CMP/PEODA hydrogel and control PEG gel, by 105% and 87%, respectively. However, there was no significant difference in GAG production between the control and 1% CMP/PEODA hydrogel.

The total GAG assay indicated that the GAG production was not influenced by the presence of 1% PEODA-CMP in the hydrogel, even though the PEODA-CMP hydrogel had significantly higher water content than PEODA. Typically, increasing the water content of a hydrogel increases the tissue remodeling ability at the expense of mechanical properties. The mechanical strength of the hydrogel is weakened but due to higher water content, cell can take up nutrients easily and produce high levels of ECM. This was not observed in the CMP/PEODA hydrogel. Although 1% and 2% CMP/PEODA had similar water content, the GAG content of 2% CMP/PEODA was 1.9 times higher than that of the 1% CMP/PEODA. This indicates that the increase in GAG production was not the result of an increase in water content.

Proteoglycan deposition was also examined using safranin-O staining. The intensity of safranin-O staining was highest in the 2% CMP/PEODA gels, and was next highest in the 1% CMP/PEODA hydrogel. Total collagen staining in the CMP/PEODA hydrogel was also examined using Masson's Trichrome stain. The CMP/PEODA hydrogel was more intensely stained than the PEODA gel. No difference in staining intensity was observed in hydrogel's containing varying CMP concentrations. No staining was observed in a control acellular CMP/PEODA hydrogel. Immunohistochemical staining for collagen type II also showed strong positive staining in 1% and 2% CMP/PEODA hydrogels (FIG. 26).

Chondrocytes produce the matrix material and the collagen fibers present in bone. As the chondrocytes secrete matrix material around them, they become walled off into small chambers or lacunae. The chondrocytes embedded in the hydrogel had a spherical morphology and were present in isolated pockets resembling lacunae. Immediately surrounding the lacunae was a territorial matrix where newly synthesized ECM products were present. Heavy staining for collagen (both total collagen staining and type II collagen immunostaining) was observed in the territorial regions of the CMP/PEODA hydrogel indicating that the cell-secreted collagen remains in the chondrocytes microenvironment. It is likely that the high collagen concentration around the chondrocytes simulated a more natural microenviroment for the cells and enhanced its productivity of GAG and possibly other ECM molecules. GAG immunostaining was not confined to areas immediately surrounding the cell, suggesting that GAGs are capable of diffusing through the hydrogel. This is not surprising because CMP has no affinity for GAGs. There was enhanced matrix production in CMP/PEODA hydrogel. This may be the result of either collagen retention or an upregulation in gene expression.

Collagen synthesis in the 1% and 2% CMP/PEODA hydrogels was 47% and 103% respectively. Chondrocytes in CMP-containing hydrogels synthesized more collagen than chondrocytes in control hydrogels lacking CMP. Tissue formation was greater in CMP/PEODA hydrogels. Results of the biochemical assays of chondrocyte-encapsulated hydrogel were consistent with the histological findings (FIG. 27). DNA contents were similar in all samples. The high initial density of chondrocytes prevented their proliferation in the hydrogel.

In sum, the results reported herein indicate that CMP/PEODA hydrogel provides an effective scaffold for cartilage regeneration that is superior to existing tissue scaffolds. Given these results, CMP/PEODA hydrogels are useful for the repair of damaged cartilage, and are particularly useful for applications involving the repair of articular cartilage.

Example 12

Reduction of Thrombus Deposition by Applying CMP Derivatives

Angioplasty denudes the vessel wall of the endothelial layer. Vessel healing is often accompanied by the overproliferation of smooth muscle under the endothelial layer. This process can narrow or even block blood vessels causing thrombosis formation[40]. Methods for preventing intimal hyperplasia and thrombosis subsequent to angioplasty are urgently required. The present invention provides a method of treating blood vessel injury using CMP to deliver anti-thrombotics. CMP may be conjugated to virtually any anti-thrombotic agent known in the art. Such agents include aspirin, thienopyridine, heparin, saratin (a 12,000 Da recombinant protein isolated from the saliva of the medicinal leech *Hirudo medicinalis*), hirudin (a 65 amino-acid polypeptide), pegylated hirudin, and unfractionated heparin (UH).

Desirably CMP-anti-thrombotic conjugates bind collagen (type III)[49] and repel cell attachment. Saratin-CMPs, hirudin-CMPs, and PEG-CMPs are produced using standard methods and purified using HPLC. Purified conjugates are then characterized using MALDI-TOF and CD analysis as described herein. The activity of the CMP conjugates will be assessed in anti-platelet activation and anti-thrombin formation assays. Specifically, plasma levels of β-thromboglobulin (β-TG) and thrombin-antithrombin complexes (T-AT) will be determined using immunoenzymoassays[50]. Optionally, the activity of CMP-anti-thrombotic conjugates are assessed in animal experiments.

In particular embodiments, the following CMP conjugates are employed as anti-thrombotics.

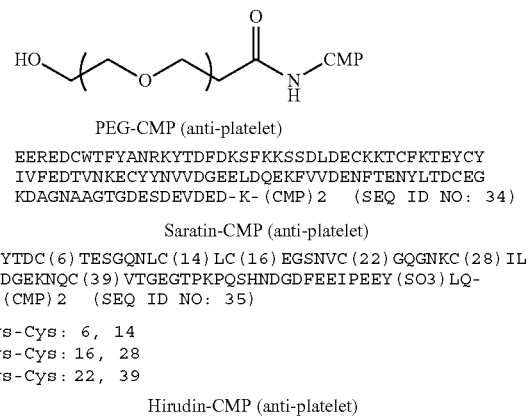

PEG-CMP (anti-platelet)

EEREDCWTFYANRKYTDFDKSFKKSSDLDECKKTCFKTEYCY
IVFEDTVNKECYYNVVDGEELDQEKFVVDENFTENYLTDCEG
KDAGNAAGTGDESDEVDED-K-(CMP)2  (SEQ ID NO: 34)

Saratin-CMP (anti-platelet)

LTYTDC(6)TESGQNLC(14)LC(16)EGSNVC(22)GQGNKC(28)IL
GSDGEKNQC(39)VTGEGTPKPQSHNDGDFEEIPEEY(SO3)LQ-
K-(CMP)2   (SEQ ID NO: 35)

Cys-Cys: 6, 14
Cys-Cys: 16, 28
Cys-Cys: 22, 39

Hirudin-CMP (anti-platelet)

Materials

Fmoc-amino acids were purchased from Advanced ChemTech (Louisville, Ky.) and Fmoc-Gly-Wang resin was purchased from Novabiochem (La Jolla, Calif.). Acid soluble, type I bovine collagen was purchased from Sigma (St. Louis, Mo.) and mPEG$_{2000}$-Gly$_3$-(ProHypGly)$_7$ (SEQ ID NO: 6) (peptide 5) was purchased from Genscript Corporation (Piscataway, N.J.). All other chemicals were purchased from Sigma-Aldrich and used without further purification. Fibroblast (CRL-1502) cells and breast epithelial cells (MCF-7) were from ATCC (Manassas, Va.). Dulbecco's modified eagle's medium (DMEM) and Iscove's modified Dulbecco's medium (IDMM) were purchased from Invitrogen Corporation (Carlsbad, Calif.). TEM images were acquired on a Philips 420 EM using holey carbon grids from Ted Pella Inc (Redding, Calif.). UV-Vis spectra were measured in a Cary 50 Bio spectrophotometer. Thermal melting transition measurements were performed in a Jasco 710 spectropolarimeter. DLS data was acquired on a Malvern Zetasizer 3000.

Synthesis and Purification of Collagen Mimetic Peptides (CMPs)

The peptides were synthesized by condensation of the corresponding Fmoc-amino acids (Fmoc-Gly-OH, Fmoc-Hyp-OH, and Fmoc-Pro-OH) and 5-carboxyfluorescein (5CF) on a solid support (Wang resin). Both manual and automated systems (Applied Biosystems 431A Peptide Synthesizer) were used to prepare peptides 1-4. Four-fold molar excess of the above amino acids was used in a typical coupling reaction. Fmoc-deprotection was accomplished by treatment with 20% (v/v) piperidine in dimethyl formamide (DMF) for 1 hour. The coupling was achieved by treatment with 2-(1H-benzotriazole-1-yl)-1,1,3,3-tetramethyluronium hexafluorophosphate (HBTU) in N,N-diisopropylethylamine (DIPEA). All the coupling reactions were completed within 3-4 hours and were monitored by ninhydrin or chloranil tests.

The CMPs were cleaved from the resins by treatment with water/triisopropylsilane/trifluoroacetic acid (2.5:2.5:95) for 3 hours. The crude CMPs were precipitated with cold ether and dried. Reverse-phase HPLC purification was performed on a Varian Polaris 210 series Liquid Chromatograph with a Vydac C-18 reversed-phase column at a flow rate of 1 ml/min. The purified peptides were analyzed by a matrix-assisted laser desorption/ionization time-of-flight (MALDI-TOF) mass spectrometer (Kompact SEQ, KRATOS or Voyager DE-STR, Applied Biosystems). (M+H)$^+$=(peptide 1, 2690.7 Da; peptide 2, 3220.23 Da; peptide 3, 3221.65 Da; peptide 4, 2296.0 Da; peptide 5, 4305.1 Da).

Circular Dichroism Measurements

Circular dichroism (CD) spectra were recorded on JASCO 710 spectrometer equipped with JASCO PTC-348 WI temperature controller and Hellma cell (400 μL, 0.1 mm pathlength). The thermal melting curves were obtained by measuring the molar ellipticity at 225 nm with 1° C./min heating rate. All samples (57 μM in 50 mM acetic acid) were stored at 4° C. for 24 hours before the CD measurement.

CMP-Collagen Film Affinity Study

To each well of a 96-well culture plate was added 200 μl of saturated collagen (acid soluble, type I bovine) solution in 0.5 M acetic acid. The culture plate was air-dried to form transparent collagen films. The films were neutralized with 0.01 M potassium phosphate buffer (pH 7.4), and washed with distilled water. To the collagen-coated wells were added 40 μl of 0.01 M potassium phosphate solutions (pH 7.4) containing 50 μM of either CF (5-carboxyfluorescein), FITC-Dextran, and peptides 2, 3, or 4, which were pre-equilibrated at 25° C. or 80° C. After 3 hours of incubation at room temperature, the wells were washed with 0.01 M potassium phosphate buffer solution (pH 7.4) and observed by fluorescence microscope (Eclips ME 600, Nikon Corp). The total fluorescence intensity was acquired from the fluorescence micrographs using Meta Imaging Series V4.5, (Universal Imaging Corporation, Downingtown Pa.). Average values of four independent experiments are reported.

Helical Content Estimation of the Modified Collagen Films.

Collagen (type I, bovine) film was treated with either peptide 2 solution or blank buffer solution as described before. After 3 hr of incubation at room temperature, the wells were washed with 0.01 M potassium phosphate buffer solution (pH 7.4) and deionized water. All samples were dissolved in 50 mM acetic acid to a concentration of 1.80 μM or 3.60 μM and stored at 4° C. for 24 hours before the CD measurement. Average values of four independent experiments are reported (FIG. 4).

TEM Analysis of the Modified Collagen Fibers

Collagen fibers were prepared by dialysis of collagen in 0.01M acetic acid solution against dilute NaCl solution. Peptide 4 in potassium phosphate buffer (400 μl, 500 pH 7.4) was added to the collagen fibers in the PBS buffer (1' ml, 1 mg/ml, pH 7.4). The mixture was incubated for 3 hours and excess peptide 4 was removed by repeated centrifugation. The collagen fibers were resuspended in deionized water and transferred to a TEM grid. Uranyl acetate was used to stain the collagen fiber. (FIG. 6)

Cell (Human Fibroblasts and Breast Epithelial Cells) Adhesion Study

To the collagen film (prepared as above) was added 10 μl of peptide 5 solution (2 mM in pH 7.4 potassium phosphate buffer). The film was allowed to dry and excess materials were removed by washing with potassium phosphate buffer (pH 7.4, 50 mM) and culture medium (DMEM or IDMM). Cells were added to the culture well and incubated at room temperature for 30 minutes. Human fibroblasts (CRL-1502) were seeded at 4.5×10$^5$ cell/ml cell density in DMEM and breast epithelial cells (MCF-7) at 5.6×10$^5$ cells/ml density in cell culture media (IDMM). The nonattached cells were removed by rinsing the well three times with growth medium and PBS buffer. The remaining cells were incubated at 37° C. (5% CO$_2$) for three days. The growth medium was exchanged after 48 hours.

Synthesis of Gold Nanoparticles.

Gold nanoparticles were synthesized by citrate reduction method according using standard methods.[41] Briefly, tri-sodium citrate solution (25 mL, 38.8 mM) was quickly added to a refluxing aqueous solution of HAuCl$_4$ (250 mL, 1 mM) with vigorous stirring. The color of the solution changed from pale yellow to deep red after adding the citrate solution. The solution was refluxed for an additional 15 minutes, cooled, and filtered through a glass filter.

Synthesis and Purification of CMPs.

CMP 1'~4' were synthesized and purified as described above.[42]

Thermal Melting Curves of CMPs.

The thermal melting curves were obtained by measuring the ellipticity of peptide in deionized (DI) water (0.5~2 mM) at 225 nm with 0.1° C./min heating rate. All samples were stored at 4° C. for 24 hours before the measurement. (FIG. 15)

Surface Functionalization of Gold NP with Cys-CMPs.

Purified Cys-CMP (peptides 1'~4') (0.5 mL, 500 µM) was added to gold nanoparticle solution (5 mL, 17 nM), and the reaction mixture was incubated at room temperature for twenty-four hours. Excess CMPs were removed by repeated centrifugation and washing in deionized water. The DLS results of NP-Xs are shown in FIG. 16.

Stability of NP-Xs.

The aggregation parameter (AP) is defined as follows: $AP=(A-A_0)/A_0$, where A is the integrated absorbance between 600 and 700 nm of a sample at a given condition, and $A_0$ is the integrated absorbance of a fully dispersed NP solution.[3]

Regeneration of Type I Collagen Fibers.

Collagen fibers were regenerated by mixing 0.5 mL of acid soluble type I collagen (1 mg/mL) in 50 mM acetic acid solution with 1 mL of sodium phosphate buffer (10 mM, pH 8.25). The mixture was incubated at room temperature for 12 hours.

Tem Analysis of NP-3 Decorated Collagen Fibers.

A drop (8 µL) of type I collagen solution (0.3 mg/mL in PBS containing 1% BSA) was added to a holey carbon TEM grid. NP-3 solution (3 nM in PBS containing 1% BSA) was added to the grid and incubated for 5 minutes at room temperature or at 40° C., followed by washing with deionized water. The collagen fibers were stained with uranyl acetate (1%).

Measurement of Number of Peptides Per NP (Passivation Number).

Seven 10 µM Cys-CMP solutions with varying concentrations of citrate-stabilized gold NP (2~14 nM) were prepared. The mixtures were incubated for 2 hours at 25° C. and the gold NPs were removed by centrifugation. The concentrations of free peptides remaining in the supernatant were determined from the UV-Vis absorbance at 215 nm with citrate ion background subtraction. The number of peptides per Au NP was calculated from the slope of the linear fit of the data points. (FIG. 17)

Synthesis and Purification of Collagen Mimetic Peptide (CMP)

(Pro-Hyp-Gly)$_7$-Tyr (SEQ ID NO: 18), CMP, was synthesized by Fmoc mediated solid phase peptide coupling methods starting from a tyrosine preloaded Wang resin. High performance liquid chromatography (HPLC: C18 Vydac column) was used to purify the peptide. The peptide product was lyophilized and stored at −20° C. The molecular weight of the product was confirmed by Matrix-assisted laser-desorption ionization time-of-flight mass spectrometry (MALDI-TOF MS, Voyager DE-STR, Applied Biosystems).

Triple-helical conformation of the CMP was confirmed by circular dichroism (CD) spectroscopy. Peptide samples (250 or 500 µM) were prepared in distilled water and incubated at 4° C. overnight before the CD measurement. CD was recorded between 180 and 280 nm on a JASCO 710 CD spectrometer at various temperatures under a nitrogen flow. Each measurement had static equilibrium time of 30 minutes.

Synthesis and Purification of Acryloly-PEG-Peptide

One milligram (4.9 µM) of (Pro-Hyp-Gly)$_7$-Tyr (SEQ ID NO: 18) was dissolved in 1 ml of 0.05 M sodium bicarbonate solution. Acryloyl (ACRL)-PEG-peptide was prepared as previously described[44]. Briefly, acryloyl-PEG-N-hydroxysuccinimide (ACRL-PEG-NHS, Nektar, 3.4 mg, 10 µM) was dissolved in 200 µL of 0.05 M sodium bicarbonate solution and the resulting solution was added drop-wise to the CMP solution. The solution was shaken on an orbital shaker for 2 hours at room temperature. Ultrafiltration (Millipore, molecular weight cut off=3500) was used to remove unreacted CMP and ACRL-PEG-NHS, and the solution containing the pure product was lyophilized. The dried powder was dissolved in deionized water and run through a size exclusion column Sephadex® G-25 (Pharmacia, motive phase: deionized water) to remove small molecule impurities. Elution fractions containing the target product were combined and lyophilized. MALDI-TOF was used to confirm the molecular weight of the target product. Product was stored at −20° C. and used within a week.

Collagen Encapsulation in Hydrogels

Type I collagen in 0.1 N acetic acid (Sigma) was neutralized and resuspended in macromer solutions (0.05 wt % initiator (D-2959, Ciba), 8 wt % PEODA (molecular weight: 3400, Nektar) and 2% of ACRL-PEG-(Pro-Hyp-Gly)$_7$-Tyr) (SEQ ID NO: 45) at a concentration of 0.2 or 0.5 mg/ml. Control samples composed of 10 wt % PEODA were also prepared. Ultraviolet lamp (EXFO Acticure 4000; wavelength: 365 nm; intensity 5 mW/cm$^2$; 5 min. exposure time) was used to photopolymerize 100 µL of the macromer collagen solution mixture. The polymerized gel constructs were transferred to 12 well tissue culture plates with each well containing 2 ml PBS buffer. The culture plate was incubated at 37° C. in 5% CO$_2$ atmosphere, and PBS buffer was replaced every 2-3 days for one-week period.

Collagen Assay

After one week of incubation, the wet weight and dry weight of collagen-encapsulated hydrogel was determined by measurement of the hydrogel before and after 48 hours of lyophilization, respectively. A dry construct was digested in 900 ml of papain solution (250 µg/ml papain type II (Worthington Biomedical Corporation, Lakewood, N.J.), 100 mM phosphate buffer, 10 mM EDTA, 10 mM cysteine at pH 6.3) for overnight at 60° C. The digests were then centrifuged at 10,000 rpm for 5 minutes, and supernatants were taken.

Total collagen content of the gel was estimated from the hydroxyproline assay conducted with papain-digested solution after overnight hydrolysis reaction with 6N hydrochloric acid at 115° C.[45]. Hydrolyzed samples were reacted with p-dimethylamino benzaldehyde and chloramines-T hydrate[46]. Absorbance was measured at 550 nm on a UV-Vis spectrophotometer. Standard curve was generated using pure trans-4-hydroxy-L-proline (Sigma-Aldrich). Collagen content of the blank gel (no collagen) was determined and subtracted in the calculation of the total collagen content.

Chondrocyte Isolation and Encapsulation

Chondrocytes were isolated from the femoral patellar groove and femoral condyles of three 5- to 8-week-old calves. The articular cartilage was excised under aseptic conditions and digested overnight at 37° C. in 0.2% Collagenase type II (Gibco) and 5% fetal bovine serum (FBS, Gibco, Carlsbad, Calif.) in Dulbecco's modified Eagle medium (DMEM, Gibco). The digested suspension was filtered through a cell strainer (Fisher Scientific Co.) and centrifuged at 1500 rpm for 10 minutes. The supernatant was removed and the pellet was washed and resuspended in PBS buffer (Gibco) supplemented with 1% penicillin-streptomycin (Gibco). The pellet was washed twice and resuspended in medium.

Harvested cells were resuspended in the macromer solutions at a concentration of $20\times10^6$ per ml. For example, macromer solutions for 2 wt % CMP-PEG gel contained initiator (0.05 wt %; D-2959, Ciba), PEODA (8 wt %; Nektar), ACRL-PEG-(Pro-Hyp-Gly)$_7$-Tyr (SEQ ID NO: 45) (2 wt %) and PBS buffer (89.95 wt %). Each gel-construct was prepared in 100 µL cell-macromer solution and photopolymerized as described previously. The construct was transferred to a well of 12-well culture plate containing 2 ml of culture medium. The medium was composed of 10 mM HEPES (Gibco, Carlsbad, Calif.), 0.1 mM NEAA (Gibco, Carlsbad, Calif.), 0.4 mM proline (Sigma), 50 mg/L Vitamin C (Sigma), 10% FBS, and 1% penicillin-streptomycin in high glucose DMEM. Constructs were cultured at 37° C. in 5% $CO_2$ atmosphere and medium was replaced every 2-3 days.

Cell Viability Test

The viability of hydrogel encapsulated cells was determined after 2 weeks of culture. The medium was discarded and the hydrogel matrices were washed twice with phosphate buffer solution (PBS, Gibco, Carlsbad, Calif.). Cell viability was assessed based on the integrity of cellular membrane using Live/Dead Viability/Cytotoxicity Kit (Molecular Probes, Eugene, Oreg.) that contains calcein-AM ("Live") dye and ethidium homodimer-1 ("Dead") dye. Dye solution was made with 0.5 µL of calcein-AM dye and 2 µl of ethidium homodimer-1 dye in 1 mL DMEM. A slice of the cell containing matrix was incubated in 500 µL of the "Live/Dead" dye solution for 30 minutes. Fluorescence microscopy was performed using a fluorescein optical filter (485±10 nm) for calcein-AM and a rhodamine optical filter (530±12.5 nm) for ethidium homodimer-1.

Histology and Immunohistochemistry

After two weeks of culture, cell containing and control matrices were fixed overnight in 10% formalin solution and stored in 70% ethanol. The fixed cell containing matrix was embedded in paraffin, sectioned and stained with Safranin-O/fast green or with Masson's trichrome stain. Acellular controls of the CMP/PEODA hydrogel were also stained following the same procedure to measure any background signals. Immunohistochemistry was performed using rabbit polyclonal antibody to collagen type II (Research Diagnostics) and a Histostain-SP kit (Zymed).

Water Content and Biochemical Assays

Water content of the cell-encapsulated hydrogels was calculated by the following equation:

$$\text{Water content (\%)} = [(W_w - W_d)/W_w] \times 100 \quad (1)$$

where $W_w$ is wet weight of the hydrogel after one day equilibration in water, and $W_d$, dry Weight of the hydrogel.

Cell containing and control matrices were digested with Papain overnight. The digested samples were used for both DNA and glucosaminoglycan (GAG) measurements. Hoechst 33258 dye from Molecular Probes (Eugene, Oreg.) was used for the DNA assay[47]. The solution (0.1 µg/ml) was prepared in 1×THE buffer (10 mM Tris, 1 mM EDTA, 0.2 M NaCl, pH 7.4). Calf Thymus DNA standards were prepared with 0 to 100 µg/ml DNA. Papain-digested samples (30 or 60 µL) or standards were mixed with the prepared dye solution. DNA content was measured with a fluorometer (365 nm excitation and 458 nm emission) and calculated from the calf thymus DNA standard curve. The GAG was measured using the dimethylmethylene blue (DMMB) dye[48]. A standard curve was created with chondroitin sulfate C (shark cartilage extract, Sigma). Absorbance was measured at 525 nm on a UV-Vis spectrophotometer. Collagen assays were also performed as described above. Collagen contents in the acellular CMP hydrogels were also measured for the purpose of background subtraction. GAG and collagen contents from the biochemical assays were normalized by the DNA content. The value is presented as mean±standard deviation. Statistical significance was determined by unpaired Student t test and set as $p<0.05$.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

1. Leikina, et al., (2002) Proc. Natl. Acad. Sci. 99:1314-1318.
2. Holmgren, et al., "(1998) Nature 392:666-667.
3. Goodman, et al., (1998) Biopolymers 47:127-142.
4. Stetefeld, et al., (2003) Structure (Camb) 11(3):339-46.
5. Holmgren, et al., (1999) Chem Biol. 6:63-70.
6. Frank, et al., (2001) J. Mol. Biol. 308:1081-1089.
7. Frank, et al., (2003) The Journal of Biological Chemistry 278(10):7747-7750.
8. Koide, et al., (2005) Bioorganic & Medicinal Chemistry Letters 15:5230-5233.
9. Huynh, et al., (1999) Nat. Biotechnol. 17:1083-1086.
10. O'Connor, et al., (2000) J. Neurosci. Methods 102:187-195.
11. Myles, ET AL., (2000) J. Biomater. Sci. Polym. Ed. 11:69-86.
12. Huang, et al., (2001) J. Biomater. Sci. Polym. Ed. 12:979-993.
13. Koide, et al., (2005) Bioorganic & Medicinal Chemistry Letters 15:5230-5233.
14. Winblade, et al., (2002) J. Biomed. Mater. Res. 59:618-631.
15. Groll, et al., (2005) Biomacromolecules 6:956-962.
16. Groll, et al., (2005) J. Biomed. Mater. Res. 74A:607-617
17. Wang, et al., (2005) J. Am. Chem. Soc. 127: 4130-4131.
18. Groll, et al., (2004) J. Am. Chem. Soc. 126: 4234-4239.
19. Pasut, et al., (2004) Expert Opin. Ther. Patents 14(6):859-894.
20. Ameringer, et al. (2005) Biomacromolecules 6:1819-1823.
21. Petersen, et al., (2002) Biomacromolecules 3:926-936.
22. Fitzgerald, et al., (2003) FEBS Lett., 552:91-94.
23. Olsen, (1997) Int. J. Biochem. Cell Biol. 29:555-558.
24. Kassner, et al., (2004) S. J. Mol. Biol. 339: 835-853.
25. Gelse, et al., (2003) Advanced Drug Delivery Reviews 55:1531-1546.
26. Harris, et al., (1997) ACS Symposium Series 680; Amer. Chem. Soc.: San Francisco.

27. Bretscher, et al, (2001) R. T. J. Am. Chem. Soc. 123:777-778.
28. Peffer, et al., (1993) Proc. Natl. Acad. Sci. 90:10648-10652.
29. Miles, et al., (2001) J. Micron 32:325-332.
30. Nimni, (1998) M. E. Collagen; CRC Press: Boca Raton.
31. Birk, et al., (1988) J. Cell. Biol. 106:999-1008.
32. Feng, et al., (1996) Biopolymers 39:859-872.
33. Bretscher, et al., (2001) J. Am. Chem. Soc. 123:777-778.
34. Grabar, et al., (1995) J. Anal. Chem. 67: 735-743.
35. Bella, et al., (1994) Science 266:75-81.
36. Levy, et al. (2004) J. Am. Chem. Soc. 126:10076-10084.
37. Williams, et al. (1978) J. Biol. Chem. 253:6578-6585.
38. Miles, et al. (1999) Biophys. J. 76:3243-3252.
39. Leikina, et al., (2002) S. Proc. Nat. Acad. Sci. 99:1314-1318.
40. Cruz., et al., (2001) J. Vasc. Surg. 34:724-729.
41. Grabar, et al., (1995) J. Anal. Chem. 67:735-743.
42. Wang, et al., (2005) J. Am. Chem. Soc. 127:4130-4131.
43. Levy, et al., (2004) J. Am. Chem. Soc. 126:10076-10084
44. Hern, et al., (1998) J Biomed Mater Res 39:266.
45. Neuman, et al., (1950) J Biol Chem 184:299.
46. Woessner, (1961) Arch Biochem Biophys 93:440.
47. Kim, et al., (1988) Anal Biochem 174:168.
48. Melrose, et al. (1988) Anal Biochem 170:293.
49. Liu, et al., (1997) Proc. Natl. Acad. Sci. U.S.A. 94:1852-1856.
50. Bossavy, et al., (1999) Arterioscler Thromb Vasc. Biol. 19:1348-1353.

What is claimed is:

1. A method for modifying collagen, the method comprising contacting collagen with a collagen mimetic peptide consisting of Z-[X-Y-Gly]$_{2-20}$ repeat unit (SEQ ID NO:1), wherein Z is any amino acid, X is proline or modified proline, Y is proline or modified proline, under conditions that provide for a physical interaction between the collagen and the collagen mimetic peptide.

2. The method of claim 1, wherein Z, X, and/or Y is modified proline.

3. The method of claim 1, wherein the collagen mimetic peptide is conjugated to an antibiotic, a cell adhesion molecule, a contrast agent, a detectable label, a growth factor, a component of the extracellular matrix, an anti-inflammatory agent, a polymer, polyethylene glycol (PEG), or a small molecule.

4. A method for modifying collagen, the method comprising contacting collagen with a collagen mimetic peptide consisting of an amino acid sequence selected from the group consisting of:

Gly$_3$-(ProHypGly)$_6$, (SEQ ID NO:13)
Gly$_3$-(ProHypGly)$_7$, (SEQ ID NO:14)
Gly$_3$-(ProHypGly)$_8$, (SEQ ID NO:15)
Gly$_3$-(ProHypGly)$_9$, (SEQ ID NO:16)
(ProHypGly)$_6$-Tyr, (SEQ ID NO:17)
(ProHypGly)$_7$-Tyr, (SEQ ID NO:18)
(ProHypGly)$_8$-Tyr, (SEQ ID NO:19)
Cys-(Pro-Hyp-Gly)$_3$, (SEQ ID NO:20)
Cys-(Pro-Hyp-Gly)$_5$, (SEQ ID NO:21) and
Cys-(Pro-Hyp-Gly)$_7$ (SEQ ID NO:22) under conditions that provide for a physical interaction between the collagen and the collagen mimetic peptide.

5. The method of claim 2, wherein the modified proline is 4-hydroxyproline or 4-fluoro proline.

6. The method of claim 1, wherein [X-Y-Gly] is (Pro-HypGly), (ProProGly), or (ProFlpGly), where Hyp is hydroxyproline and Flp is 4-fluoroproline.

* * * * *

SEQUENCE LISTING

```
<160> NUMBER OF SEQ ID NOS: 51

<210> SEQ ID NO 1
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(3)
<223> OTHER INFORMATION: Proline or modified proline
<220> FEATURE:
<221> NAME/KEY: MISC_FEATURE
<222> LOCATION: (2)..(61)
<223> OTHER INFORMATION: This region may encompass 1-20 repeating "Pro
      Pro Gly" units
<220> FEATURE:
<221> NAME/KEY: MOD_RES
<222> LOCATION: (5)..(6)
<223> OTHER INFORMATION: Proline or modified proline
<220> FEATURE:
<221> NAME/KEY: MOD_RES
<222> LOCATION: (8)..(9)
<223> OTHER INFORMATION: Proline or modified proline
<220> FEATURE:
<221> NAME/KEY: MOD_RES
<222> LOCATION: (11)..(12)
<223> OTHER INFORMATION: Proline or modified proline
<220> FEATURE:
<221> NAME/KEY: MOD_RES
<222> LOCATION: (14)..(15)
<223> OTHER INFORMATION: Proline or modified proline
<220> FEATURE:
<221> NAME/KEY: MOD_RES
<222> LOCATION: (17)..(18)
<223> OTHER INFORMATION: Proline or modified proline
<220> FEATURE:
<221> NAME/KEY: MOD_RES
<222> LOCATION: (20)..(21)
<223> OTHER INFORMATION: Proline or modified proline
<220> FEATURE:
<221> NAME/KEY: MOD_RES
<222> LOCATION: (23)..(24)
<223> OTHER INFORMATION: Proline or modified proline
<220> FEATURE:
<221> NAME/KEY: MOD_RES
<222> LOCATION: (26)..(27)
<223> OTHER INFORMATION: Proline or modified proline
<220> FEATURE:
<221> NAME/KEY: MOD_RES
<222> LOCATION: (29)..(30)
<223> OTHER INFORMATION: Proline or modified proline
```

```
<220> FEATURE:
<221> NAME/KEY: MOD_RES
<222> LOCATION: (32)..(33)
<223> OTHER INFORMATION: Proline or modified proline
<220> FEATURE:
<221> NAME/KEY: MOD_RES
<222> LOCATION: (35)..(36)
<223> OTHER INFORMATION: Proline or modified proline
<220> FEATURE:
<221> NAME/KEY: MOD_RES
<222> LOCATION: (38)..(39)
<223> OTHER INFORMATION: Proline or modified proline
<220> FEATURE:
<221> NAME/KEY: MOD_RES
<222> LOCATION: (41)..(42)
<223> OTHER INFORMATION: Proline or modified proline
<220> FEATURE:
<221> NAME/KEY: MOD_RES
<222> LOCATION: (44)..(45)
<223> OTHER INFORMATION: Proline or modified proline
<220> FEATURE:
<221> NAME/KEY: MOD_RES
<222> LOCATION: (47)..(48)
<223> OTHER INFORMATION: Proline or modified proline
<220> FEATURE:
<221> NAME/KEY: MOD_RES
<222> LOCATION: (50)..(51)
<223> OTHER INFORMATION: Proline or modified proline
<220> FEATURE:
<221> NAME/KEY: MOD_RES
<222> LOCATION: (53)..(54)
<223> OTHER INFORMATION: Proline or modified proline
<220> FEATURE:
<221> NAME/KEY: MOD_RES
<222> LOCATION: (56)..(57)
<223> OTHER INFORMATION: Proline or modified proline
<220> FEATURE:
<221> NAME/KEY: MOD_RES
<222> LOCATION: (59)..(60)
<223> OTHER INFORMATION: Proline or modified proline

<400> SEQUENCE: 1

Xaa Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro Gly Pro
                20                  25                  30

Pro Gly Pro Pro Gly Pro Pro Gly Pro Pro Gly Pro Pro Gly Pro Pro
            35                  40                  45

Gly Pro Pro Gly Pro Pro Gly Pro Pro Gly Pro Pro Gly
    50                  55                  60

<210> SEQ ID NO 2
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(5)
<223> OTHER INFORMATION: This region may encompass 1-5 repeating "Gly"
      residues
<220> FEATURE:
<221> NAME/KEY: MISC_FEATURE
<222> LOCATION: (6)..(50)
<223> OTHER INFORMATION: This region may encompass 1-15 repeating "Pro
      Hyp Gly" units
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
```

```
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp
<220> FEATURE:
<221> NAME/KEY: MOD_RES
<222> LOCATION: (31)..(31)
<223> OTHER INFORMATION: Hyp
<220> FEATURE:
<221> NAME/KEY: MOD_RES
<222> LOCATION: (34)..(34)
<223> OTHER INFORMATION: Hyp
<220> FEATURE:
<221> NAME/KEY: MOD_RES
<222> LOCATION: (37)..(37)
<223> OTHER INFORMATION: Hyp
<220> FEATURE:
<221> NAME/KEY: MOD_RES
<222> LOCATION: (40)..(40)
<223> OTHER INFORMATION: Hyp
<220> FEATURE:
<221> NAME/KEY: MOD_RES
<222> LOCATION: (43)..(43)
<223> OTHER INFORMATION: Hyp
<220> FEATURE:
<221> NAME/KEY: MOD_RES
<222> LOCATION: (46)..(46)
<223> OTHER INFORMATION: Hyp
<220> FEATURE:
<221> NAME/KEY: MOD_RES
<222> LOCATION: (49)..(49)
<223> OTHER INFORMATION: Hyp

<400> SEQUENCE: 2

Gly Gly Gly Gly Gly Pro Pro Gly Pro Pro Gly Pro Pro Gly Pro Pro
1               5                   10                  15
Gly Pro Pro Gly Pro Pro Gly Pro Pro Gly Pro Pro Gly Pro Pro Gly
                20                  25                  30
Pro Pro Gly Pro Pro Gly Pro Pro Gly Pro Pro Gly Pro Pro Gly Pro
            35                  40                  45
Pro Gly
    50

<210> SEQ ID NO 3
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(45)
<223> OTHER INFORMATION: This region may encompass 1-15 repeating "Pro
```

-continued

```
            Hyp Gly" units
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp
<220> FEATURE:
<221> NAME/KEY: MOD_RES
<222> LOCATION: (32)..(32)
<223> OTHER INFORMATION: Hyp
<220> FEATURE:
<221> NAME/KEY: MOD_RES
<222> LOCATION: (35)..(35)
<223> OTHER INFORMATION: Hyp
<220> FEATURE:
<221> NAME/KEY: MOD_RES
<222> LOCATION: (38)..(38)
<223> OTHER INFORMATION: Hyp
<220> FEATURE:
<221> NAME/KEY: MOD_RES
<222> LOCATION: (41)..(41)
<223> OTHER INFORMATION: Hyp
<220> FEATURE:
<221> NAME/KEY: MOD_RES
<222> LOCATION: (44)..(44)
<223> OTHER INFORMATION: Hyp
<220> FEATURE:
<221> NAME/KEY: MISC_FEATURE
<222> LOCATION: (46)..(50)
<223> OTHER INFORMATION: This region may encompass 1-5 repeating "Tyr"
      residues

<400> SEQUENCE: 3

Pro Pro Gly Pro Pro Gly Pro Pro Gly Pro Pro Gly Pro Pro Gly
1               5                   10                  15

Pro Gly Pro Pro Gly Pro Pro Gly Pro Pro Gly Pro Pro Gly Pro Pro
            20                  25                  30

Gly Pro Pro Gly Pro Pro Gly Pro Pro Gly Pro Pro Gly Tyr Tyr Tyr
        35                  40                  45

Tyr Tyr
    50
```

```
<210> SEQ ID NO 4
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(5)
<223> OTHER INFORMATION: This region may encompass 1-5 repeating "Cys"
      residues
<220> FEATURE:
<221> NAME/KEY: MISC_FEATURE
<222> LOCATION: (6)..(50)
<223> OTHER INFORMATION: This region may encompass 1-15 repeating "Pro
      Hyp Gly" units
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp
<220> FEATURE:
<221> NAME/KEY: MOD_RES
<222> LOCATION: (31)..(31)
<223> OTHER INFORMATION: Hyp
<220> FEATURE:
<221> NAME/KEY: MOD_RES
<222> LOCATION: (34)..(34)
<223> OTHER INFORMATION: Hyp
<220> FEATURE:
<221> NAME/KEY: MOD_RES
<222> LOCATION: (37)..(37)
<223> OTHER INFORMATION: Hyp
<220> FEATURE:
<221> NAME/KEY: MOD_RES
<222> LOCATION: (40)..(40)
<223> OTHER INFORMATION: Hyp
<220> FEATURE:
<221> NAME/KEY: MOD_RES
<222> LOCATION: (43)..(43)
<223> OTHER INFORMATION: Hyp
<220> FEATURE:
<221> NAME/KEY: MOD_RES
<222> LOCATION: (46)..(46)
<223> OTHER INFORMATION: Hyp
<220> FEATURE:
<221> NAME/KEY: MOD_RES
<222> LOCATION: (49)..(49)
<223> OTHER INFORMATION: Hyp
```

-continued

```
<400> SEQUENCE: 4

Cys Cys Cys Cys Cys Pro Pro Gly Pro Pro Gly Pro Pro Gly Pro Pro
1               5                   10                  15

Gly Pro Pro Gly Pro Pro Gly Pro Pro Gly Pro Pro Gly Pro Pro Gly
            20                  25                  30

Pro Pro Gly Pro Pro Gly Pro Pro Gly Pro Pro Gly Pro Pro Gly Pro
        35                  40                  45

Pro Gly
    50

<210> SEQ ID NO 5
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(5)
<223> OTHER INFORMATION: This region may encompass 1-5 repeating "Cys"
      residues
<220> FEATURE:
<221> NAME/KEY: MISC_FEATURE
<222> LOCATION: (6)..(35)
<223> OTHER INFORMATION: This region may encompass 1-10 repeating "Pro
      Hyp Gly" units
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (10)..(10)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (16)..(16)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(25)
<223> OTHER INFORMATION: Hyp
<220> FEATURE:
<221> NAME/KEY: MOD_RES
<222> LOCATION: (28)..(28)
<223> OTHER INFORMATION: Hyp
<220> FEATURE:
<221> NAME/KEY: MOD_RES
<222> LOCATION: (31)..(31)
<223> OTHER INFORMATION: Hyp
<220> FEATURE:
<221> NAME/KEY: MOD_RES
<222> LOCATION: (34)..(34)
<223> OTHER INFORMATION: Hyp

<400> SEQUENCE: 5

Cys Cys Cys Cys Cys Pro Pro Gly Pro Pro Gly Pro Pro Gly Pro Pro
1               5                   10                  15

Gly Pro Pro Gly Pro Pro Gly Pro Pro Gly Pro Pro Gly Pro Pro Gly
            20                  25                  30
```

Pro Pro Gly
    35

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Methoxy-PEG2000-Gly
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp

<400> SEQUENCE: 6

Gly Gly Gly Pro Pro Gly Pro Pro Gly Pro Pro Gly Pro Pro Gly Pro
1               5                   10                  15

Pro Gly Pro Pro Gly Pro Pro Gly
                20

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)

```
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (30)..(30)
<223> OTHER INFORMATION: Gly-PEG5000

<400> SEQUENCE: 7

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Gly Gly Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ac-Gly
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
<221> NAME/KEY: MOD_RES
<222> LOCATION: (24)..(24)
<223> OTHER INFORMATION: Hyp
<220> FEATURE:
<221> NAME/KEY: MOD_RES
<222> LOCATION: (27)..(27)
<223> OTHER INFORMATION: Hyp
<220> FEATURE:
<221> NAME/KEY: MOD_RES
<222> LOCATION: (30)..(30)
<223> OTHER INFORMATION: Hyp

<400> SEQUENCE: 8

Gly Gly Gly Lys Gly Gly Gly Pro Pro Gly Pro Pro Gly Pro Pro Gly
1               5                   10                  15
```

-continued

```
Pro Pro Gly Pro Pro Gly Pro Pro Gly Pro Pro Gly
            20              25              30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This region may encompass 1-10 repeating "Pro
      Hyp Gly" units
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp

<400> SEQUENCE: 9

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly
            20              25              30

<210> SEQ ID NO 10
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(90)
<223> OTHER INFORMATION: This region may encompass 1-30 repeating "Pro
      Hyp Gly" units
<220> FEATURE:
<221> NAME/KEY: MOD_RES
```

```
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp
<220> FEATURE:
<221> NAME/KEY: MOD_RES
<222> LOCATION: (32)..(32)
<223> OTHER INFORMATION: Hyp
<220> FEATURE:
<221> NAME/KEY: MOD_RES
<222> LOCATION: (35)..(35)
<223> OTHER INFORMATION: Hyp
<220> FEATURE:
<221> NAME/KEY: MOD_RES
<222> LOCATION: (38)..(38)
<223> OTHER INFORMATION: Hyp
<220> FEATURE:
<221> NAME/KEY: MOD_RES
<222> LOCATION: (41)..(41)
<223> OTHER INFORMATION: Hyp
<220> FEATURE:
<221> NAME/KEY: MOD_RES
<222> LOCATION: (44)..(44)
<223> OTHER INFORMATION: Hyp
<220> FEATURE:
<221> NAME/KEY: MOD_RES
<222> LOCATION: (47)..(47)
<223> OTHER INFORMATION: Hyp
<220> FEATURE:
<221> NAME/KEY: MOD_RES
<222> LOCATION: (50)..(50)
<223> OTHER INFORMATION: Hyp
<220> FEATURE:
<221> NAME/KEY: MOD_RES
<222> LOCATION: (53)..(53)
<223> OTHER INFORMATION: Hyp
<220> FEATURE:
<221> NAME/KEY: MOD_RES
<222> LOCATION: (56)..(56)
<223> OTHER INFORMATION: Hyp
<220> FEATURE:
<221> NAME/KEY: MOD_RES
<222> LOCATION: (59)..(59)
<223> OTHER INFORMATION: Hyp
<220> FEATURE:
<221> NAME/KEY: MOD_RES
```

```
<222> LOCATION: (62)..(62)
<223> OTHER INFORMATION: Hyp
<220> FEATURE:
<221> NAME/KEY: MOD_RES
<222> LOCATION: (65)..(65)
<223> OTHER INFORMATION: Hyp
<220> FEATURE:
<221> NAME/KEY: MOD_RES
<222> LOCATION: (68)..(68)
<223> OTHER INFORMATION: Hyp
<220> FEATURE:
<221> NAME/KEY: MOD_RES
<222> LOCATION: (71)..(71)
<223> OTHER INFORMATION: Hyp
<220> FEATURE:
<221> NAME/KEY: MOD_RES
<222> LOCATION: (74)..(74)
<223> OTHER INFORMATION: Hyp
<220> FEATURE:
<221> NAME/KEY: MOD_RES
<222> LOCATION: (77)..(77)
<223> OTHER INFORMATION: Hyp
<220> FEATURE:
<221> NAME/KEY: MOD_RES
<222> LOCATION: (80)..(80)
<223> OTHER INFORMATION: Hyp
<220> FEATURE:
<221> NAME/KEY: MOD_RES
<222> LOCATION: (83)..(83)
<223> OTHER INFORMATION: Hyp
<220> FEATURE:
<221> NAME/KEY: MOD_RES
<222> LOCATION: (86)..(86)
<223> OTHER INFORMATION: Hyp
<220> FEATURE:
<221> NAME/KEY: MOD_RES
<222> LOCATION: (89)..(89)
<223> OTHER INFORMATION: Hyp

<400> SEQUENCE: 10

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly Pro Pro
                20                  25                  30

Gly Pro Pro Gly Pro Pro Gly Pro Pro Gly Pro Pro Gly Pro Pro Gly
            35                  40                  45

Pro Pro Gly Pro Pro Gly Pro Pro Gly Pro Pro Gly Pro Pro Gly Pro
        50                  55                  60

Pro Gly Pro Pro Gly Pro Pro Gly Pro Pro Gly Pro Pro Gly Pro Pro
65                  70                  75                  80

Gly Pro Pro Gly Pro Pro Gly Pro Pro Gly
                85                  90

<210> SEQ ID NO 11
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(90)
<223> OTHER INFORMATION: This region may encompass 1-30 repeating "Pro
      Pro Gly" units

<400> SEQUENCE: 11

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly Pro Pro
                20                  25                  30
```

-continued

```
Gly Pro Pro Gly Pro Pro Gly Pro Pro Gly Pro Pro Gly
            35                  40                  45

Pro Pro Gly Pro Pro Gly Pro Pro Gly Pro Pro Gly Pro
    50                  55                  60

Pro Gly Pro Pro Gly Pro Pro Gly Pro Pro Gly Pro Pro
65                  70                  75                  80

Gly Pro Pro Gly Pro Pro Gly Pro Pro Gly
                85                  90

<210> SEQ ID NO 12
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(90)
<223> OTHER INFORMATION: This region may encompass 1-30 repeating "Pro
      Flp Gly" units
<220> FEATURE:
<221> NAME/KEY: MOD_RES
<222> LOCATION: (2)..(2)
<223> OTHER INFORMATION: Flp
<220> FEATURE:
<221> NAME/KEY: MOD_RES
<222> LOCATION: (5)..(5)
<223> OTHER INFORMATION: Flp
<220> FEATURE:
<221> NAME/KEY: MOD_RES
<222> LOCATION: (8)..(8)
<223> OTHER INFORMATION: Flp
<220> FEATURE:
<221> NAME/KEY: MOD_RES
<222> LOCATION: (11)..(11)
<223> OTHER INFORMATION: Flp
<220> FEATURE:
<221> NAME/KEY: MOD_RES
<222> LOCATION: (14)..(14)
<223> OTHER INFORMATION: Flp
<220> FEATURE:
<221> NAME/KEY: MOD_RES
<222> LOCATION: (17)..(17)
<223> OTHER INFORMATION: Flp
<220> FEATURE:
<221> NAME/KEY: MOD_RES
<222> LOCATION: (20)..(20)
<223> OTHER INFORMATION: Flp
<220> FEATURE:
<221> NAME/KEY: MOD_RES
<222> LOCATION: (23)..(23)
<223> OTHER INFORMATION: Flp
<220> FEATURE:
<221> NAME/KEY: MOD_RES
<222> LOCATION: (26)..(26)
<223> OTHER INFORMATION: Flp
<220> FEATURE:
<221> NAME/KEY: MOD_RES
<222> LOCATION: (29)..(29)
<223> OTHER INFORMATION: Flp
<220> FEATURE:
<221> NAME/KEY: MOD_RES
<222> LOCATION: (32)..(32)
<223> OTHER INFORMATION: Flp
<220> FEATURE:
<221> NAME/KEY: MOD_RES
<222> LOCATION: (35)..(35)
<223> OTHER INFORMATION: Flp
<220> FEATURE:
<221> NAME/KEY: MOD_RES
<222> LOCATION: (38)..(38)
<223> OTHER INFORMATION: Flp
<220> FEATURE:
<221> NAME/KEY: MOD_RES
```

```
<222> LOCATION: (41)..(41)
<223> OTHER INFORMATION: Flp
<220> FEATURE:
<221> NAME/KEY: MOD_RES
<222> LOCATION: (44)..(44)
<223> OTHER INFORMATION: Flp
<220> FEATURE:
<221> NAME/KEY: MOD_RES
<222> LOCATION: (47)..(47)
<223> OTHER INFORMATION: Flp
<220> FEATURE:
<221> NAME/KEY: MOD_RES
<222> LOCATION: (50)..(50)
<223> OTHER INFORMATION: Flp
<220> FEATURE:
<221> NAME/KEY: MOD_RES
<222> LOCATION: (53)..(53)
<223> OTHER INFORMATION: Flp
<220> FEATURE:
<221> NAME/KEY: MOD_RES
<222> LOCATION: (56)..(56)
<223> OTHER INFORMATION: Flp
<220> FEATURE:
<221> NAME/KEY: MOD_RES
<222> LOCATION: (59)..(59)
<223> OTHER INFORMATION: Flp
<220> FEATURE:
<221> NAME/KEY: MOD_RES
<222> LOCATION: (62)..(62)
<223> OTHER INFORMATION: Flp
<220> FEATURE:
<221> NAME/KEY: MOD_RES
<222> LOCATION: (65)..(65)
<223> OTHER INFORMATION: Flp
<220> FEATURE:
<221> NAME/KEY: MOD_RES
<222> LOCATION: (68)..(68)
<223> OTHER INFORMATION: Flp
<220> FEATURE:
<221> NAME/KEY: MOD_RES
<222> LOCATION: (71)..(71)
<223> OTHER INFORMATION: Flp
<220> FEATURE:
<221> NAME/KEY: MOD_RES
<222> LOCATION: (74)..(74)
<223> OTHER INFORMATION: Flp
<220> FEATURE:
<221> NAME/KEY: MOD_RES
<222> LOCATION: (77)..(77)
<223> OTHER INFORMATION: Flp
<220> FEATURE:
<221> NAME/KEY: MOD_RES
<222> LOCATION: (80)..(80)
<223> OTHER INFORMATION: Flp
<220> FEATURE:
<221> NAME/KEY: MOD_RES
<222> LOCATION: (83)..(83)
<223> OTHER INFORMATION: Flp
<220> FEATURE:
<221> NAME/KEY: MOD_RES
<222> LOCATION: (86)..(86)
<223> OTHER INFORMATION: Flp
<220> FEATURE:
<221> NAME/KEY: MOD_RES
<222> LOCATION: (89)..(89)
<223> OTHER INFORMATION: Flp

<400> SEQUENCE: 12

Pro Pro Gly Pro Pro Gly Pro Pro Gly Pro Pro Gly Pro Pro Gly
 1               5                  10                  15

Pro Gly Pro Pro Gly Pro Pro Gly Pro Pro Gly Pro Pro Gly Pro
                20                  25                  30

Gly Pro Pro Gly Pro Pro Gly Pro Pro Gly Pro Pro Gly Pro Gly
            35                  40                  45

Pro Pro Gly Pro Pro Gly Pro Pro Gly Pro Pro Gly Pro Pro Gly Pro
     50                  55                  60
```

-continued

```
Pro Gly Pro Pro Gly Pro Gly Pro Pro Gly Pro Pro
65                  70                  75                  80

Gly Pro Pro Gly Pro Pro Gly Pro Pro Gly
                85                  90

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp

<400> SEQUENCE: 13

Gly Gly Gly Pro Pro Gly Pro Pro Gly Pro Pro Gly Pro Pro Gly Pro
1               5                   10                  15

Pro Gly Pro Pro Gly
            20

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
```

```
<220> FEATURE:
<221> NAME/KEY: MOD_RES
<222> LOCATION: (23)..(23)
<223> OTHER INFORMATION: Hyp

<400> SEQUENCE: 14

Gly Gly Gly Pro Pro Gly Pro Pro Gly Pro Pro Gly Pro Pro Gly Pro
1               5                   10                  15

Pro Gly Pro Pro Gly Pro Pro Gly
            20

<210> SEQ ID NO 15
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp

<400> SEQUENCE: 15

Gly Gly Gly Pro Pro Gly Pro Pro Gly Pro Pro Gly Pro Pro Gly Pro
1               5                   10                  15

Pro Gly Pro Pro Gly Pro Pro Gly Pro Pro Gly
            20                  25

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
```

```
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp

<400> SEQUENCE: 16

Gly Gly Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly
            20                  25                  30

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp

<400> SEQUENCE: 17

Pro Pro Gly Pro Pro Gly Pro Pro Gly Pro Pro Gly Pro Pro Gly Pro
1               5                   10                  15

Pro Gly Tyr

<210> SEQ ID NO 18
<211> LENGTH: 22
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp

<400> SEQUENCE: 18

Pro Pro Gly Pro Pro Gly Pro Pro Gly Pro Pro Gly Pro Pro Gly Pro
1               5                   10                  15

Pro Gly Pro Pro Gly Tyr
            20

<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
```

-continued

<400> SEQUENCE: 19

Pro Pro Gly Pro Pro Gly Pro Pro Gly Pro Pro Gly Pro Pro Gly Pro
1               5                   10                  15

Pro Gly Pro Pro Gly Pro Pro Gly Tyr
            20                  25

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp

<400> SEQUENCE: 20

Cys Pro Pro Gly Pro Pro Gly Pro Pro Gly
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp

<400> SEQUENCE: 21

Cys Pro Pro Gly Pro Pro Gly Pro Pro Gly Pro Pro Gly Pro Pro Gly
1               5                   10                  15

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)

```
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp

<400> SEQUENCE: 22

Cys Pro Pro Gly Pro Pro Gly Pro Pro Gly Pro Pro Gly Pro Pro Gly
1               5                   10                  15

Pro Pro Gly Pro Pro Gly
            20

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Carboxyfluorescein-Gly
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp

<400> SEQUENCE: 23

Gly Gly Gly Pro Pro Gly Pro Pro Gly Pro Pro Gly Pro Pro Gly Pro
1               5                   10                  15

Pro Gly Pro Pro Gly
            20
```

```
<210> SEQ ID NO 24
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Carboxyfluorescein-Gly
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
<221> NAME/KEY: MOD_RES
<222> LOCATION: (24)..(24)
<223> OTHER INFORMATION: Hyp
<220> FEATURE:
<221> NAME/KEY: MOD_RES
<222> LOCATION: (27)..(27)
<223> OTHER INFORMATION: Hyp

<400> SEQUENCE: 24

Gly Gly Gly Lys Pro Pro Gly Pro Pro Gly Pro Pro Gly Pro Pro Gly
1               5                   10                  15

Pro Pro Gly Pro Pro Gly Pro Pro Gly Pro Pro Gly
            20                  25

<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PEG2000-Gly
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
```

```
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp

<400> SEQUENCE: 25

Gly Gly Gly Pro Pro Gly Pro Pro Gly Pro Pro Gly Pro Pro Gly Pro
1               5                   10                  15

Pro Gly Pro Pro Gly Pro Pro Gly
            20

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (27)..(27)
<223> OTHER INFORMATION: Gly-PEG5000-OH

<400> SEQUENCE: 26

Pro Pro Gly Pro Pro Gly Pro Pro Gly Pro Pro Gly Pro Pro Gly Pro
1               5                   10                  15

Pro Gly Pro Pro Gly Pro Pro Gly Gly Gly Gly
            20                  25

<210> SEQ ID NO 27
<211> LENGTH: 31
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ac-Gly
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
<221> NAME/KEY: MOD_RES
<222> LOCATION: (24)..(24)
<223> OTHER INFORMATION: Hyp
<220> FEATURE:
<221> NAME/KEY: MOD_RES
<222> LOCATION: (27)..(27)
<223> OTHER INFORMATION: Hyp
<220> FEATURE:
<221> NAME/KEY: MOD_RES
<222> LOCATION: (30)..(30)
<223> OTHER INFORMATION: Hyp

<400> SEQUENCE: 27

Gly Gly Gly Lys Gly Gly Gly Pro Pro Gly Pro Pro Gly Pro Pro Gly
1               5                   10                  15

Pro Pro Gly Pro Pro Gly Pro Pro Gly Pro Pro Gly Pro Pro Gly
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: CF-Gly
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
```

```
<221> NAME/KEY: MOD_RES
<222> LOCATION: (24)..(24)
<223> OTHER INFORMATION: Hyp
<220> FEATURE:
<221> NAME/KEY: MOD_RES
<222> LOCATION: (27)..(27)
<223> OTHER INFORMATION: Hyp
<220> FEATURE:
<221> NAME/KEY: MOD_RES
<222> LOCATION: (30)..(30)
<223> OTHER INFORMATION: Hyp

<400> SEQUENCE: 28

Gly Gly Gly Lys Gly Gly Gly Pro Pro Gly Pro Pro Gly Pro Pro Gly
1               5                   10                  15

Pro Pro Gly Pro Pro Gly Pro Pro Gly Pro Pro Gly Pro Pro Gly
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ac-Gly
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
<221> NAME/KEY: MOD_RES
<222> LOCATION: (24)..(24)
<223> OTHER INFORMATION: Hyp
<220> FEATURE:
<221> NAME/KEY: MOD_RES
<222> LOCATION: (27)..(27)
<223> OTHER INFORMATION: Hyp
<220> FEATURE:
<221> NAME/KEY: MOD_RES
<222> LOCATION: (30)..(30)
<223> OTHER INFORMATION: Hyp

<400> SEQUENCE: 29

Gly Gly Gly Lys Gly Gly Pro Pro Gly Pro Pro Gly Pro Pro Gly
1               5                   10                  15

Pro Pro Gly Pro Pro Gly Pro Pro Gly Pro Pro Gly Pro Pro Gly
            20                  25                  30

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence: Synthetic
```

```
                              peptide
<220> FEATURE:
<221> NAME/KEY: MOD_RES
<222> LOCATION: (1)..(1)
<223> OTHER INFORMATION: FL-PEG2000-Gly
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp

<400> SEQUENCE: 30

Gly Gly Gly Pro Pro Gly Pro Pro Gly Pro Pro Gly Pro Pro Gly Pro
1               5                   10                  15

Pro Gly Pro Pro Gly Pro Pro Gly
            20

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 5 carboxyfluorescein-Gly
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
```

```
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (30)..(30)
<223> OTHER INFORMATION: Gly-PEG5000-OH

<400> SEQUENCE: 31

Gly Gly Gly Pro Pro Gly Pro Pro Gly Pro Pro Gly Pro Pro Gly Pro
1               5                   10                  15

Pro Gly Pro Pro Gly Pro Pro Gly Pro Pro Gly Gly Gly Gly
            20                  25                  30

<210> SEQ ID NO 32
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Ala Lys Gly
            20                  25                  30

Gly Phe Val Cys Lys Cys Tyr
            35

<210> SEQ ID NO 33
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Lys Ala Leu Leu Ala Leu Ala Leu His His Leu Ala His Leu Ala
1               5                   10                  15

Leu His Leu Ala Leu Ala Leu Lys Lys Ala
            20                  25

<210> SEQ ID NO 34
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Glu Arg Glu Asp Cys Trp Thr Phe Tyr Ala Asn Arg Lys Tyr Thr
1               5                   10                  15

Asp Phe Asp Lys Ser Phe Lys Lys Ser Ser Asp Leu Asp Glu Cys Lys
            20                  25                  30

Lys Thr Cys Phe Lys Thr Glu Tyr Cys Tyr Ile Val Phe Glu Asp Thr
            35                  40                  45

Val Asn Lys Glu Cys Tyr Tyr Asn Val Val Asp Gly Glu Glu Leu Asp
    50                  55                  60

Gln Glu Lys Phe Val Val Asp Glu Asn Phe Thr Glu Asn Tyr Leu Thr
```

```
                65                  70                  75                  80
Asp Cys Glu Gly Lys Asp Ala Gly Asn Ala Ala Gly Thr Gly Asp Glu
                85                  90                  95

Ser Asp Glu Val Asp Glu Asp Lys
            100

<210> SEQ ID NO 35
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Leu Thr Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln Lys
65

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
```

```
<222> LOCATION: (29)..(29)
<223> OTHER INFORMATION: Hyp

<400> SEQUENCE: 36

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly
            20                  25                  30

<210> SEQ ID NO 37
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 5CF-Gly
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp
<220> FEATURE:
<221> NAME/KEY: MOD_RES
<222> LOCATION: (32)..(32)
<223> OTHER INFORMATION: Hyp

<400> SEQUENCE: 37

Gly Gly Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly Pro Pro
            20                  25                  30

Gly

<210> SEQ ID NO 38
<211> LENGTH: 33
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 5CF-Gly
<220> FEATURE:
<221> NAME/KEY: MOD_RES
<222> LOCATION: (7)..(8)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (19)..(19)
<223> OTHER INFORMATION: Hyp
<220> FEATURE:
<221> NAME/KEY: MOD_RES
<222> LOCATION: (22)..(22)
<223> OTHER INFORMATION: Hyp
<220> FEATURE:
<221> NAME/KEY: MOD_RES
<222> LOCATION: (25)..(26)
<223> OTHER INFORMATION: Hyp
<220> FEATURE:
<221> NAME/KEY: MOD_RES
<222> LOCATION: (30)..(31)
<223> OTHER INFORMATION: Hyp

<400> SEQUENCE: 38

Gly Gly Gly Gly Pro Pro Pro Pro Gly Pro Gly Gly Gly Pro Pro Pro
1               5                   10                  15

Pro Gly Pro Gly Pro Pro Pro Gly Pro Pro Pro Gly Gly Pro Pro Pro
            20                  25                  30

Pro

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5CF-Gly
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
```

<223> OTHER INFORMATION: Hyp

<400> SEQUENCE: 39

Gly Gly Gly Pro Pro Gly Pro Pro Gly Pro Pro Gly Pro Pro Gly Pro
1               5                   10                  15

Pro Gly Pro Pro Gly
            20

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp

<400> SEQUENCE: 40

Pro Pro Gly Pro Pro Gly Pro Pro Gly Pro Gly Pro Pro Gly Pro
1               5                   10                  15

Pro Gly Pro Pro Gly
            20

<210> SEQ ID NO 41
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:

```
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (27)..(27)
<223> OTHER INFORMATION: Gly-PEG5000

<400> SEQUENCE: 41

Pro Pro Gly Pro Pro Gly Pro Pro Gly Pro Pro Gly Pro Pro Gly
1               5                   10                  15

Pro Pro Gly Pro Pro Gly Pro Pro Gly Gly Gly Gly
            20                  25

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp

<400> SEQUENCE: 42

Pro Pro Gly Pro Pro Gly Pro Pro Gly Pro Pro Gly Pro Pro Gly
1               5                   10                  15

Pro Pro Gly Pro Pro Gly Pro Pro Gly
            20

<210> SEQ ID NO 43
<211> LENGTH: 31
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Carboxyfluorescein-Gly
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
<221> NAME/KEY: MOD_RES
<222> LOCATION: (24)..(24)
<223> OTHER INFORMATION: Hyp
<220> FEATURE:
<221> NAME/KEY: MOD_RES
<222> LOCATION: (27)..(27)
<223> OTHER INFORMATION: Hyp
<220> FEATURE:
<221> NAME/KEY: MOD_RES
<222> LOCATION: (30)..(30)
<223> OTHER INFORMATION: Hyp

<400> SEQUENCE: 43

Gly Gly Gly Lys Gly Gly Gly Pro Pro Gly Pro Pro Gly Pro Pro Gly
1               5                   10                  15

Pro Pro Gly Pro Pro Gly Pro Pro Gly Pro Pro Gly Pro Pro Gly
                20                  25                  30

<210> SEQ ID NO 44
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (7)..(7)
<223> OTHER INFORMATION: Hyp
<220> FEATURE:
<221> NAME/KEY: MOD_RES
<222> LOCATION: (13)..(13)
<223> OTHER INFORMATION: Hyp
<220> FEATURE:
<221> NAME/KEY: MOD_RES
<222> LOCATION: (15)..(16)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
```

```
<222> LOCATION: (20)..(20)
<223> OTHER INFORMATION: Hyp

<400> SEQUENCE: 44

Cys Gly Pro Gly Pro Pro Pro Pro Gly Pro Pro Pro Gly Pro Pro
1               5                   10                  15

Pro Pro Gly Pro Gly Gly
            20

<210> SEQ ID NO 45
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACRL-PEG-Pro
<220> FEATURE:
<221> NAME/KEY: MOD_RES
<222> LOCATION: (2)..(2)
<223> OTHER INFORMATION: Hyp
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp

<400> SEQUENCE: 45

Pro Pro Gly Pro Pro Gly Pro Pro Gly Pro Pro Gly Pro Pro Gly Pro
1               5                   10                  15

Pro Gly Pro Pro Gly Tyr
            20

<210> SEQ ID NO 46
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: CF-Gly
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
```

```
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp
<220> FEATURE:
<221> NAME/KEY: MOD_RES
<222> LOCATION: (32)..(32)
<223> OTHER INFORMATION: Hyp

<400> SEQUENCE: 46

Gly Gly Gly Pro Pro Gly Pro Pro Gly Pro Pro Gly Pro Pro Gly Pro
1               5                   10                  15
Pro Gly Pro Pro Gly Pro Pro Gly Pro Pro Gly Pro Pro Gly Pro Pro
                20                  25                  30
Gly

<210> SEQ ID NO 47
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: CF-Gly
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
```

```
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (27)..(27)
<223> OTHER INFORMATION: Gly-PEG5000

<400> SEQUENCE: 47

Gly Gly Gly Pro Pro Gly Pro Pro Gly Pro Pro Gly Pro Pro Gly Pro
1               5                   10                  15

Pro Gly Pro Pro Gly Pro Pro Gly Pro Pro Gly
            20                  25

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: CF-Gly
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp

<400> SEQUENCE: 48

Gly Gly Gly Pro Pro Gly Pro Pro Gly Pro Pro Gly Pro Pro Gly Pro
1               5                   10                  15

Pro Gly Pro Pro Gly Pro Pro Gly
            20

<210> SEQ ID NO 49
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: CF-PEG2000-Gly
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp

<400> SEQUENCE: 49

Gly Gly Gly Pro Pro Gly Pro Pro Gly Pro Pro Gly Pro Pro Gly Pro
1               5                   10                  15

Pro Gly Pro Pro Gly Pro Pro Gly
            20

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hyp

<400> SEQUENCE: 50

Cys Pro Pro Gly
1

<210> SEQ ID NO 51
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: CF-Gly
<220> FEATURE:
<221> NAME/KEY: MOD_RES
<222> LOCATION: (5)..(5)
<223> OTHER INFORMATION: Hyp
<220> FEATURE:
<221> NAME/KEY: MOD_RES
<222> LOCATION: (8)..(8)
<223> OTHER INFORMATION: Hyp
<220> FEATURE:
<221> NAME/KEY: MOD_RES
<222> LOCATION: (11)..(11)
<223> OTHER INFORMATION: Hyp
```

```
<220> FEATURE:
<221> NAME/KEY: MOD_RES
<222> LOCATION: (14)..(14)
<223> OTHER INFORMATION: Hyp
<220> FEATURE:
<221> NAME/KEY: MOD_RES
<222> LOCATION: (17)..(17)
<223> OTHER INFORMATION: Hyp
<220> FEATURE:
<221> NAME/KEY: MOD_RES
<222> LOCATION: (20)..(20)
<223> OTHER INFORMATION: Hyp
<220> FEATURE:
<221> NAME/KEY: MOD_RES
<222> LOCATION: (23)..(23)
<223> OTHER INFORMATION: Hyp
<220> FEATURE:
<221> NAME/KEY: MOD_RES
<222> LOCATION: (26)..(26)
<223> OTHER INFORMATION: Hyp
<220> FEATURE:
<221> NAME/KEY: MOD_RES
<222> LOCATION: (29)..(29)
<223> OTHER INFORMATION: Hyp
<220> FEATURE:
<221> NAME/KEY: MOD_RES
<222> LOCATION: (32)..(32)
<223> OTHER INFORMATION: Hyp

<400> SEQUENCE: 51

Gly Gly Gly Pro Pro Gly Pro Pro Gly Pro Pro Gly Pro Pro Gly Pro
1               5                   10                  15
Pro Gly Pro Pro Gly Pro Pro Gly Pro Pro Gly Pro Pro Gly Pro Pro
            20                  25                  30
Gly
```